(12) United States Patent
Lyamichev et al.

(10) Patent No.: US 6,210,880 B1
(45) Date of Patent: Apr. 3, 2001

(54) POLYMORPHISM ANALYSIS BY NUCLEIC ACID STRUCTURE PROBING WITH STRUCTURE-BRIDGING OLIGONUCLEOTIDES

(75) Inventors: Victor I. Lyamichev; Fang Dong; Mary Ann D. Brow; Lance Fors; Bruce P. Neri, all of Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 0 days.

(21) Appl. No.: 08/934,097

(22) Filed: Sep. 19, 1997

(51) Int. Cl.[7] .............................. C12Q 1/68; C12P 19/34
(52) U.S. Cl. ................................. 435/6; 435/91.1
(58) Field of Search .................. 435/6, 91.1; 536/23.1, 536/24.3

(56) References Cited

U.S. PATENT DOCUMENTS 5,843,654 * 12/1998 Heisler et al. .......................... 435/6

OTHER PUBLICATIONS

Francois et al. (Nucleic Acids Research, vol. 22, pp 3943–3950), 1994.*

* cited by examiner

Primary Examiner—W. Gary Jones
Assistant Examiner—Jehanne Souaya

(57) ABSTRACT

The present invention relates to methods and compositions for analyzing nucleic acids. In particular, the present invention provides methods and compositions for the detection and characterization of nucleic acid sequences and sequence changes. The methods of the present invention permit the detection and/or identification of genetic polymorphism such as those associated with human disease and permit the identification of pathogens (e.g., viral and bacterial strain identification).

29 Claims, 21 Drawing Sheets

FIGURE 6

```
Consensus: GATTCTGTCT TCACGCAGAA AGCGTCTAGC CATGGCGTTA GTATGAGTGT CGTGCAGCCT
HCV 1a     ---------- ---------- ---------- ---------- ---------- ----------
HCV 1b     ---------- ---------- ---------- ---------- ---------- ----------
HCV 2c     ---------- ---------- -------C-- ---------- -----C---- ----A-----
HCV 3a     ---------- ---------- ---------- ---------- ---------- ----------

#249
           CCAGGACCCC CCCTCCCGGG AGAGCCATAG TGGTCTGCGG AACCGGTGAG TACACCGGAA
                                             #251
           ---------- ---------- ---------- ---------- ---------- ----------
           ----T----- ---------- ---------- ---------- ---------- ----------
           ----C----- ---------- ------A--- ---------- ---------- ----------
           ---------- ---------- ---------- ---------- ---------- ----------

#253                                       #257
           TTGCCAGGAC GACCGGGGTCC TTTCTTGGAT CAACCCGCTC AATGCCTTGA GATTTGGGCG
           ---------- ---------- ---------- ---------- ---------- ----------
           ----G---A- ---T------ ---------- ----A----- --T---C--C ----------
           -C--TG--GT ---------- ---------- ----G----- ---A--CA-- A---------
           ---------- ---------- ---------- ---------- ---------- ----------

#40        #261         #263
           TGCCCCCGCA AGACTGCTAG CCGAGTAGTG TTGGGGTCGCG AAAGGCCTTG TGGTACTGCC
           ---------- ---G------ ---------- ---------- ---------- ----------
           ---------- ---G------ ----C----- ----T----- ---------- ----------
           ---------- ---TCA---- ---------- ---------- ---------- ----------
           ---------- ---------- -------A-- ---------- ---------- ----------

TGATAGGGTG CTTGCGAGTG CCCCGGGAGG TCTCGTAGAC CGTGCAATC
           ---------- ---------- ---------- ---------- ---------
           ---------- ---------- ---------- ---------- ---------
           ---------- --------A- ---------- ---------- ---------
           ---------- ---------- ---------- ---------- ---------
```

FIGURE 8A
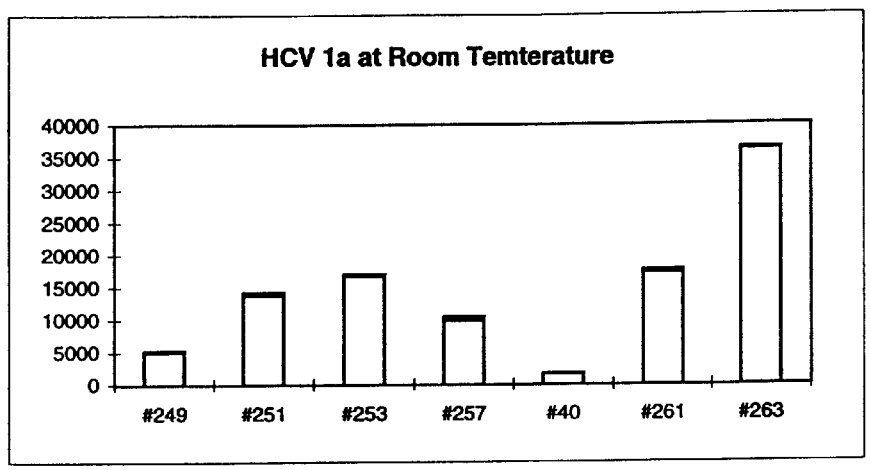
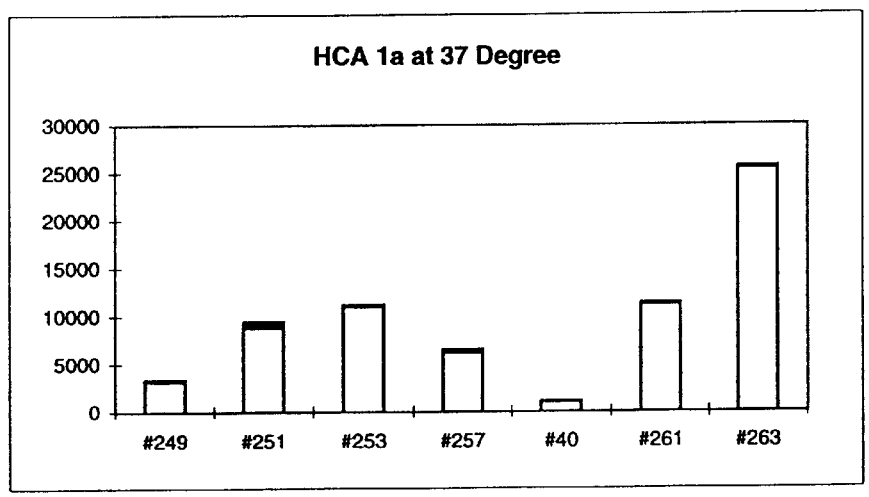
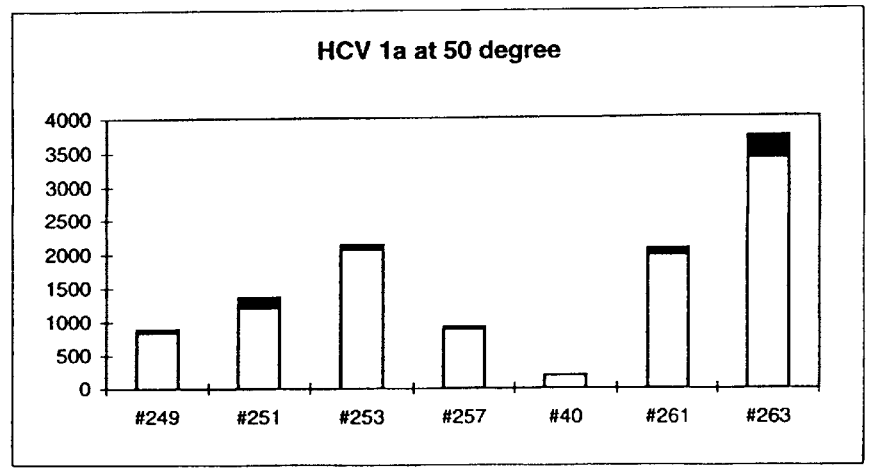

FIGURE 8B
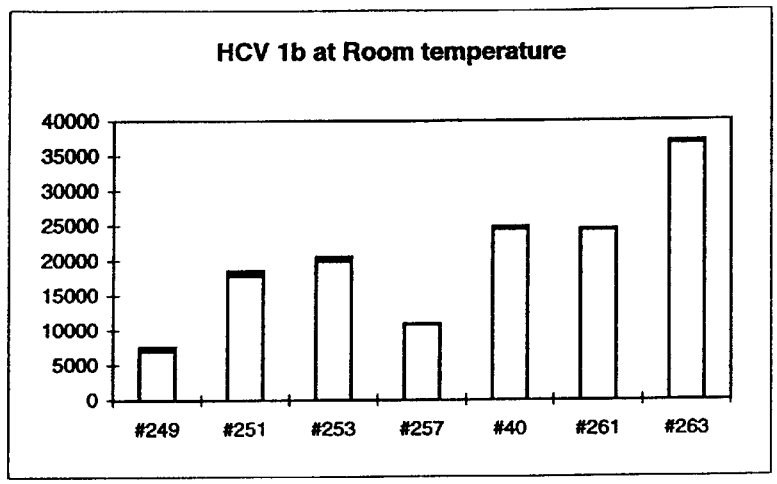
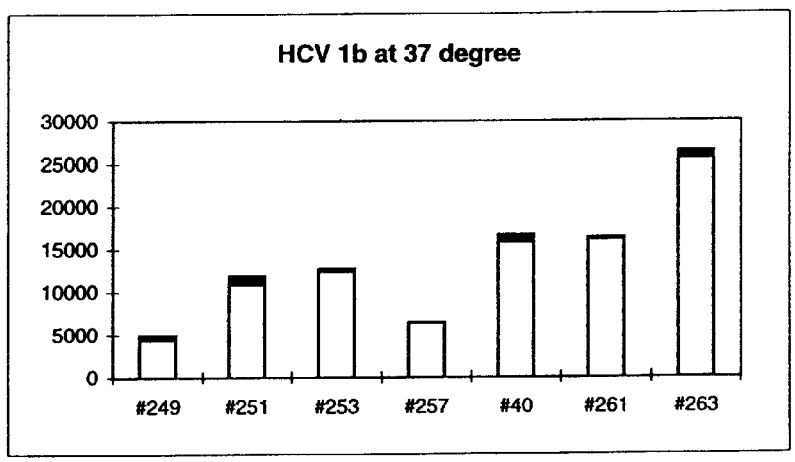
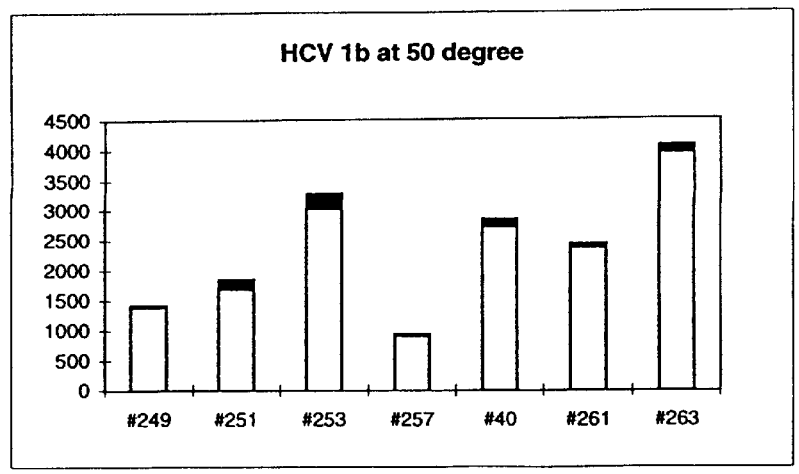

FIGURE 8C
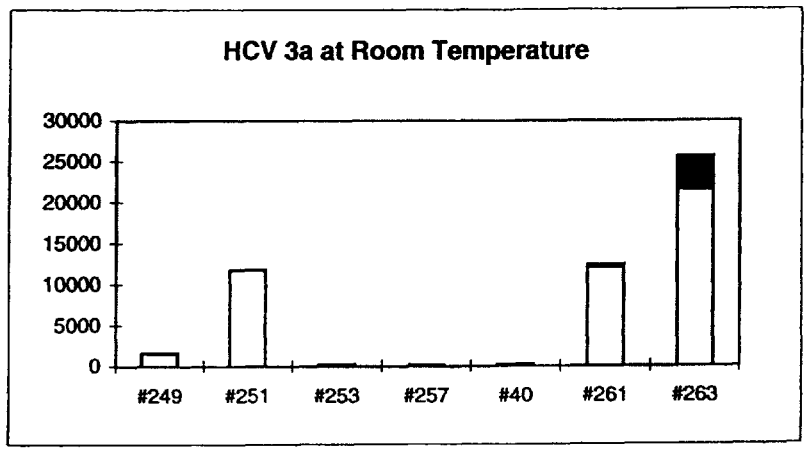
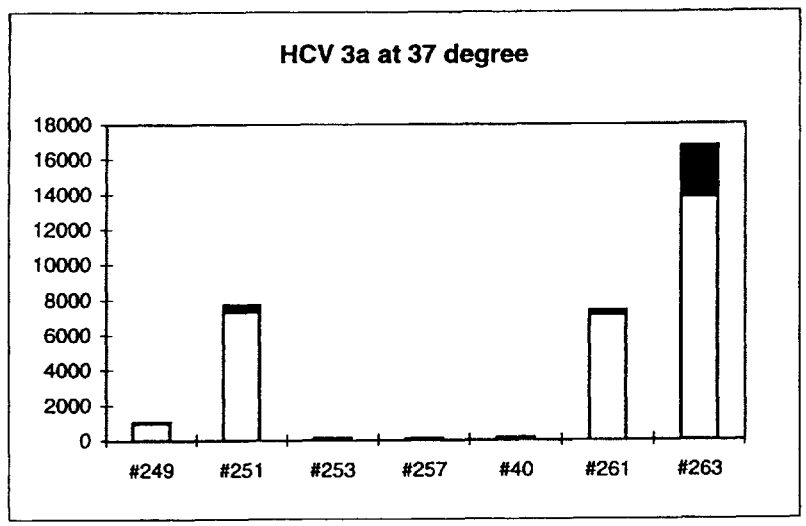
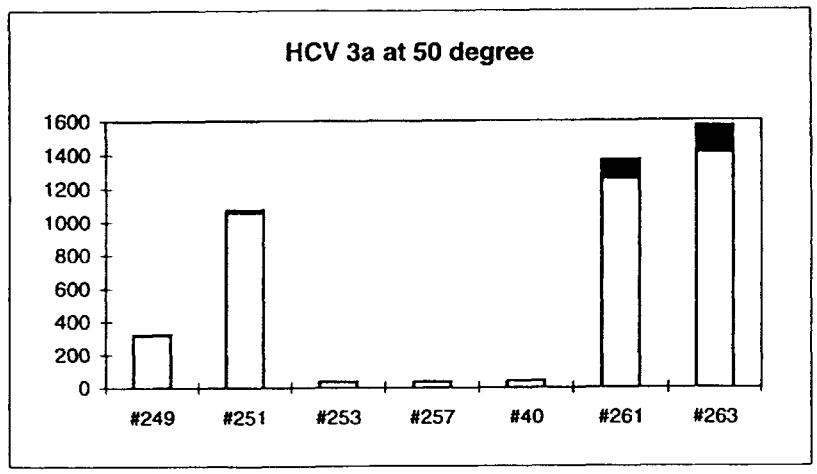

FIGURE 9D
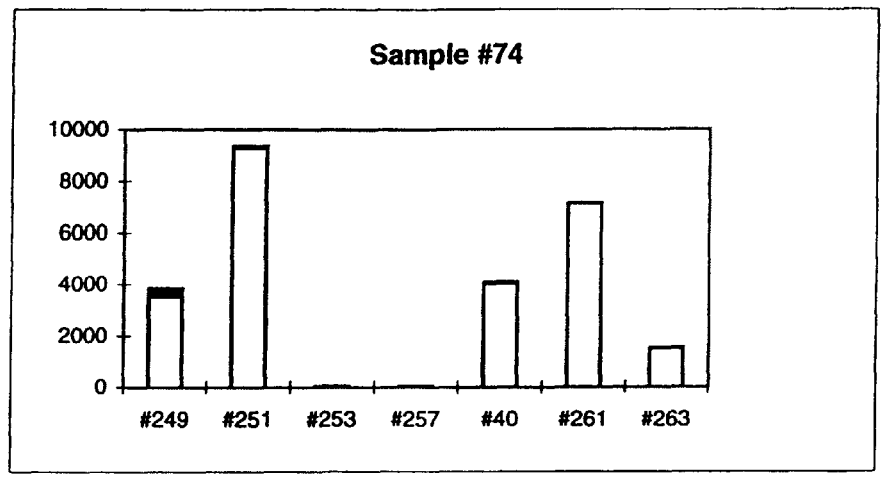
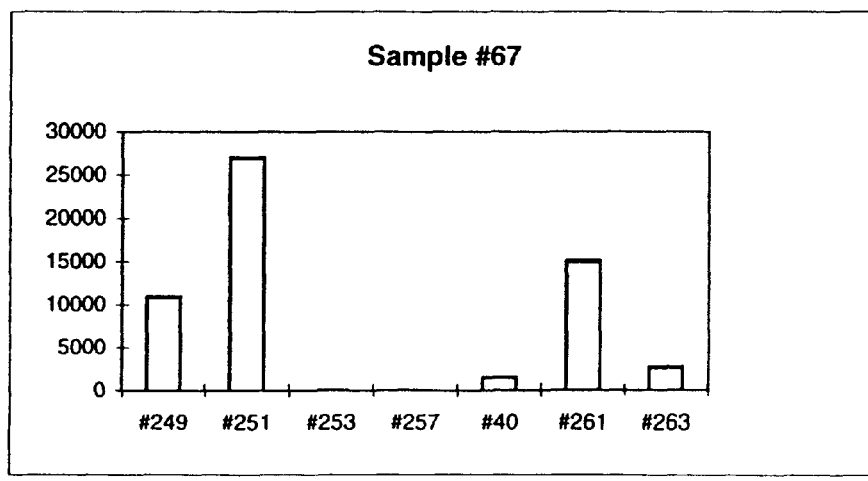

```
#2) 5' Biotin
        |
        T    A
    C   G    A
    A   T — A
    G   C — G
    A   T — A
    C   G — C
    A   T — A
    G   C — G
    C   G — C
    G   C — G
```
80) 5'-Fl-T G C T C T C T G G T        T G G T C T C T C G T A A T-3'

91) 3' Biotin - C G A G A G A C C A - 5'

```
            A
        G       A
        T — A
        C — G
        T — A
        G — C
        T — A
        C — G
        G — C
        C — G
```
80) 5'-Fl-T G C T C T C T G G T        T G G T C T C T C G T A A T-3'

78) 3' - A G A C C A T T A C C A G A -Biotin 5'

4) 3' - G A G A C C A T T A C C A G A G -Biotin 5'

79) 3' - A G A G A C C A T T A C C A G A G A -Biotin 5'

↓  ↓

116) 3' - A G A G A C C A A C C A G A G A -Biotin 5'

117) 3' - T A C C A G A G A -Biotin 5'

```
           A
        G     A
        T — A
        C — G
        T — A
        G — C
        T — A
        C — G
        G — C
        C — G
#80) 5'-Fl-T G C T C T C T G G T    T G G T C T C T C G T A A T-3'
   #79) 3'- A G A G A C C A—T T—A C C A G A G A -Biotin 5'
```

```
           A
        G     A
        T — A
        C — G
        T — A
        G — C
        T — A
        C — G
        G — C
        C — G
#80) 5'-Fl-T G C T C T C T G G T    T G G T C T C T C G T A A T-3'

3'- A G A G A C C A            A C C A G A G A -Biotin 5'
                       T             T
         #115          T             T         #114
                       A             A
                       C             C
              A ←→ C                 C ←→ A
                       A             A
                       G             G
              C ←→ A                 A ←→ C
                       G             G
                       A             A
                      /               \
                  Biotin 5'            3'
```

FIGURE 14
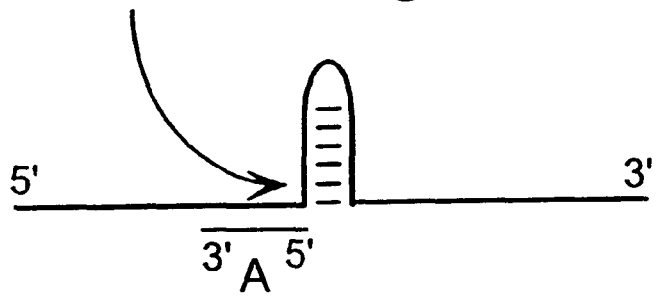
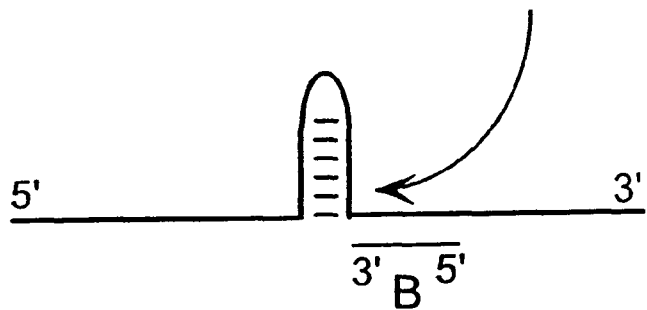
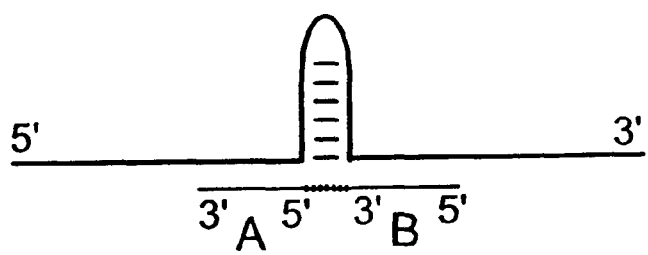

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
      (A) LENGTH: 391 base pairs
      (B) TYPE: nucleic acid
      (C) STRANDEDNESS: single
      (D) TOPOLOGY: linear (ii) MOLECULE TYPE: other nucleic acid
        (A) DESCRIPTION: /desc = "DNA"

(xi) SEQUENCE DESCRIPTION: SEQ ID NO:1:

| | | | | | | |
|---|---|---|---|---|---|---|
| AGCTCGTATG | GCACCGGAAC | CGGTAAGGAC | GCGATCACCA | GCGGCATCGA | GGTCGTATGG | 60 |
| ACGAACACCC | CGACGAAATG | GGACAACAGT | TTCCTCGAGA | TCCTGTACGG | CTACGAGTGG | 120 |
| GAGCTGACGA | AGAGCCCTGC | TGGCGCTTGG | CAATACACCG | CCAAGGACGG | CGCCGGTGCC | 180 |
| GGCACCATCC | CGGACCCGTT | CGGCGGGCCA | GGGCGCTCCC | CGACGATGCT | GGCCACTGAC | 240 |
| CTCTCGCTGC | GGGTGGATCC | GATCTATGAG | CGGATCACGC | GTCGCTGGCT | GGAACACCCC | 300 |
| GAGGAATTGG | CCGACGAGTT | CGCCAAGGCC | TGGTACAAGC | TGATCCACCG | AGACATGGGT | 360 |
| CCCGTTGCGA | GATACCTTGG | GCCGGTGGTC | C | | | 391 |

(2) INFORMATION FOR SEQ ID NO:2:

(i) SEQUENCE CHARACTERISTICS:
        (A) LENGTH: 391 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:2:

| | | | | | | |
|---|---|---|---|---|---|---|
| AGCTCGTATG | GCACCGGAAC | CGGTAAGGAC | GCGATCACCA | CCGGCATCGA | GGTCGTATGG | 60 |
| ACGAACACCC | CGACGAAATG | GGACAACAGT | TTCCTCGAGA | TCCTGTACGG | CTACGAGTGG | 120 |
| GAGCTGACGA | AGAGCCCTGC | TGGCGCTTGG | CAATACACCG | CCAAGGACGG | CGCCGGTGCC | 180 |
| GGCACCATCC | CGGACCCGTT | CGGCGGGCCA | GGGCGCTCCC | CGACGATGCT | GGCCACTGAC | 240 |
| CTCTCGCTGC | GGGTGGATCC | GATCTATGAG | CGGATCACGC | GTCGCTGGCT | GGAACACCCC | 300 |
| GAGGAATTGG | CCGACGAGTT | CGCCAAGGCC | TGGTACAAGC | TGATCCACCG | AGACATGGGT | 360 |
| CCCGTTGCGA | GATACCTTGG | GCCGCTGGTC | C | | | 391 |

(2) INFORMATION FOR SEQ ID NO:3:

(i) SEQUENCE CHARACTERISTICS:
        (A) LENGTH: 391 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:3:

| | | | | | | |
|---|---|---|---|---|---|---|
| AGCTCGTATG | GCACCGGAAC | CGGTAAGGAC | GCGATCACCA | GCGGCATCGA | GGTCGTATGG | 60 |
| ACGAACACCC | CGACGAAATG | GGACAACAGT | TTCCTCGAGA | TCCTGTACGG | CTACGAGTGG | 120 |
| GAGCTGACGA | AGAGCCCTGC | TGGCGCTTGG | CAATACACCG | CCAAGGACGG | CGCCGGTGCC | 180 |
| GGCACCATCC | CGGACCCGTT | CGGCGGGCCA | GGGCGCTCCC | CGACGATGCT | GGCCACTGAC | 240 |
| CTCTCGCTGC | GGGTGGATCC | GATCTATGAG | CGGATCACGC | GTCGCTGGCT | GGAACACCCC | 300 |
| GAGGAATTGG | CCGACGAGTT | CGCCAAGGCC | TGGTACAAGC | TGATCCACCG | AGACATGGGT | 360 |
| CCCGTTGCGA | GATACCTTGG | GCCGCTGGTC | C | | | 391 |

(2) INFORMATION FOR SEQ ID NO:4:

(i) SEQUENCE CHARACTERISTICS:
        (A) LENGTH: 391 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

```
AGCTCGTATG GCACCGGAAC CGGTAAGGAC GCGATCACCA CCGGCATCGA GGTCGTATGG      60

ACGAACACCC CGACGAAATG GGACAACAGT TTCCTCGAGA TCCTGTACGG CTACGAGTGG     120

GAGCTGACGA AGAGCCCTGC TGGCGCTTGG CAATACACCG CCAAGGACGG CGCCGGTGCC     180

GGCACCATCC CGGACCCGTT CGGCGGGCCA GGGCGCTCCC CGACGATGCT GGCCACTGAC     240

CTCTCGCTGC GGGTGGATCC GATCTATGAG CGGATCACGC GTCGCTGGCT GGAACACCCC     300

GAGGAATTGG CCGACGAGTT CGCCAAGGCC TGGTACAAGC TGATCCACCG AGACATGGGT     360

CCCGTTGCGA GATACCTTGG GCCGGTGGTC C                                   391
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:5:

```
AGCTCGTATG GCACCGGAAC                                                 20
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:6:

```
TTGACCTCCC ACCCGACTTG                                                 20
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:7:

```
AGCTCGTATG GCACCGGAAC C                                               21
```

```
(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:8:

GGACCAGCGG CCCAAGGTAT                                                    20

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:9:

GGACCACCGG CCCAAGGTAT CT                                                 22

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:10:

TTTTTGCCGC TGGTGATCGC G                                                  21

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:11:

GGAGAGCCAT AG                                                            12

(2) INFORMATION FOR SEQ ID NO:12:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:12:

TGGTCTGCGG A                                                             11
```

(2) INFORMATION FOR SEQ ID NO:13:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:13:

GGACGACCGG G                                                    11

(2) INFORMATION FOR SEQ ID NO:14:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:14:

GGAGATTTGG G                                                    11

(2) INFORMATION FOR SEQ ID NO:15:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

CCGCGAGACT G                                                    11

(2) INFORMATION FOR SEQ ID NO:16:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

CTAGCCGAGT AG                                                   12

(2) INFORMATION FOR SEQ ID NO:17:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:17:

TGTTGGGTCG C                                                    11

(2) INFORMATION FOR SEQ ID NO:18:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:18:

```
CCGCGAGACC G                                                           11
```

(2) INFORMATION FOR SEQ ID NO:19:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:19:

```
CCGCAAGACC G                                                           11
```

(2) INFORMATION FOR SEQ ID NO:20:

(i) SEQUENCE CHARACTERISTICS:
        (A) LENGTH: 289 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:20:

```
GATTCTGTCT TCACGCAGAA AGCGTCTAGC CATGGCGTTA GTATGAGTGT CGTGCAGCCT        60
CCAGGACCCC CCCTCCCGGG AGAGCCATAG TGGTCTGCGG AACCGGTGAG TACACCGGAA       120
TTGCCAGGAC GACCGGGTCC TTTCTTGGAT CAACCCGCTC AATGCCTGGA GATTTGGGCG       180
TGCCCCCGCA AGACTGCTAG CCGAGTAGTG TTGGGTCGCG AAAGGCCTTG TGGTACTGCC       240
TGATAGGGTG CTTGCGAGTG CCCCGGGAGG TCTCGTAGAC CGTGCAATC                   289
```

(2) INFORMATION FOR SEQ ID NO:21:

(i) SEQUENCE CHARACTERISTICS:
        (A) LENGTH: 286 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:21:

```
GATTCTGTCT TCACGCAGAA AGCGTCTAGC CATGGCGTTA GTATGAGTGT CGTGCAGCCT        60
CCAGGTCCCC CCCTCCCGGG AGAGCCATAG TGGTCTGCGG AACCGGTGAG TACACCGGAA       120
TTGCCAGGAC GACCGGGTCC TTTCTTGGAT CAACCCGCTC AATGCCTGGA GATTTGGGCG       180
TGCCCCCGCG AGACTGCTAG CCGAGTAGTG TTGGGTCGCG AAAGGCCTTG TGGTACTGCC       240
TGATAGGGTG CTTGCGAGTG CCCCGGGAGG TCTCGTAGAC CGTGCA                     286
```

(2) INFORMATION FOR SEQ ID NO:22:

(i) SEQUENCE CHARACTERISTICS:
        (A) LENGTH: 289 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:22:

```
GATTCTGTCT TCACGCAGAA AGCGTCTAGC CATGGCGTTA GTATGAGTGT CGTACAGCCT      60

CCAGGCCCCC CCCTCCCGGG AGAGCCATAG TGGTCTGCGG AACCGGTGAG TACACCGGAA     120

TTGCCGGGAA GACTGGGTCC TTTCTTGGAT AAACCCACTC TATGCCCGGC CATTTGGGCG     180

TGCCCCCGCA AGACTGCTAG CCGAGTAGCG TTGGGTTGCG AAAGGCCTTG TGGTACTGCC     240

TGATAGGGTG CTTGCGAGTA CCCCGGGAGG TCTCGTAGAC CGTGCAATC                 289
```

(2) INFORMATION FOR SEQ ID NO:23:

(i) SEQUENCE CHARACTERISTICS:
        (A) LENGTH: 289 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:23:

```
GATTCTGTCT TCACGCAGAA AGCGCCTAGC CATGGCGTTA GTACGAGTGT CGTGCAGCCT      60

CCAGGACCCC CCCTCCCGGG AGAACCATAG TGGTCTGCGG AACCGGTGAG TACACCGGAA     120

TCGCTGGGGT GACCGGGTCC TTTCTTGGAG CAACCCGCTC AATACCCAGA AATTTGGGCG     180

TGCCCCCGCG AGATCACTAG CCGAGTAGTG TTGGGTCGCG AAAGGCCTTG TGGTACTGCC     240

TGATAGGGTG CTTGCGAGTG CCCCGGGAGG TCTCGTAGAC CGTGCAATC                 289
```

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:24:

```
CTCGCAAGCA CCCTATCA                                                    18
```

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:25:

```
GCAGAAAGCG TCTAGCCATG G                                                21
```

(2) INFORMATION FOR SEQ ID NO:26:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:26:

```
GCAGAAAGCG TCTAGCCATG GCGTTAGTAT GAGTGTCGTG CAGCCTCCAG GACCCCCCCT      60

CCCGGGAGAG CCATAGTGGT CTGCGGAACC GGTGAGTACA CCGGAATTGC CAGGACGACC     120

GGGTCCTTTC TTGGATCAAC CCGCTCAATG CCTGGAGATT TGGGCGTGCC CCCGCAAGAC     180

TGCTAGCCGA GTAGTGTTGG GTCGCGAAAG GCCTTGTGGT ACTGCCTGAT AGGGTGCTTG     240

CGAG                                                                  244
```

(2) INFORMATION FOR SEQ ID NO:27:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:27:

```
GCAGAAAGCG TCTAGCCATG GCGTTAGTAT GAGTGTCGTG CAGCCTCCAG GTCCCCCCCT      60

CCCGGGAGAG CCATAGTGGT CTGCGGAACC GGTGAGTACA CCGGAATTGC CAGGACGACC     120

GGGTCCTTTC TTGGATCAAC CCGCTCAATG CCTGGAGATT TGGGCGTGCC CCCGCGAGAC     180

TGCTAGCCGA GTAGTGTTGG GTCGCGAAAG GCCTTGTGGT ACTGCCTGAT AGGGTGCTTG     240

CGAG                                                                  244
```

(2) INFORMATION FOR SEQ ID NO:28:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:28:

```
GCAGAAAGCG TCTAGCCATG GCGTTAGTAT GAGTGTCGTA CAGCCTCCAG GCCCCCCCCT      60

CCCGGGAGAG CCATAGTGGT CTGCGGAACC GGTGAGTACA CCGGAATTGC CGGGAAGACT     120

GGGTCCTTTC TTGGATAAAC CCACTCTATG CCCGGCCATT TGGGCGTGCC CCCGCAAGAC     180

TGCTAGCCGA GTAGCGTTGG GTTGCGAAAG GCCTTGTGGT ACTGCCTGAT AGGGTGCTTG     240

CGAG                                                                  244
```

(2) INFORMATION FOR SEQ ID NO:29:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:29:

GCAGAAAGCG CCTAGCCATG GCGTTAGTAC GAGTGTCGTG CAGCCTCCAG GACCCCCCCT    60

CCCGGGAGAA CCATAGTGGT CTGCGGAACC GGTGAGTACA CCGGAATCGC TGGGGTGACC    120

GGGTCCTTTC TTGGAGCAAC CCGCTCAATA CCCAGAAATT TGGGCGTGCC CCCGCGAGAT    180

CACTAGCCGA GTAGTGTTGG GTCGCGAAAG GCCTTGTGGT ACTGCCTGAT AGGGTGCTTG    240

CGAG                                                                 244

(2) INFORMATION FOR SEQ ID NO:30:

(i) SEQUENCE CHARACTERISTICS:
        (A) LENGTH: 216 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:30:

CAGAAAGGGT TTAGCCATGG GGTTAGTATG AGTGTCGTAC AGCCTCCAGG CCCCCCCCTC    60

CCGGGAGAGC CATAGTGGTC TGCGGAACCG GTGAGTACAC CGGAATTGCC GGGAAGACTG    120

GGTCCTTTCT TGGATAAACC CACTCTATGC CCGGCCATTT GGGCGTGCCC CGCAAGACT    180

GCTAGCCGAG TAGCGTTGGG TTGCGAAAGG CCTTGT                               216

(2) INFORMATION FOR SEQ ID NO:31:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:31:

CAGAAAGGGT TTAGCCATGG CGTTAGTATG AGTGTCGTGC AGCCTCCAGG ACCCCCCCTC    60

CCGGGAGAGC CATAGTGGTC TGCGGAACCG GTGAGTACAC CGGAATTGCC AGGACGACCG    120

GGTCCTTTCT TGGATAAAAC CCGCTCAATG CCTGGAGATT TGGGCGTGCC CCCGCAAGAC    180

TGCTAGCCGA GTAGTGTTGG GTCGCGAAAG GCCTTGTGGT ACTGCCTGAT AGGGTGCTTG    240

CAAG                                                                 244

(2) INFORMATION FOR SEQ ID NO:32:

(i) SEQUENCE CHARACTERISTICS:
        (A) LENGTH: 239 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:32:

GCAGAAAGGT TTAGCCATGG GTTAGTATGA GTGTCGTGCA GCCTCCAGGA CCCCCCCTCC    60

CGGGAGAGCC ATAGTGGTCT GCGGAACCGG TGAGTACACC GGAATTGCCA GGACGACCGG    120

```
GTCCTTTCTT GGATTAACCC GCTCAATGCC TGGAGATTTG GGCGTGCCCC CGCAAGACTG      180

CTAGCCGAGT AGTGTTGGGT CGCGAAAGGC CTTGTGGTAC TGCCTGATAG GGTGCTTGC      239
```

(2) INFORMATION FOR SEQ ID NO:33:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:33:

```
GCAGAAAGGT TTAGCCATGG GGTTAGTATG AGTGTCGTAC AGCCTCCAGG ACCCCCCCTC       60

CCGGGAGAGC CATAGTGGTC TGCGGAACCG GTGAGTACAC CGGAATTGCC AGGACGACCG      120

GGTCCTTTCT TGGATAAACC CGCTCAATGC CTGGAGATTT GGGCGTGCCC CCGCAAGACT      180

GCTAGCCGAG TAGTGTTGGG TCGCGAAAGG CCTTGTGGTA CTGCCTGATA GGGTGCTTGC      240
```

(2) INFORMATION FOR SEQ ID NO:34:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:34:

```
GCAGAAAGGG TTTAGCCATG GCGTTAGTAT GAGTGTCGTA CAGCCTCCAG GCCCCCCCCT       60

CCCGGGAGAG CCATAGTGGT CTGCGGAACC GGTGAGTACA CCGGAATTAC CGGAAAGACT      120

GGGTCCTTTC TTGGATAAAC CCACTCTATG TCCGGTCATT GGGCGTGCC CCCGCAAGAC      180

TGCTAGCCGA GTAGCGTTGG GTTGCAAAGG CCTTGTGGTA CTGCCTGATA GGGTGCTTGC      240
```

(2) INFORMATION FOR SEQ ID NO:35:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:35:

```
CAGAAAGGGT TTAGCCATGG GGTTAGTACG AGTGTCGTGC AGCCTCCAGG CCCCCCCCTC       60

CCGGGAGAGC CATAGTGGTC TGCGGAACCG GTGAGTACAC CGGAATCGCT GGGGTGACCG      120

GGTCCTTTCT TGGAGCAACC CGCTCAATAC CCAGAAATTT GGGCGTGCCC CCGCGAGATC      180

ACTAGCCGAG TAGTGTTGGG TCGCGAAAGG CCTTGTGGTA CTGCCTGATA GGGTGCTTGC      240
```

(2) INFORMATION FOR SEQ ID NO:36:

(i) SEQUENCE CHARACTERISTICS:
        (A) LENGTH: 239 base pairs
        (B) TYPE: nucleic acid
        (C) STRANDEDNESS: double
        (D) TOPOLOGY: linear (ii) MOLECULE TYPE: other nucleic acid
    (A) DESCRIPTION: /desc = "DNA"

(xi) SEQUENCE DESCRIPTION: SEQ ID NO:36:

| | | | |
|---|---|---|---|
| AGAAAGCGTT TAGCCATGGC GTTAGTATGA GTGTTGTGCA GCCTCCAGGA CCCCCCCTCC | 60 |
| CGGGAGAGCC ATAGTGGTCT GCGGAACCGG TGAGTACACC GGAATTGCCA GGACGACCGG | 120 |
| GTCCTTTCTT GGATCAACCC GCTCAATGCC TGGAGATTTG GGCGTGCCCC CGCAAGACTG | 180 |
| CTAGCCGAGT AGTGTTGGGT CGCGAAAGGC CTTGTGGTAC TGCCTGATAG GGTGCTTGC | 239 |

(2) INFORMATION FOR SEQ ID NO:37:

(i) SEQUENCE CHARACTERISTICS:
        (A) LENGTH: 232 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:37:

| | |
|---|---|
| GTTTAGCCAT GGCGTTAGTA TGAGTGTCGT GCAGCCTCCA GGACCCCCCC TCCCGGGAGA | 60 |
| GCCATAGTGG TCTGCGGAAC CGGTGAGTAC ACCGGAATTG CCAGGACGAC CGGGTCCTTT | 120 |
| CTTGGATCAA CCCGCTCAAT GCCTGGAGAT TTGGGCGTGC CCCCGCGAGA CCGCTAGCCG | 180 |
| AGTAGTGTTG GGTCGCGAAA GGCCTTGTGG TACTGCCTGA TAGGGTGCTT GC | 232 |

(2) INFORMATION FOR SEQ ID NO:38:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:38:

| | |
|---|---|
| GCAGAAAGCG TTTAGCCATG GCGTTAGTAC GAGTGTCGTG CAGCCTCCAG GACCCCCCCT | 60 |
| CCCGGGAGAG CCATAGTGGT CTGCGGAACC GGTGAGTACA CCGGAATCGC TGGGGTGACC | 120 |
| GGGTCCTTTC TTGGAACAAC CCGCTCAATA CCCAGAAATT TGGGCGTGCC CCCGCGAGAT | 180 |
| CACTAGCCGA GTAGTGTTGG GTCGCGAAAG GCCTTGTGGT ACTGCCTGAT AGGGTGCTTG | 240 |

(2) INFORMATION FOR SEQ ID NO:39:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:39:

| | |
|---|---|
| TGCTCTCTGG TCGCTGTCTG AAAGACAGCG TGGTCTCTCG TAAT | 44 |

(2) INFORMATION FOR SEQ ID NO:40:

(i) SEQUENCE CHARACTERISTICS:
        (A) LENGTH: 44 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:40:

TGCTCTCTGG TCGCTGTCTG AAAGACTCCG TGGTCTCTCG TAAT                    44

(2) INFORMATION FOR SEQ ID NO:41:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:41:

TGCTCTCTGG TCGCTGTCTG AATTTTTTTT TGGTCTCTCG TAAT                    44

(2) INFORMATION FOR SEQ ID NO:42:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:42:

AGACCATTAC CAGA                                                    14

(2) INFORMATION FOR SEQ ID NO:43:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:43:

GAGACCATTA CCAGAG                                                  16

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:44:

AGAGACCATT ACCAGAGA                                                18
```

(2) INFORMATION FOR SEQ ID NO:45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:45:

AGAGACCATT ACAAGCGA                                                     18

(2) INFORMATION FOR SEQ ID NO:46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:46:

AGCGAACATT ACCAGAGA                                                     18

(2) INFORMATION FOR SEQ ID NO:47:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:47:

AGAGACCAAC CAGAGA                                                       16

(2) INFORMATION FOR SEQ ID NO:48:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:48:

AGAGACCAT                                                                9

(2) INFORMATION FOR SEQ ID NO:49:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:49:

TACCAGAGA                                                                9

(2) INFORMATION FOR SEQ ID NO:50:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:50:

ACCAGAGAGC          10

(2) INFORMATION FOR SEQ ID NO:51:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:51:

TCAGACAGCG          10

POLYMORPHISM ANALYSIS BY NUCLEIC ACID STRUCTURE PROBING WITH STRUCTURE-BRIDGING OLIGONUCLEOTIDES

FIELD OF THE INVENTION

The present invention relates to methods and compositions for analyzing nucleic acids, and in particular, methods and compositions for detection and characterization of nucleic acid sequences and sequence changes.

BACKGROUND OF THE INVENTION

The detection and characterization of specific nucleic acid sequences and sequence changes have been utilized to detect the presence of viral or bacterial nucleic acid sequences indicative of an infection, the presence of variants or alleles of mammalian genes associated with disease and cancers, and the identification of the source of nucleic acids found in forensic samples, as well as in paternity determinations. As nucleic acid sequence data for genes from humans and pathogenic organisms accumulates, the demand for fast, cost-effective, and easy-to-use tests for as yet unknown, as well as known, mutations within specific sequences is rapidly increasing.

A handful of methods have been devised to scan nucleic acid segments for mutations. One option is to determine the entire gene sequence of each test sample (e.g., a clinical sample suspected of containing bacterial strain). For sequences under approximately 600 nucleotides, this may be accomplished using amplified material (e.g., PCR reaction products). This avoids the time and expense associated with cloning the segment of interest. However, specialized equipment and highly trained personnel are required for DNA sequencing, and the method is too labor-intense and expensive to be practical and effective in the clinical setting.

In view of the difficulties associated with sequencing, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

For detection of single-base differences between like sequences (e.g., the wild type and a mutant form of a gene), the requirements of the analysis are often at the highest level of resolution. For cases in which the position of the nucleotide in question is known in advance, several methods have been developed for examining single base changes without direct sequencing. For example, if a mutation of interest happens to fall within a restriction recognition sequence, a change in the pattern of digestion can be used as a diagnostic tool (e.g., restriction fragment length polymorphism [RFLP] analysis). In this way, single point mutations can be detected by the creation or destruction of RFLPs.

Single-base mutations have also been identified by cleavage of RNA-RNA or RNA-DNA heteroduplexes using RNaseA (Myers et al., Science 230:1242 [1985] and Winter et al., Proc. Natl. Acad. Sci. USA 82:7575 [1985]). Mutations are detected and localized by the presence and size of the RNA fragments generated by cleavage at the mismatches. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807–6817 [1990]). However, this method requires the use of osmium tetroxide and piperidine, two highly noxious chemicals which are not suited for use in a clinical laboratory. In addition, all of the mismatch cleavage methods lack sensitivity to some mismatch pairs, and all are prone to background cleavage at sites removed from the mismatch.

RFLP analysis suffers from low sensitivity and requires a large amount of sample. When RFLP analysis is used for the detection of point mutations, it is, by its nature, limited to the detection of only those single base changes which fall within a restriction sequence of a known restriction endonuclease. Moreover, the majority of the available enzymes have 4 to 6 base-pair recognition sequences, and cleave too frequently for many large-scale DNA manipulations (Eckstein and Lilley (eds.), Nucleic Acids and Molecular Biology, vol. 2, Springer-Verlag, Heidelberg [1988]). Thus, it is applicable only in a small fraction of cases, as most mutations do not fall within such sites.

A handful of rare-cutting restriction enzymes with 8 base-pair specificities have been isolated and these are widely used in genetic mapping, but these enzymes are few in number, are limited to the recognition of G+C-rich sequences, and cleave at sites that tend to be highly clustered (Barlow and Lelrach, Trends Genet., 3:167 [1987]). Recently, endonucleases encoded by group I introns have been discovered that might have greater than 12 base-pair specificity (Perlman and Butow, Science 246:1106 [1989]), but again, these are few in number.

If the change is not in a restriction enzyme recognition sequence, then allele-specific oligonucleotides (ASOs), can be designed to hybridize in proximity to the unknown nucleotide, such that a primer extension or ligation event can be used as the indicator of a match or a mis-match. Hybridization with radioactively labeled allelic specific oligonucleotides (ASO) also has been applied to the detection of specific point mutations (Conner, Proc. Natl. Acad. Sci., 80:278 [1983]). The method is based on the differences in the melting temperature of short DNA fragments differing by a single nucleotide (Wallace et al., Nucl. Acids Res., 6:3543 [1979]). Similarly, hybridization with large arrays of short oligonucleotides was proposed as a method for DNA sequencing (Bains and Smith, J. Theor. Biol., 135:303 [1988]) (Drmanac et al., Genomics 4:114 [1989]). To perform either method it is necessary to work under conditions in which the formation of mismatched duplexes is eliminated or reduced while perfect duplexes still remain stable. Such conditions are termed "high stringency" conditions. The stringency of hybridization conditions can be altered in a number of ways known in the art. In general, changes in conditions that enhance the formation of nucleic acid duplexes, such as increases in the concentration of salt, or reduction in the temperature of the solution, are considered to reduce the stringency of the hybridization conditions. Conversely, reduction of salt and elevation of temperature are considered to increase the stringency of the conditions. Because it is easy to change and control, variation of the temperature is commonly used to control the stringency of nucleic acid hybridization reactions.

Discrimination of hybridization based solely on the presence of a mismatch imposes a limit on probe length because effect of a single mismatch on the stability of a duplex is smaller for longer duplexes. For oligonucleotides designed to detect mutation in genomes of high complexity, such as human DNA, it has been shown that the optimal length for hybridization is between 16 and 22 nucleotides, and the temperature window within which the hybridization stringency will allow single base discrimination can be as large as 10° C. (Wallace [1979], supra). Usually, however, it is much narrower, and for some mismatches, such as G-T, it may be as small as 1 to 2° C. These windows may be even smaller if any other reaction conditions, such as temperature, pH, concentration of salt and the presence of destabilizing agents (e.g., urea, formamide, dimethylsulfoxide) alter the stringency. Thus, for successful detection of mutations using such high stringency hybridization methods, a tight control of all parameters affecting duplex stability is critical.

In addition to the degree of homology between the oligonucleotide probe and the target nucleic acid, efficiency of hybridization also depends on the secondary structure of the target molecule. Indeed, if the region of the target molecule that is complementary to the probe is involved in the formation of intramolecular structures with other regions of the target, this will reduce the binding efficiency of the probe. Interference with hybridization by such secondary structure is another reason why high stringency conditions are so important for sequence analysis by hybridization. High stringency conditions reduce the probability of secondary structures formation (Gamper et al., J. Mol. Biol., 197:349 [1987]). Another way to of reducing the probability of secondary structure formation is to decrease the length of target molecules, so that fewer intrastrand interactions can occur. This can be done by a number of methods, including enzymatic, chemical or thermal cleavage or degradation. Currently, it is standard practice to perform such a step in commonly used methods of sequence analysis by hybridization to fragment the target nucleic acid into short oligonucleotides (Fodor et al., Nature 364:555 [1993]).

Two other methods of mutation detection rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this maimer, variants can be distinguished, as differences in the melting properties of homoduplexes versus heteroduplexes differing in a single nucleotide can be used to detect the presence of mutations in the target sequences because of the corresponding changes in the electrophoretic mobilities of the hetero- and homoduplexes. The fragments to be analyzed, usually PCR products, are "clamped" at one end by a long stretch of G-C base pairs (30–80) to allow complete denaturation of the sequence of interest without complete dissociation of the strands. The attachment of a GC "clamp" to the DNA fragments increases the fraction of mutations that can be recognized by DGGE (Abrams et al., Genomics 7:463 [1990]). Attaching a GC clamp to one primer is critical to ensure that the amplified sequence has a low dissociation temperature (Sheffield et al., Proc. Natl. Acad. Sci., 86:232 [1989]; and Lerman and Silverstein, Meth. Enzymol., 155:482 [1987]). Modifications of the technique have been developed, using temperature gradient gels (Wartell et al., Nucl. Acids Res., 18:2699–2701 [1990]), and the method can be also applied to RNA:RNA duplexes (Smith et al., Genomics 3:217 [1988]).

Limitations on the utility of DGGE include the requirement that the denaturing conditions must be optimized for each specific nucleic acid sequence to be tested. Furthermore, the method requires specialized equipment to prepare the gels and maintain the high temperatures required during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405 [1991]). CDGE requires that gels be performed under different denaturant conditions in order to reach high efficiency for the detection of unknown mutations. Both DGGE and CDGE are unsuitable for use in clinical laboratories.

An technique analogous to DGGE, termed temperature gradient gel electrophoresis (TGGE), uses a thermal gradient rather than a chemical denaturant gradient (Scholz et al., Hum. Mol. Genet., 2:2155 [1993]). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Another common method, called "Single-Strand Conformation Polymorphism" (SSCP) was developed by Hayashi, Sekya and colleagues (reviewed by Hayashi, PCR Meth. Appl., 1:34–38, [1991]) and is based on the observation that single strands of nucleic acid can take on characteristic conformations under non-denaturing conditions, and these conformations influence electrophoretic mobility. The complementary strands assume sufficiently different structures that the two strands may be resolved from one another. Changes in the sequence of a given fragment will also change the conformation, consequently altering the mobility and allowing this to be used as an assay for sequence variations (Orita, et al., Genomics 5:874 [1989]).

The SSCP process involves denaturing a DNA segment (e.g., a PCR product) that is labelled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

The dideoxy fingerprinting (ddF) technique is another technique developed to scan genes for the presence of unknown mutations (Liu and Sommer, PCR Methods Applic, 4:97 [1994]). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200–300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion subcloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

Another method of detecting sequence polymorphisms based on the conformation assumed by strands of nucleic acid is the Cleavase® Fragment Length Polymorphism (CFLP®) method (Brow et al., J. Clin. Microbiol., 34:3129 [1996]; PCT International Application No. PCT/US95/14673 [WO 96/15267]; U.S. Pat. No. 5,843,654 and Ser. No. 08/520,946). This method uses the actions of a structure specific nuclease to cleave the folded structures, thus creating a set of product fragments that can by resolved by size (e.g., by electrophoresis). This method is much less sensitive to size so that entire genes, rather than gene fragments, may be analyzed.

In many situations (e.g., in many clinical laboratories), electrophoretic separation and analysis may not be technically feasible, or may not be able to accommodate the processing of a large number of samples in a cost-effective manner. There is a clear need for a method of analyzing the characteristic conformations of nucleic acids without the need for either electrophoretic separation of conformations or fragments or for elaborate and expensive methods of visualizing gels (e.g., darkroom supplies, blotting equipment or fluorescence imagers).

SUMMARY OF THE INVENTION

The present invention relates to methods and compositions for treating nucleic acid, and in particular, methods and compositions for detection and characterization of nucleic acid sequences and sequence changes. The present invention provides methods for examining the conformations assumed by single strands of nucleic acid, forming the basis of novel methods of detection of specific nucleic acid sequences. The present invention contemplates use of novel detection methods for, among other uses, clinical diagnostic purposes, including but not limited to the detection and identification of pathogenic organisms.

The present invention contemplates using the interactions between probe oligonucleotides and folded nucleic acid strands in methods for detection and characterization of nucleic acid sequences and sequence changes. A complex formed by the specific interaction (i.e., reproducible and predictable under a given set of reaction conditions) of a probe that is at least partially complementary to a target nucleic acid sequence is referred to herein as a "probe/folded target nucleic acid complex." The interactions contemplated may be a combination of standard hybridization of oligonucleotides to contiguous, co-linear complementary bases, or may include standard basepairing to non-contiguous regions of complementarity on a strand of nucleic acid to be analyzed. In this context, the term "standard base pairing" refers to hydrogen bonding that occurs between complementary bases, adenosine to thymidine and guanine to cytosine to form double helical structures of the A or B form. Such standard base pairing may also be referred to as Watson-Crick base pairing. It is contemplated that the interactions between the oligonucleotides of the present invention (i.e., the probes and the targets) may include non-standard nucleic acid interactions known in the art, such as triplex structures, quadraplex aggregates, and the multibase hydrogen bonding such as is observed within nucleic acid tertiary structures, such as those found in tRNAs.

The present invention contemplates the use of probes that are designed to interact with non-contiguous regions of complementarity. In one embodiment, such probes are constructed by incorporating within a single oligonucleotide segments that are complementary to two or more non-contiguous regions in the target nucleic acid of interest.

In another embodiment, this mixture is present in an aqueous solution. The invention is not limited by the nature of the aqueous solution employed. The aqueous solution may contain mono- and divalent ions, non-ionic detergents, buffers, stabilizers, etc.

The present invention provides a method, comprising: a) providing: i) a folded target having a deoxyribonucleic acid (DNA) sequence comprising one or more double stranded regions and one or more single stranded regions; and ii) one or more oligonucleotide probes complementary to at least a portion of the folded target; and b) mixing the folded target and the one or more probes under conditions such that the probe hybridizes to the folded target to form a probe/folded target complex. The degree of complementarity between the probes and the target nucleic acids may be complete or partial (e.g., contain at least one mismatched base pair). The method is not limited by the nature of the target DNA employed to provide the folded target DNA. In one embodiment, the target DNA comprises single-stranded DNA. In another embodiment, the target DNA comprises double-stranded DNA. Folded target DNAs may be produced from either single-stranded or double-stranded target DNAs by denaturing (e.g., heating) the DNA and then permitting the DNA to form intra-strand secondary structures. The method is not limited by the manner in which the folded target DNA is generated. The target DNA may be denatured by a variety of methods known to the art including heating, exposure to alkali, etc. and then permitted to renature under conditions that favor the formation of intra-strand duplexes (e.g., cooling, diluting the DNA solution, neutralizing the pH, etc.).

The method is also not limited by the nature of the oligonucleotide probes; these probes may comprise DNA, RNA, PNA and combinations thereof as well as comprise modified nucleotides, universal bases, adducts, etc.

In a preferred embodiment, the method further comprises detecting the presence of the probe/folded target complex. When a detection step is employed either the probe or the target DNA (or both) may comprise a label (i.e., a detectable moiety); the invention is not limited by the nature of the label employed or the location of the label (i.e., 5' end, 3' end, internal to the DNA sequence). A wide variety of suitable labels are known to the art and include fluorescein, tetrachlorofluorescein, hexachlorofluorescein, Cy3, Cy5, digoxigenin, radioisotopes (e.g., $^{32}P$, $^{35}S$). In another preferred embodiment, the method further comprises quantitating the amount of probe/folded target complex formed. The method is not limited by the means used for quantification; when a labeled folded target DNA is employed (e.g., fluorescein or $^{32}P$), the art knows means for quantification (e.g., determination of the amount of fluorescence or radioactivity present in the probe/folded target complex).

In a preferred embodiment, the probe in the probe/folded target complex is hybridized to a single stranded region of the folded target. In another preferred embodiment, the probe comprises an oligonucleotide having a moiety that permits its capture by a solid support. The invention is not limited by the nature of the moiety employed to permit capture. Numerous suitable moieties are known to the art, including but not limited to, biotin, avidin and streptavidin. Further, it is known in the art that many small compounds, such as fluorescein and digoxigenin may serve as haptens for specific capture by appropriate antibodies. Protein conjugates may also be used to allow specific capture by antibodies.

In a preferred embodiment the detection of the presence of the probe/folded target complex comprises exposing the probe/folded target complex to a solid support under conditions such that the probe is captured by the solid support. As discussed in further detail below, numerous suitable solid supports are known to the art (e.g., beads, particles, dipsticks, wafers, chips, membranes or flat surfaces composed of agarose, nylon, plastics such as polystyrenes, glass or silicon) and may be employed in the present methods.

In a particularly preferred embodiment, the moiety comprises a biotin moiety and the solid support comprises a surface having a compound capable of binding to the biotin moiety, the compound selected from the group consisting of avidin and streptavidin.

In another embodiment, the folded target comprises a deoxyribonucleic acid sequence having a moiety that permits its capture by a solid support; as discussed above a number of suitable moieties are known and may be employed in the present method. In yet another embodiment, the detection of the presence of the probe/folded target complex comprises exposing the probe/folded target complex to a solid support under conditions such that the folded target is captured by the solid support. In a preferred embodiment, the moiety comprises a biotin moiety and the solid support comprises a surface having a compound capable of binding to the biotin moiety, the compound selected from the group consisting of avidin and streptavidin.

In a preferred embodiment, the probe is attached to a solid support; the probe is attached to the solid support in such a manner that the probe is available for hybridization with the folded target nucleic acid. The invention is not limited by the means employed to attach the probe to the solid support. The probe may be synthesized in situ on the solid support or the probe may be attached (post-synthesis) to the solid support via a moiety present on the probe (e.g., using a biotinylated probe and solid support comprising avidin or streptavidin). In another preferred embodiment, the folded target nucleic acid is attached to a solid support; this may be accomplished for example using moiety present on the folded target (e.g., using a biotinylated target nucleic acid and solid support comprising avidin or streptavidin).

The present invention also provides a method, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) first and second oligonucleotide probes, the first oligonucleotide probe complementary to the first portion of the first and second folded targets and the second oligonucleotide probe complementary to the second portion of the first and second folded targets; and iv) a solid support comprising first, second, third and fourth testing zones, each zone capable of capturing and immobilizing the first and second oligonucleotide probes; b) contacting the first folded target with the first oligonucleotide probe under conditions such that the first probe binds to the first folded target to form a probe/folded target complex in a first mixture; c) contacting the first folded target with the second oligonucleotide probes under conditions such that the second probe binds to the first folded target to form a probe/folded target complex in a second mixture; d) contacting the second folded target with the first oligonucleotide probe to form a third mixture; e) contacting the second folded target with the second oligonucleotide probe to form fourth mixture; and f) adding the first, second, third and fourth mixtures to the first, second, third and fourth testing zones of the solid support, respectively, under conditions such that the probes are captured and immobilized. The degree of complementarity between the probes and the target nucleic acids may be complete or partial (e.g., contain at least one mismatched base pair).

In a preferred embodiment, the first probe in step d) does not substantially hybridize to the second folded target; that is while it is not required that absolutely no formation of a first probe/second folded target complex occurs, very little of this complex is formed. In another preferred embodiment, the hybridization of the first probe in step d) to the second folded target is reduced relative to the hybridization of the first probe in step c) to the first folded target.

The method is not limited by the nature of the first and second targets. The first and second targets may comprise double- or single-stranded DNA or RNA. The method is also not limited by the nature of the oligonucleotide probes; these probes may comprise DNA, RNA, PNA and combinations thereof as well as comprise modified nucleotides, universal bases, adducts, etc. In a preferred embodiment, the first and second oligonucleotide probes comprise DNA.

The present invention further provides a method, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) a solid support comprising first and second testing zones, each of the zones comprising immobilized first and second oligonucleotide probes, the first oligonucleotide probe complementary to the first portion of the first and second folded targets and second oligonucleotide probe complementary to the second portion of the first and second folded targets; and b) contacting the first and second folded targets with the solid support under conditions such that the first and second probes hybridize to the first folded target to form a probe/folded target complex. The invention is not limited by the nature of the first and second folded targets. The first and second targets may be derived from double- or single-stranded DNA or RNA. The probes may be completely or partially complementary to the target nucleic acids. The method is also not limited by the nature of the oligonucleotide probes; these probes may comprise DNA, RNA, PNA and combinations thereof as well as comprise modified nucleotides, universal bases, adducts, etc. In a preferred embodiment, the first and second oligonucleotide probes comprise DNA. The invention is not limited by the nature of the solid support employed as discussed above.

In a preferred embodiment, the contacting of step b) comprises adding the first folded target to the first testing zone and adding the second folded target to the second testing zone. In another preferred embodiment, the first and second probes are immobilized in separate portions of the testing zones.

In a preferred embodiment, the first probe in the second testing zone does not substantially hybridize to the second folded target; that is while it is not required that absolutely no formation of a first probe/second folded target complex occurs, very little of this complex is formed. In another preferred embodiment, the first probe in the second testing zone hybridizes to the second folded target with a reduced efficiency compared to the hybridization of the first probe in first testing zone to the first folded target.

In one embodiment, the first and second folded targets comprise DNA. In another embodiment, the first and second folded targets comprise RNA.

The present invention also provides a method for treating nucleic acid, comprising: a) providing: i) a nucleic acid target and ii) one or more oligonucleotide probes; b) treating the nucleic acid target and the probes under conditions such that the target forms one or more folded structures and interacts with one or more probes; and c) analyzing the complexes formed between the probes and the target. In a preferred embodiment, the method further comprises providing a solid support for the capture of the target/probe complexes. Such capture may occur after the formation of the structures, or either the probe or the target my be bound to the support before complex formation.

The method is not limited by the nature of the nucleic acid target employed. In one embodiment, the nucleic acid of step (a) is substantially single-stranded. In another embodiment, the nucleic acid is RNA or DNA. It is contemplated that the nucleic acid target comprise a nucleotide analog, including but not limited to the group comprising 7-deaza-dATP, 7-deaza-dGTP and dUTP. The nucleic acid target may be double stranded. When double-stranded nucleic acid targets are employed, the treating of step (b) comprises: i) rendering the double-stranded nucleic acid substantially single-stranded; and ii) exposing the single-stranded nucleic acid to conditions such that the single-stranded nucleic acid has secondary structure. The invention is not limited by the method employed to render the double-stranded nucleic acid substantially single-stranded; a variety of means known to the art may be employed. A preferred means for rendering double stranded nucleic acid substantially single-stranded is by the use of increased temperature.

In a preferred embodiment, the method further comprises the step of detecting the one or more target/probe complexes. The invention is not limited by the methods used for the detection of the complex(es).

It is contemplated that the methods of the present invention be used for the detection and identification of microorganisms. It is contemplated that the microorganism(s) of the present invention be selected from a variety of microorganisms; it is not intended that the present invention be limited to any particular type of microorganism. Rather, it is intended that the present invention will be used with organisms including, but not limited to, bacteria, fungi, protozoa, ciliates, and viruses. It is not intended that the microorganisms be limited to a particular genus, species, strain, or serotype. Indeed, it is contemplated that the bacteria be selected from the group comprising, but not limited to members of the genera Campylobacter, Fscherichia, Mycobacterium, Salmonella, Shigella, and Staphylococcus. In one preferred embodiment, the microorganism(s) comprise strains of multi-drug resistant *Mycobacterium tuberculosis*. It is also contemplated that the present invention be used with viruses, including but not limited to hepatitis C virus, human immunodeficiency virus and simian immunodeficiency virus.

Another embodiment of the present invention contemplates a method for detecting and identifying strains of microorganisms, comprising the steps of extracting nucleic acid from a sample suspected of containing one or more microorganisms; and contacting the extracted nucleic acid with one or more oligonucleotide probes under conditions such that the extracted nucleic acid forms one or more secondary structures and interacts with one or more probes. In one embodiment, the method further comprises the step of capturing the complexes to a solid support. In yet another embodiment, the method further comprises the step of detecting the captured complexes. In one preferred embodiment, the present invention further comprises comparing the detected from the extracted nucleic acid isolated from the sample with separated complexes derived from one or more reference microorganisms. In such a case the sequence of the nucleic acids from one or more reference microorganisms may be related but different (e.g., a wild type control for a mutant sequence or a known or previously characterized mutant sequence).

In an alternative preferred embodiment, the present invention further comprises the step of isolating a polymorphic locus from the extracted nucleic acid after the extraction step, so as to generate a nucleic acid target, wherein the target is contacted with one or more probe oligonucleotides. In one embodiment, the isolation of a polymorphic locus is accomplished by polymerase chain reaction amplification. In an alternate embodiment, the polymerase chain reaction is conducted in the presence of a nucleotide analog, including but not limited to the group comprising 7-deaza-dATP, 7-deaza-dGTP and dUTP. It is contemplated that the polymerase chain reaction amplification will employ oligonucleotide primers matching or complementary to consensus gene sequences derived from the polymorphic locus. In one embodiment, the polymorphic locus comprises a ribosomal RNA gene. In a particularly preferred embodiment, the ribosomal RNA gene is a 16S ribosomal RNA gene.

The present invention also contemplates a process for creating a record reference library of genetic fingerprints characteristic (i.e., diagnostic) of one or more alleles of the various microorganisms, comprising the steps of providing a nucleic acid target derived from microbial gene sequences; comprising the steps of extracting nucleic acid from a sample suspected of containing one or more microorganisms; and contacting the extracted nucleic acid with one or more oligonucleotide probes under conditions such that the extracted nucleic acid forms one or more secondary structures and interacts with one or more probes; detecting the captured complexes; and maintaining a testable record reference of the captured complexes.

By the term "genetic fingerprint" it is meant that changes in the sequence of the nucleic acid (e.g., a deletion, insertion or a single point substitution) alter both the sequences detectable by standard base pairing, and alter the structures formed, thus changing the profile of interactions between the target and the probe oligonucleotides (e.g., altering the identity of the probes with which interaction occurs and/or altering the site/s or strength of the interaction). The measure of the identity of the probes bound and the strength of the interactions constitutes an informative profile that can serve as a "fingerprint" of the nucleic acid, reflecting the sequence and allowing rapid detection and identification of variants.

The methods of the present invention allow for simultaneous analysis of both strands (e.g., the sense and antisense strands) and are ideal for high-level multiplexing. The products produced are amenable to qualitative, quantitative and positional analysis. The present methods may be automated and may be practiced in solution or in the solid phase (e.g., on a solid support). The present methods are powerful in that they allow for analysis of longer fragments of nucleic acid than current methodologies.

The present invention further provides methods for determination of structure formation in nucleic acid targets, comprising the steps of: a) providing: i) a folded target having a deoxyribonucleic acid sequence comprising one or more double stranded regions, and one or more single stranded regions, and further comprising two or more non-contiguous portions, and one or more intervening regions; and ii) one or more bridging oligonucleotide probes complementary to two or more non-contiguous portions of the folded target; and b) mixing the folded target and one or more bridging oligonucleotide probes under conditions such that the bridging oligonucleotide probes hybridize to the folded target to form a probe/folded target complex.

In preferred embodiments, the one or more intervening regions of the folded targets comprise at least five nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. In alternative embodiments, the method further comprises detecting the presence of the probe/folded target complex. In yet other embodiments, the method further comprises quantitating the amount of probe/folded target complex formed. In yet other embodiments of the method, the bridging oligonucleotide probe in the probe/folded target complex is hybridized to at least one single stranded region of the folded target.

The method is not limited by the nature of the target DNA employed to provide the folded target DNA, nor is the method limited by the manner in which the folded target DNA is generated. The method is also not limited by the nature of the bridging oligonucleotide probes; these probes may comprise DNA, RNA, PNA and combinations thereof as well as comprise modified nucleotides, universal bases, adducts, etc.

In a preferred embodiment, the method further comprises detecting the presence of the probe/folded target complex. When a detection step is employed either the bridging oligonucleotide probe or the target DNA (or both) may comprise a label (i.e., a detectable moiety); the invention is not limited by the nature of the label employed or the location of the label (i.e., 5' end, 3' end, internal to the DNA sequence). A wide variety of suitable labels are known to the art and include fluorescein, tetrachlorofluorescein, hexachlorofluorescein, Cy3, Cy5, digoxigenin, radioisotopes (e.g., $^{32}$P, $^{35}$S). In another preferred embodiment, the method further comprises quantitating the amount of probe/folded target complex formed. The method is not limited by the means used for quantification; when a labeled folded target DNA is employed (e.g., fluorescein or $^{32}$P), the art knows means for quantification (e.g., determination of the amount of fluorescence or radioactivity present in the probe/folded target complex).

In another preferred embodiment, the bridging oligonucleotide probe comprises a bridging oligonucleotide having a moiety that permits its capture by a solid support. The invention is not limited by the nature of the moiety employed to permit capture. Numerous suitable moieties are known to the art, including but not limited to, biotin, avidin and streptavidin. Further, it is known in the art that many small compounds, such as fluorescein and digoxigenin may serve as haptens for specific capture by appropriate antibodies. Protein conjugates may also be used to allow specific capture by antibodies.

In a preferred embodiment the detection of the presence of the probe/folded target complex comprises exposing the probe/folded target complex to a solid support under conditions such that the bridging oligonucleotide probe is captured by the solid support. As discussed in further detail below, numerous suitable solid supports are known to the art (e.g., beads, particles, dipsticks, wafers, chips, membranes or flat surfaces composed of agarose, nylon, plastics such as polystyrenes, glass or silicon) and may be employed in the present methods.

In a particularly preferred embodiment, the moiety comprises a biotin moiety and the solid support comprises a surface having a compound capable of binding to the biotin moiety, the compound selected from the group consisting of avidin and streptavidin.

In another embodiment, the folded target comprises a deoxyribonucleic acid sequence having a moiety that permits its capture by a solid support; as discussed above a number of suitable moieties are known and may be employed in the present method. In yet another embodiment, the detection of the presence of the probe/folded target complex comprises exposing the probe/folded target complex to a solid support under conditions such that the folded target is captured by the solid support. In a preferred embodiment, the moiety comprises a biotin moiety and the solid support comprises a surface having a compound capable of binding to the biotin moiety, the compound selected from the group consisting of avidin and streptavidin.

In a preferred embodiment, the bridging oligonucleotide probe is attached to a solid support; the probe is attached to the solid support in such a manner that the bridging oligonucleotide probe is available for hybridization with the folded target nucleic acid. The invention is not limited by the means employed to attach the bridging oligonucleotide probe to the solid support. The bridging oligonucleotide probe may be synthesized in situ on the solid support or the probe may be attached (post-synthesis) to the solid support via a moiety present on the bridging oligonucleotide probe (e.g., using a biotinylated probe and solid support comprising avidin or streptavidin). In another preferred embodiment, the folded target nucleic acid is attached to a solid support; this may be accomplished for example using moiety present on the folded target (e.g., using a biotinylated target nucleic acid and solid support comprising avidin or streptavidin).

The present invention also provides methods for analyzing the structure of nucleic acid targets, comprising: a) providing: i) a first folded target having a nucleic acid sequence comprising first and second portions, the first and second portions each comprising one or more double stranded regions and one or more single stranded regions; ii) a second folded target having a nucleic acid sequence comprising a first portion that is identical to the first portion of the first folded target and a second portion that differs from the second portion of the first folded target because of a variation in nucleic acid sequence relative to the first folded target, the first and second portions each comprising one or more double stranded regions and one or more single stranded regions; iii) first and second bridging oligonucleotides, wherein the first bridging oligonucleotide is complementary to the first portion of the first and second folded targets and the second bridging oligonucleotide is complementary to the second portion of the first and second folded targets; and iv) a solid support comprising first, second, third and fourth testing zones, each zone capable of capturing and immobilizing the first and second bridging oligonucleotides; b) contacting the first folded target with the first bridging oligonucleotide under conditions such that the first bridging oligonucleotide binds to the first folded target to form a probe/folded target complex in a first mixture; c) contacting the first folded target with the second bridging oligonucleotide under conditions such that the second bridging oligonucleotide binds to the first folded target to form a probe/folded target complex in a second mixture; d) contacting the second folded target with the first bridging oligonucleotide to form a third mixture; e) contacting the second folded target with the second bridging oligonucleotide to form fourth mixture; and f) adding the first, second, third and fourth mixtures to the first, second, third and fourth testing zones of the solid support, respectively, under conditions such that the first and second bridging oligonucleotides are captured and immobilized.

The method is not limited by the nature of the first and second targets. The first and/or second target may comprise one or more non-contiguous regions, as well as one or more intervening regions. In preferred embodiments, the intervening regions comprise at least five nucleotides. The method is also not limited by the nature of the bridging oligonucleotide probes; these bridging oligonucleotide probes may comprise DNA, RNA, PNA and combinations thereof as well as comprise modified nucleotides, universal bases, adducts, etc. In some embodiments, the first and/or second bridging oligonucleotide probes comprise one or more intervening regions. In alternative embodiments, the intervening region of the bridging oligonucleotide probes comprises at least two nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. In a preferred embodiment, the first and second bridging oligonucleotide probes comprise DNA.

In alternative embodiments, the first bridging oligonucleotide in step d) does not substantially hybridize to the second folded target. In yet another embodiment, the hybridization of the first bridging oligonucleotide in step d) to the second folded target is reduced relative to the hybridization of the first bridging oligonucleotide in step c) to the first folded target. In further embodiments, the first and second targets comprise DNA, and/or the first and second bridging oligonucleotides comprise DNA.

The present invention also provides methods for analyzing folded nucleic acid targets, comprising: a) providing: i) a first folded target having a nucleic acid sequence comprising first and second portions, wherein the first and second portions each comprise one or more double stranded regions and one or more single stranded regions; ii) a second folded target having a nucleic acid sequence comprising a first portion that is identical to the first portion of the first folded target, and a second portion that differs from the second portion of the first folded target because of a variation in nucleic acid sequence relative to the first folded target, the first and second portions each comprising one or more double stranded regions and one or more single stranded regions; iii) a solid support comprising first and second testing zones, each of the zones comprising immobilized first and second bridging oligonucleotides, the first bridging oligonucleotide being complementary to the first portion of the first and second folded targets and second bridging oligonucleotide being complementary to the second portion of the first and second folded targets; and b) contacting the first and second folded targets with the solid support under conditions such that the first and second bridging oligonucleotides hybridize to the first folded target to form a probe/folded target complex.

In some embodiments, the contacting of step b) comprises adding the first folded target to the first testing zone and adding the second folded target to the second testing zone. In alternative embodiments, the first and second bridging oligonucleotides are immobilized in separate portions of the testing zones. In yet other embodiments, the first bridging oligonucleotide in the second testing zone does not substantially hybridize to the second folded target. In further embodiments, the first bridging oligonucleotide in the second testing zone hybridizes to the second folded target with a reduced efficiency compared to the hybridization of the first bridging oligonucleotide in first testing zone to the first folded target.

The method is not limited by the nature of, nor the method of generating the first and second folded targets. The method is also not limited by the nature of, or the method of generating the oligonucleotide probes; these probes may comprise DNA, RNA, PNA and combinations thereof as well as comprise modified nucleotides, universal bases, adducts, etc. In some embodiments, the first and/or second folded target comprises one or more intervening region comprised of at least five nucleotides. In yet other embodiments, the first and/or second bridging oligonucleotide probe comprises one or more intervening regions comprised of at least two nucleotides. In yet other embodiments, either of the targets and/or either of the bridging oligonucleotides contain intervening regions comprised of non-nucleotide spacers of any length. In a preferred embodiment, the first and second oligonucleotide probes comprise DNA. The invention is not limited by the nature of the solid support employed as discussed above. In some preferred embodiments of the method, the first and second folded targets comprise DNA. In alternative embodiments, the first and second folded targets comprise RNA. In yet other embodiments, the first and second bridging oligonucleotides comprise DNA.

DESCRIPTION OF THE FIGURES

FIGS. 2A–2D show portions of SEQ ID NOS:1–4 (structures 2A–2D, respectively).

FIG. 6 provides an alignment of sequences that have been determined for the HCV genotypes examined in Example 3. The sites within the HCV targets which the probes have been designed to complement are underlined and shown in bold. The numbers of the probes are indicated above each site. SEQ ID NOS:20–23 are shown in FIG. 6.

FIGS. 8A, B and C show graphs depicting the fluorescence signal measured after the solid support capture of the indicated HCV types by the indicated probes, at temperatures ranging from room temperature (approximately 22° C.) to 50° C.

FIGS. 9A–9D show graphs depicting the fluorescence signal measured after the solid support capture of different HCV types from clinical samples, by the indicated probes.

FIG. 10 shows schematic representations of the folded structures that would be assumed by each of the three test molecules, #80 (SEQ ID NO:39), #81 (SEQ ID NO:40) and #82 (SEQ ID NO:41).

FIGS. 11A and 11B show schematic representations of the capture oligonucleotides used in these studies. While are were tested with all three of the test molecules depicted in FIG. 10, for convenience they are shown aligned with their complementary regions in test molecule #80 (SEQ ID NO:39).

FIG. 14 shows a schematic diagram of the process for selecting two segments of bridging oligonucleotide based on the data from the use of 5' and 3' nucleases to cleave a folded structure. Such cleavage reactions can be used to locate regions that are either upstream and downstream of folded structures, facilitating selection of complementary sequences to compose bridging oligonucleotides.

DEFINITIONS

Figure 1:
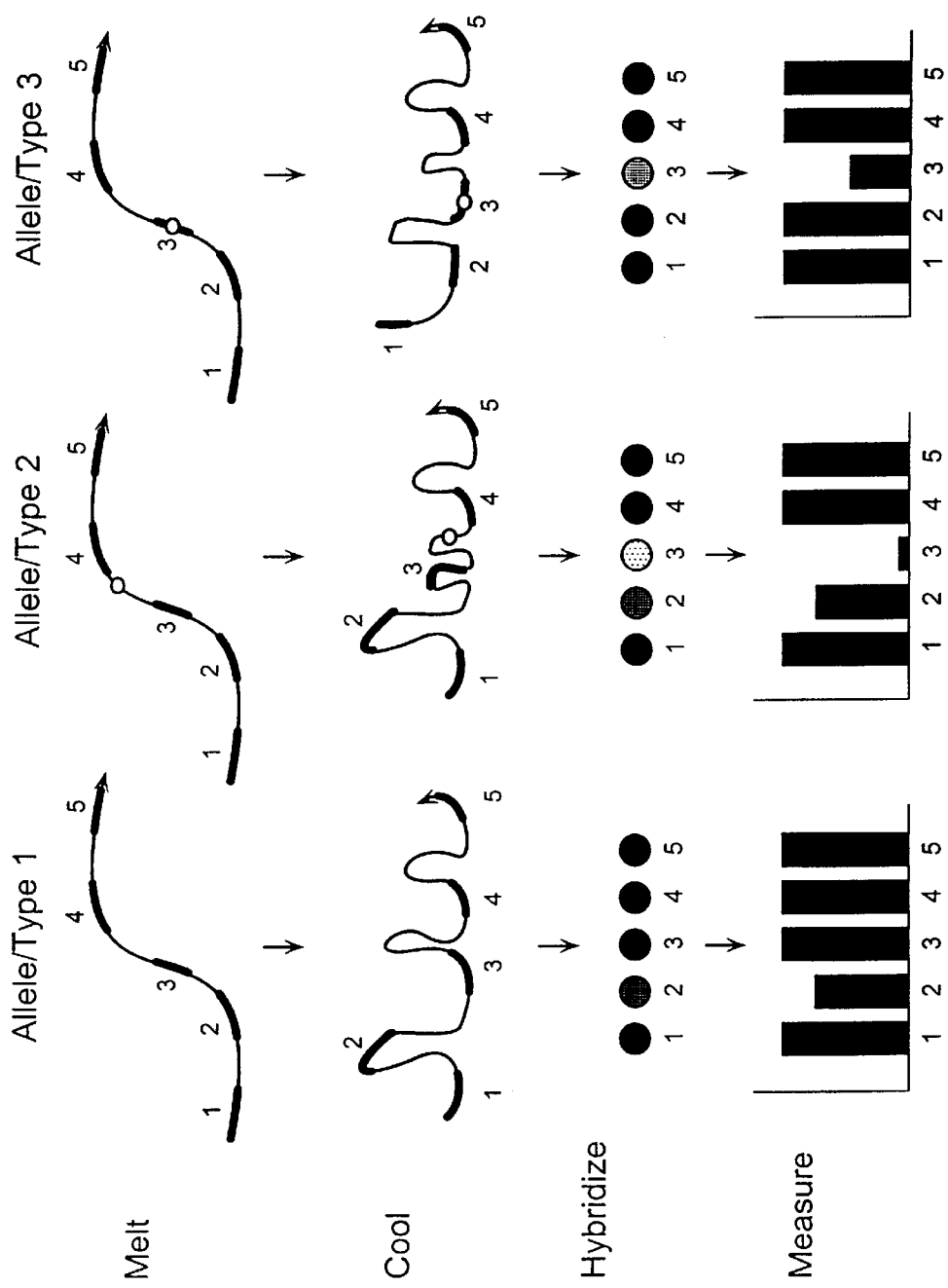
FIG. 1 provides a schematic of one embodiment of the detection methods of the present invention.

To facilitate understanding of the invention, a number of terms are defined below.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "LTR" as used herein refers to the long terminal repeat found at each end of a provirus (i.e., the integrated form of a retrovirus). The LTR contains numerous regulatory signals including transcriptional control elements, polyadenylation signals and sequences needed for replication and integration of the viral genome. The viral LTR is divided into three regions called U3, R and U5.

The U3 region contains the enhancer and promoter elements. The U5 region contains the polyadenylation signals. The R (repeat) region separates the U3 and U5 regions and transcribed sequences of the R region appear at both the 5' and 3' ends of the viral RNA.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be the to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology. Nonetheless, a number of problems have prevented the wide scale use of hybridization as a tool in human diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes (See Wallace et al., Biochimie 67:755 [1985]). In the case of radioactive oligonucleotide probes, only extremely high specific activities are found to show satisfactory results (See Studencki and Wallace, DNA 3:1 [1984]; and Studencki et al., Human Genetics 37:42 [1985]).

With regard to complementarity, it is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

Unless combined with other techniques (such as restriction enzyme analysis), methods that allow for the same level of hybridization in the case of both partial as well as complete complementarity are typically unsuited for such applications; the probe will hybridize to both the normal and variant target sequence. Hybridization, regardless of the method used, requires some degree of complementarity between the sequence being assayed (the target sequence) and the fragment of DNA used to perform the test (the probe). (Of course, one can obtain binding without any complementarity but this binding is nonspecific and to be avoided.)

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The stability of a nucleic acid duplex is measured by the melting temperature, or "$T_m$." The $T_m$ of a particular nucleic acid duplex under specified conditions is the temperature at which on average half of the base pairs have disassociated.

The term "probe" as used herein refers to an oligonucleotide which forms a duplex structure or other complex with a sequence in another nucleic acid, due to complementarity or other means of reproducible attractive interaction, of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "target nucleic acid" and nucleic acid substrate" are used herein interchangeably and refer to a nucleic acid molecule which when denatured and allowed to renature (i.e., to fold upon itself by the formation of intra-strand hydrogen bonds), forms at least one folded structure. The nucleic acid target may comprise single- or double-stranded DNA or RNA.

As used herein, the term "folded target" refers to a nucleic acid strand that contains at least one region of secondary structure (i.e., at least one double stranded region and at least one single-stranded region within a single strand of the nucleic acid). A folded target may comprise regions of tertiary structure in addition to regions of secondary structure.

The term "substantially single-stranded" when used in reference to a nucleic acid target means that the target molecule exists primarily as a single strand of nucleic acid in contrast to a double-stranded target which exists as two strands of nucleic acid which are held together by interstrand base pairing interactions.

Nucleic acids form secondary structures which depend on base-pairing for stability. When single strands of nucleic acids (single-stranded DNA, denatured double-stranded DNA or RNA) with different sequences, even closely related ones, are allowed to fold on themselves, they assume characteristic secondary structures. An alteration in the sequence of the target may cause the destruction of a duplex region(s), or an increase in stability of a thereby altering the accessibility of some regions to hybridization of the probes oligonucleotides. While not being limited to any particular theory, it is thought that individual molecules in the target population may each assume only one or a few of the structures (i.e., duplexed regions), but when the sample is analyzed as a whole, a composite pattern from the hybridization of the probes can be created. Many of the structures that can alter the binding of the probes are likely to be only a few base-pairs long and would appear to be unstable. Some of these structures may be displaced by the hybridization of a probe in that region; others may by stabilized by the hybridization of a probe nearby, such that the probe/substrate duplex can stack coaxially with the target intrastrand duplex, thereby increasing the stability of both. The formation or disruption of these structures in response to small sequence changes results in changes in the patterns of probe/target complex formation. Temperatures in the range of 20 to 55° C., with the range of 20 to 40° C. being particularly preferred, are suitable temperatures for the practice of the method of the invention.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are the to vary in sequence from one another. A second mutant form of the structural gene may exits. This second mutant form is the to vary in sequence from both the wild-type gene and the first mutant form of the gene. It is noted, however, that the invention does not require that a comparison be made between one or more forms of a gene to detect sequence variations. Because the method of the invention generates a characteristic and reproducible pattern of complex formation for a given nucleic acid target, a characteristic "fingerprint" may be obtained from any nucleic target without reference to a wild-type or other control. The invention contemplates the use of the method for both "fingerprinting" nucleic acids without reference to a control and identification of mutant forms of a target nucleic acid by comparison of the mutant form of the target with a wild-type or known mutant control.

The terms "structure probing signature," "hybridization signature" and "hybridization profile" are used interchangeably herein to indicate the measured level of complex formation between a folded target nucleic acid and a probe or set of probes, such measured levels being characteristic of the folded target nucleic acid when compared to levels of complex formation involving reference targets or probes.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to targets present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is the to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "multi-drug resistant" or "multiple-drug resistant" refers to a microorganism which is resistant to more than one of the antibiotics or antimicrobial agents used in the treatment of the microorganism.

The term "non-contiguous," when used to describe regions within a target nucleic acid to be analyzed, is intended to mean that the regions are separated by intervening nucleic acid (or non-nucleic acid spacers). It is not intended that the present invention be limited by the size of the intervening nucleic acid (or the size of non-nucleic acid spacers). However, in preferred embodiments, the intervening sequence is at least five nucleotides in length.

The term "non-contiguous," when used to describe regions within a nucleic acid probe, means sequences capable of hybridizing to the non-contiguous regions of target nucleic acid. It is not intended that the present invention be limited to probes having intervening nucleic acid; that is to say, the non-contiguous regions of a probe are defined functionally, with reference to their binding to non-contiguous regions in a target, the target having intervening nucleic acid separating the non-contiguous regions. Nonetheless, the probes of the present invention may have (but need not have) intervening nucleic acid (or a non-nucleic acid spacer).

The terms "intervening nucleic acid," "intervening portion," "intervening region," "intervening nucleic acid sequence," and "intervening sequence," refer to nucleic acid (single-stranded or double-stranded), that separates two or more regions (e.g., non-contiguous regions) within a nucleic acid sequence. Where the present invention employs a probe having one or more intervening sequences, such intervening sequences are to be distinguished from mere single base mismatched nucleic acid, such that intervening sequences on the probe are at least two nucleic acids in length.

DESCRIPTION OF THE INVENTION

The methods of the present invention use the combined effects of mismatch and folded structure on hybridization to provide a tool for the detection of mutations and other polymorphisms in nucleic acids (e.g., DNA and RNA). The simultaneous probing of the primary (sequence), secondary (simple folded) and tertiary (interactions between secondary folds) structures of substrate molecules is referred herein simply as "structure probing." Rather than destroying secondary structures by high stringency conditions and target fragmentation, the methods of the present invention use conditions in which the formation of intramolecular structures is favored, i.e., unfragmented target strands in conditions of low stringency. Thus, the present method of probing is designed to detect variations between nucleic acids at any of these levels in a single assay.

At temperatures below the melting range of duplexed nucleic acid (i.e., below the melting temperature of long [i.e., >100 bp] nucleic acids; this is generally taken to be temperatures below about 85° C. for a nucleic acid of average G-C content), single-stranded nucleic acids undergo a complex process of intramolecular folding. The first rapid step of this process involves formation of short-range, or local stem-loops structures. Later in the folding process, formation of tertiary or global structure occurs as a result of interactions between different local domains (Zarrinkar and Williamson, Science 265:928 [1994] and Zarrinkar and Williamson, Nat. Struct. Biol., 3:432 [1996]). The effects of secondary structure of the target on probe binding is well documented for DNA and RNA molecules (Gamper et al., supra; Fedorova et al., FEBS Lett. 302:47 [1992]; Lima et al., Biochem., 31:12055 [1992]; Godard et al., Nucl. Acids Res., 22:4789 [1994]; Zarrinkar and Williamson, [1994], supra; Parldhurst and Parkhurst, Biochem., 34:285 [1995]; and Schwille et al., Biochem., 35:10182 [1996]). Target sequences that form stable duplexes within intramolecular secondary structures can have probe binding constants $10^5$–$10^6$ times lower than sequences that exists as a single strands (Lima et al., supra). The reduction of the hybridization constant for structured regions is primarily due to a lower association rate constant rather than a higher dissociation rate constant (Lima et al., supra; Gamper et al., supra and Parkhurst and Parkhurst, supra), supporting the model that the structures in the target are blocking access of the probe to the complementary region within the target molecule.

Mutations in the target sequence change both local and global conformations of the molecule. It has been shown that the conformations assumed by single strands of nucleic acids can be probed using a structure-specific nuclease that cleaves in response to the structures that are formed in a number of test reaction conditions. (Brow et al., supra). Such cleavage creates a collection of product fragments that reflect those structures and which are characteristic of the particular strands. The structures that give rise to cleavage patterns are very sensitive to the precise nucleotide sequence of the strand, such that even single base differences in nucleic acids that are several hundred nucleotides long create sufficient changes in the folded conformations to be detectable in the resulting cleavage pattern (Brow et al., supra), and the changes in electrophoretic mobility in SSCP. As a result of these changes, some regions that were previously base paired may become unpaired and vice versa. By measuring probe hybridization rates it is possible to determine whether or not any region of a target molecule forms intramolecular structure. The examples below describe the use of multiple oligonucleotides to characterize DNA fragments (i.e., for structure probing). This approach is diagrammed schematically in FIG. 1.

In FIG. 1, three different, but related, target nucleic acids are analyzed using the structure probing assay of the present invention. Allele/Type 1 represents the prototypical target sequence (e.g., a wild type allele of gene X); Allele/Types 2 and 3 represent different alleles of the same target sequence (e.g., two different allelic variants of gene X). The thick regions labelled 1–5 along the three target nucleic acids represent the regions along the target that are complementary to probes 1–5. Allele/Type 2 contains a single-base variant (e.g., a point mutation) relative to Allele/Type 1 (represented by the small open circle between regions 3 and 4 of Allele/Type 2). This variant does not appear in a region where a probe binds to the Type 2 target; however, this variant alters the secondary structure of the Type 2 molecule relative to that of the Type 1 molecule such that region 3 of the Type 2 molecule is essentially unavailable for hybridization with probe 3. Allele/Type 3 also contains a single-base variant (e.g., a point mutation) relative to Allele/Type 1 (represented by the small open circle within region 3 of Allele/Type 3). The variant in this molecule is located within a probe binding region and reduces the efficiency with which probe 3 binds to the Type 3 molecule. The target nucleic acids are rendered substantially single-stranded (i.e., they are denatured, e.g., by heating) and then permitted to form secondary structures (e.g., by cooling) and then hybridized with probes 1–5. The probe/target complexes are captured onto a solid support and the amount of target that binds to each of probes 1–5 is determined for each target to generate a probe structure signature (also referred to as a hybridization signature or profile). The schematic shown in FIG. 1 is intended to illustrate that the signal variation may come from probe/target mismatch, or from the formation of local structures that block probe binding sites (i.e., regions on the target which are at least partially complementary to the probe). Tertiary structure, involving interactions between sequences at some distance (even several hundred nucleotides) may also block binding, i.e., mutations at one site may influence probe binding hundreds of nucleotides away, as is seen with the katG targets employed in Example 1.

In the Examples below, the oligonucleotide probes include a biotin moiety so that the labeled target DNAs that have formed a hybridization complex with the probes can be captured by exposure to a solid support coated with streptavidin. When used for immobilization in this way, the probes are referred to herein as "capture probes." The labels on the DNA can then be detected, with the amount of captured DNA reflecting the efficiency of the probe/target hybridization, and thus the strength of a particular binding interaction.

In the Examples below, the solid support employed is a well of a 96-well microtiter plate. This format was chosen for convenience; the methods of the present invention are not limited to the use of microtiter plates or any particular support. The present invention contemplates the use of many types of solid supports, including but not limited to beads, particles, dipsticks, membranes and silicon or glass flat surfaces. It is also contemplated that the binding of the probe/target complexes to surfaces may be through interactions with the target nucleic acid (e.g., the use of biotinylated target nucleic acids), while a detectable label may be included on the probes.

In the embodiments presented herein, the affinity of the target nucleic acid (e.g., a DNA fragment of interest) for different probes is assessed by performing separate hybridization and solid support capture determinations for each probe sequence. It is envisioned that differently labeled probes, e.g., with different fluorescent dyes or other detectable moieties, may be used together in a single complex formation reaction. Use of an instrument that can detect several types of signal, such as a fluorimeter with the capacity to excite and detect at a variety of wavelengths, allows the signal contribution from each of the bound probes to be assessed.

In some typing applications, variants may have any one of several sequences (and therefore structures) and still be classed as the same type (e.g., in HCV, there are numerous sequence variants that are classed as type 1b). If it is not necessary to separately identify the subtypes within a type, a mixture of probes may be provided such that at least one type of probe will interact with each of the different known variants. If the target interacts appropriately (i.e., with the expected affinity) with any probe in the mixture it can be deduced to be of a broad type without concern about the identity of the particular subtype variant. In this way, genetic materials known to vary in sequence without affecting function or type (as do many rapidly changing pathogens) may be analyzed in a single assay without the need for a complex matrix of probes or for sequence determination.

In the following discussion, the oligonucleotide probes are discussed as capture probes. The use of this term is for convenience only, to avoid repetition of the enumeration of the possible configurations for this method, and it is intended that each of the embodiments described below may be used in combination with any of the probe/target configurations (e.g., labeled probes and captured target DNA and vice versa) described above.

The probes used in the methods of the present invention may be used without any prior analysis of the structure assumed by a target nucleic acid. In designing such an assay, one designs probes that would span the entire length of the target sequence, (i.e., they would be complementary to regions of the target that are substantially evenly spaced across the entire length of the target). Probes designed in this way may be phased to a variety of densities. For example, the probes may each shift in hybridization site by one or a few nucleotides, to give a very high resolution fingerprint of the target, or they may be designed to hybridize to adjacent but not overlapping regions, to give thorough coverage at a slightly lower resolution. Alternatively, they may be spaced at much larger intervals for a lower resolution screen. The choice of spacing will be dependent on the needs of the assay. A higher density fingerprint will have a greater likelihood of identifying any possible polymorphism, and may be more suitable for situations where certainty in identification of single base changes is required (e.g., identification of mutations associated with cancers and other diseases). When genotyping is to be performed on targets in which more variation is expected (e.g., rapidly changing viruses), a lower density array may be sufficient for accurate identification. The examples below provide such an analysis for the identification of Hepatitis C viral types. For any given case, it can be determined empirically using appropriately selected reference target molecule whether a chosen probe or array of probes can distinguish between genetic variants sufficiently for the needs of a particular assay. Once a probe or array of probes is selected, the analysis of which probes bind to a target, and how efficiently these probes bind (i.e., how much of probe/target complex can be detected) allows a hybridization signature of the conformation of the target to be created. One possible format for such a signature is as a graph of the measured amounts of a complex formed between the target and each probe, as shown in FIGS. 4, 7, 8, and 9. It is not intended that the structure probing or hybridization signature be limited to the use of the column graphs shown in these figures. It is contemplated that the signature may be stored, represented or analyzed by any of the methods commonly used for the presentation of mathematical and physical information, including but not limited to line, pie, or area graphs or 3-dimensional topographic representations. The data may also be used as a numerical matrix, or any other format that may be analyzed either visually, mathematically or by computer-assisted algorithms.

The resulting signatures of the nucleic acid structures serve as sequence-specific identifiers of the particular molecule, without requiring the determination of the actual nucleotide sequence. While specific sequences may be identified by comparison of their signature to a reference signature, the use of algorithms to deduce the actual sequence of a molecule by sequence-specific hybridization (i.e., at high stringency to eliminate the influence of secondary and tertiary structures) to a complete matrix (i.e., probes that shift by a single nucleotide position at each location of an array), is not a feature or requirement, or within the bounds of the methods of the present invention.

It is contemplated that information on the structures assumed by a target nucleic acid may be used in the design of the probes, such that regions that are known or suspected to be involved in folding may be chosen as hybridization sites. Such an approach will reduce the number of probes that are likely to be needed to distinguish between targets of interest.

There are many methods used to obtain structural information involving nucleic acids, including the use of chemicals that are sensitive to the nucleic acid structure, such as phenanthroline/copper, EDTA-$Fe^{2+}$, cisplatin, ethylnitrosourea, dimethyl pyrocarbonate, hydrazine, dimethyl sulfate, and bisulfite. Enzymatic probing using structure-specific nucleases from a variety of sources, such as the Cleavase® enzymes (Third Wave Technologies, Inc., Madison, Wis.), Taq DNA polymerase, *E. coli* DNA polymerase I, and eukaryotic structure-specific endonucleases (e.g., human, murine and Xenopus XPG enzymes, yeast RAD2 enzymes), murine FEN-1 endonucleases (Harrington and Lieber, Genes and Develop., 3:1344 [1994]) and calf thymus 5' to 3' exonuclease (Murante et al., J. Biol. Chem., 269:1191 [1994]). In addition, enzymes having 3' nuclease activity such as members of the family of DNA repair endonucleases (e.g., the RrpI enzyme from *Drosophila melanogaster*, the yeast RAD1/RAD10 complex and *E. coli* Exo III), are also suitable for examining the structures of nucleic acids. In Example 3, the use of the CFLP® method for identifying regions of folding in PCR amplified segments of the HCV genome is described.

If analysis of structure as a step in probe selection is to be used for a segment of nucleic acid for which no information is available concerning regions likely to form secondary structures, the sites of structure-induced modification or cleavage must be identified. It is most convenient if the modification or cleavage can be done under partially reactive conditions (i.e., such that in the population of molecules in a test sample, each individual will receive only one or a few cuts or modifications). When the sample is analyzed as a whole, each reactive site should be represented, and all the sites may be thus identified. Using a CFLP® cleavage reaction as an example, when the partial cleavage products of an end labeled nucleic acid fragment are resolved by size (e.g., by electrophoresis), the result is a ladder of bands indicating the site of each cleavage, measured from the labeled end. Similar analysis can be done for chemical modifications that block DNA synthesis; extension of a primer on molecules that have been partially modified will yield a nested set of termination products. Determining the sites of cleavage/modification may be done with some degree of accuracy by comparing the products to size markers (e.g., commercially available fragments of DNA for size comparison) but a more accurate measure is to create a DNA sequencing ladder for the same segment of nucleic acid to resolve alongside the test sample. This allows rapid identification of the precise site of cleavage or modification.

To distinguish between related nucleic acids, the regions that show different sites of cleavage or modification have the highest probability of having secondary structures that will respond differently to probes in the methods of the present invention. This is for two reasons. First, the cleavage or modification is physical evidence that a structure may form at a given site under the conditions of the cleavage or modification assay. Second, the structures that are detected by the CFLP® method have been found to be predominantly local (i.e., formed from sequences that are close to each other along the nucleic acid strand, Brow et al, supra), so that changes observed are likely to be caused by base changes near the altered cleavage site. By designing oligonucleotide probes to hybridize or complex with the regions showing different sites of cleavage or modification there is a higher probability of finding either a base change (primary structure variation) or a folding change (secondary structure variation) that will affect the complexing of the probe to that site, thus facilitating the distinction between the comparison targets. Because of the complex nature of the folded structure formation as described above and because any given probe may interact with the target in a number of ways, choosing a probe in this way is not a guarantee that any particular probe will provide a diagnostic distinction. This is offered as a guide to increase the probability that it will. When working with an uncharacterized target or set of targets, the use of a multiplicity of such probes will give the most distinctive signature of probe/target complex formation.

It is preferred that the probes used in the methods of the present invention be short enough to provide distinctive hybridization signatures for variants of a target. Probes longer than about 20 nt (e.g., 20 to 40 nt) can interact with target nucleic acids in a specific maimer at elevated temperatures (e.g., higher than about 40° C.) and thus are suitable for use in the present methods. However, probes in this size range may interact with multiple sites on the target if the reaction is performed below about 40° C., reducing the distinction between variants. If this is the case, higher reaction temperatures or more stringent solution conditions (e.g., lower salt, the inclusion of helix-destabilizing agents such as dimethyl sulfoxide or formamide) may prove useful in enhancing the distinction between targets. In a particularly preferred embodiment, the method of the present invention is performed at ambient temperatures (e.g., 20 to 25° C.). When the assay is performed at room temperature, small probes with $T_m$s of 40° C. or less (e.g., 10 to 20 nt) can provide the discrimination necessary, as shown in the examples below. Probes in this size range are also less likely to fold on themselves under the reaction conditions, an effect that would reduce the binding efficacy of a probe without regard to the structure of the target.

As stated above, the capture probe may interact with the target in any number of ways. For example, in another embodiment, the capture probes may contact more than one region of the target nucleic acid. When the target nucleic acid is folded as described, two or more of the regions that remain single stranded may be sufficiently proximal to allow contact with a single capture probe. The capture oligonucleotide in such a configuration is referred to herein as a "bridge" or "bridging" oligonucleotide, to reflect the fact that it may interact with distal regions within the target nucleic acid. The use of the terms "bridge" and "bridging" is not intended to limit these distal interactions to any particular type of interaction. It is contemplated that these interactions may include non-standard nucleic acid interactions known in the art, such as G-T base pairs, Hoogstein interactions, triplex structures, quadraplex aggregates, and the multibase hydrogen bonding such as is observed within nucleic acid tertiary structures, such as those found in tRNAs. The terms are also not intended to indicate any particular spatial orientation of the regions of interaction on the target strand, i.e., it is not intended that the order of the contact regions in a bridge oligonucleotide be required to be in the same sequential order as the corresponding contact regions in the target strand. The order may be inverted or otherwise shuffled.

It is known that synthetic oligonucleotides can be hybridized to non-contiguous sequences in both RNA and DNA strands, in a manner that either causes the intervening sequence to loop out, or that bridges the base of an internal folded structure (Richardson et al., J. Am. Chem. Soc., 113:5109 [1991]; Francois et al., Nucl. Acid. Res., 22: 3943 [1994]). However, these references do not suggest the design or use of bridging oligonucleotides that can distinguish between the different folded structures, or that bind with significantly reduced efficiency when the intervening sequence is unstructured. The present invention provides methods for the use and design of bridge capture probes with minimally stable regions of complementarity to make these bridge probes sensitive to changes in the target strand structure. Minimal stability (i.e., with a very low melting temperature), may be created in a number of ways, including by the use of short lengths of complementarity, low G-C basepair content, and/or the use of base analogs or mismatches to reduce the melting temperature. To test the effects of variations in the target structure on the efficiency of capture with different lengths of bridge probes, three test molecules were created; these are shown in schematic representation in FIG. 10. Test molecule #80 (SEQ ID NO:39) has a long segment of self complementarity and when folded as shown, the 8 basepair hairpin formed by this oligonucleotide is further stabilized by a "tri-loop" sequence in the loop end (i.e., three nucleotides form the loop portion of the hairpin) (Hiraro et al., Nucleic Acids Res. 22(4):576 [1994]). In test molecule #81 (SEQ ID NO:40), the stem is interrupted by 2 mismatches to form a less stable structure, and the region of self-complementarity is entirely removed in test molecule #82 (SEQ ID NO:41). All three of these molecules have identical target regions for the binding of the capture oligonucleotides, and an examination of their use is described in Example 6.

When a bridging oligonucleotide contacts sequences on either side of a basepaired stem, the structure formed is termed a three-way or three-arm junction. Such junctions have been studied extensively to determine their physical structure and to assess the differences that occur in the physical structure when additional nucleotides are included in these structures. When extra nucleotides are included at the junction site, where the three strands come together (i.e., when a 'bulged' structure is formed), it has been shown that the structure is more flexible and that some degree of coaxial stacking between the arms stabilized the structure compared to the unbulged structure (See e.g., Zhong et al., Biochem., 32:6898 [1993]; and Yang et al., Biochem., 35:7959 [1996]). The inclusion of two thymidine nucleotides in the portion of the probe that forms the junction is particularly preferred.

There are a number of approaches that may be used in the design or selection of bridging capture probes. For simplicity of discussion and to avoid repetition, this section describes one embodiment of the present invention, namely a process for creating bridge oligonucleotides that interact with only two regions of a target nucleic acid. It is not intended, however, that the invention be limited to the use of oligonucleotides that have only two sites of interaction. It is contemplated that bridge oligonucleotides may be created that can interact with many sites on a folded target molecule.

Bridge oligonucleotides may be created by the joining two or more short oligonucleotide sequences. The creation of bridge oligonucleotides may be based upon observations that these sequences have been determined to interact with a given folded target when used in isolation, without limitation to any particular nature of interaction, or they may be deduced to be capable of such interaction by virtue of sequence composition, complementarity, or like analysis. For convenience, such sequences are termed herein "contact sequences," to reflect the putative ability of such a sequence to contact the target molecule. The designation of a particular sequence as a contact sequence is not intended to imply that the sequence is in contact, or is required to contact a target in any particular embodiment.

In alternative embodiments, contact sequences may be joined by synthesizing or otherwise creating a new oligonucleotide that incorporates both sequences into a single molecule. In one embodiment, the sequences are joined contiguously within the bridge oligonucleotide (i.e., without any intervening nucleotides or other space-filling material). In another embodiment, the contact sequences are non-contiguous, with the spacing provided by additional nucleotides. In a preferred embodiment, the contact sequences are bridged by two thymidine nucleotides, as depicted in several of the bridging probes in FIG. 11A. In another preferred embodiment, the contact sequences in the bridging oligonucleotide are connected by a segment of nucleic acid containing a region of self-complementarity, such that the bridging oligonucleotide itself contains a folded structure. A stem-loop folded structure within the bridge oligonucleotide, if situated opposite a stem in the target nucleic acid, would permit the formation of a four-way Holliday structure, which is stabilized by coaxial stacking of the arms (Duckett et al., Cell 55:79 [1988]).

Alternatively, the bridge oligonucleotide may be created by linking the individual sequences with non-nucleotide spacers such as those commonly known in the art, such as d-spacers (Glen Research Corp. (Sterling, Va.), or other chemical chains, such as polyethers (Cload and Shephartz, J. Am. Chem. Soc., 11 3:6324[1991]).

Contact sequences may also be linked to form the bridge probes post synthetically, by enzymatic (e.g., ligation) or by chemical interaction to produce either covalent (e.g., cross-linked) or non-covalent bonds (e.g., affinity bonds such as formed in an antigen-antibody interaction).

The formation of the complexes between the probes and the targets may be performed using a wide variety of solution conditions. Conditions considered to be "low stringency" have been well defined in the areas of hybridization to filters and membranes (Sambrook et al, *Molecular Cloning: A Laboratory Manual*, 2nd ed. Cold Spring Harbor Laboratory Press, Cold Spring Harbor, N.Y. [1989]) and to other solid supports, such as silicon or glass wafers, chips or slides (Maskos and Southern, Nucl. Acids Res., 20:1675 [1992]). It is contemplated that the formation of the complexes may be done in solution, before the binding of either the target or the probe to a solid support, or it may be done after one of the molecules has been bound to the support. It is recognized, and considered to be within the scope of the invention, that the kinetics and mechanics of complex formation may differ depending on whether complex formation is performed in solution or on a solid support. The identity of the support would also be expected to influence the complex formation. However, as long as complexes can be made to form at detectable levels, a set of conditions is considered appropriate for use in the present methods.

A number of solid supports known in the art are contemplated for use with the methods of the present invention. In the examples below, a 96-well microtiter plate is used as a support medium. The method may also be applied to other supports nucleic acid commonly used for nucleic acid analyses, including but not limited to beads, particles, membranes, filters, dipsticks, slides, plates and microchips. Such supports may be composed of a number of materials known to be compatible with nucleic acids analyses, including but not limited to agarose, styrene, nylon, glass and silicon.

Individual complex formation (i.e., assessing a single target with a single probe) may be sufficiently informative for some applications. In other applications, it may be desirable to use a number of probes against a single target. For a large number of probes, it may be useful to use an array format, in which a large number of probes are bound to a surface in an ordered pattern. Means for creating such arrays on surfaces such as glass slides and microchips are known in the art (Southern, Maskos, and Elder, Genomics 13:1008 [1992]; Chee et al., Science 274:610 [1996]; and Foder et al., Science 251:767 [1991]; and U.S. Pat. No. 5,436,327 to Southern et al., U.S. Pat. No. 5,429,807 to Matson et al. and U.S. Pat. No. 5,599,695 to Pease et al., all of which are herein incorporated by reference).

Specific applications of the structure probing methods of the present invention are described below.

A. Detection and Identification of Pathogens Using the Structure Probing Method

1. Detection and Identification of Multi-Drug Resistant *M. tuberculosis*

In the past decade there has been a tremendous resurgence in the incidence of tuberculosis in this country and throughout the world. In the United States, the incidence of tuberculosis has risen steadily during past decade, accounting for 2000 deaths annually, with as many as 10 million Americans infected with the disease. The situation is critical in New York City, where the incidence has more than doubled in the past decade, accounting for 14% of all new cases in the United States in 1990 (Frieden et al., New Engl. J. Med., 328:521 [1993]).

The crisis in New York City is particularly dire because a significant proportion (as many as one-third) of the recent cases are resistant to one or more anti-tuberculosis drugs (Frieden et al,supra and Hughes, Scrip Magazine May [1994]). Multi-drug resistant tuberculosis (MDR-TB) is an iatrogenic disease that arises from incomplete treatment of a primary infection (Jacobs, Jr., Clin. Infect. Dis., 19:1 [1994]). MDR-TB appears to pose an especially serious risk to the immunocompromised, who are more likely to be infected with MDR-TB strains than are otherwise healthy individuals [Jacobs, Jr., supra]. The mortality rate of MDR-TB in immunocompromised individuals is alarmingly high, often exceeding 90%, compared to a mortality rate of <50% in otherwise uncompromised individuals (Donnabella et al., Am. J. Respir. Dis., 11:639 [1994]).

From a clinical standpoint, tuberculosis has always been difficult to diagnose because of the extremely long generation time of *Mycobacterium tuberculosis* as well as the environmental prevalence of other, faster growing mycobacterial species. The doubling time of *M. tuberculosis* is 20–24 hours, and growth by conventional methods typically requires 4 to 6 weeks to positively identify *M. tuberculosis* (Jacobs, Jr. et al., Science 260:819 [1993] and Shinnick and Jones in *Tuberculosis: Pathogenesis, Protection and Control*, Bloom, ed., American Society of Microbiology, Washington, D.C. [1994], pp. 517–530). It can take an additional 3 to 6 weeks to diagnose the drug susceptibility of a given strain (Shinnick and Jones, supra). Needless to say, the health risks to the infected individual, as well as to the public, during a protracted period in which the patient may or may not be symptomatic, but is almost certainly contagious, are considerable. Once a drug resistance profile has been elucidated and a diagnosis made, treatment of a single patient can cost up to $250,000 and require 24 months.

The recent explosion in the incidence of the disease, together with the dire risks posed by MDR strains, have combined to spur a burst of research activity and commercial development of procedures and products aimed at accelerating the detection of *M. tuberculosis* as well the elucidation of drug resistance profiles of *M. tuberculosis* clinical isolates. A number of these methods are devoted primarily to the task of determining whether a given strain is *M. tuberculosis* or a mycobacterial species other than tuberculosis. Both culture based methods and nucleic-acid based methods have been developed that allow *M. tuberculosis* to be positively identified more rapidly than by classical methods: detection times have been reduced from greater than 6 weeks to as little as two weeks (culture-based methods) or two days (nucleic acid-based methods). While culture-based methods are currently in wide-spread use in clinical laboratories, a number of rapid nucleic acid-based methods that can be applied directly to clinical samples are under development. For all of the techniques described below, it is necessary to first "decontaminate" the clinical samples, such as sputum (usually done by pretreatment with N-acetyl L-cysteine and NaOH) to reduce contamination by non-mycobacterial species (Shinnick and Jones, supra).

The polymerase chain reaction (PCR) has been applied to the detection of *M. tuberculosis* and can be used to detect its presence directly from clinical specimens within one to two days. The more sensitive techniques rely on a two-step procedure: the first step is the PCR amplification itself, the second is an analytical step such as hybridization of the amplicon to a *M. tuberculosis*-specific oligonucleotide probe, or analysis by RFLP or DNA sequencing [Shinnick and Jones, supra].

The Amplified *M. tuberculosis* Direct Test (AMTDT; Gen-Probe) relies on Transcription Mediated Amplification (TMA; essentially a self-sustained sequence reaction [3SR] amplification) to amplify target rRNA sequences directly from clinical specimens. Once the rRNA has been amplified, it is then detected by a dye-labeled assay such as the PACE2. This assay is highly subject to inhibition by substances present in clinical samples.

The Cycling Probe Reaction (CPR; ID Biomedical). This technique, which is under development as a diagnostic tool for detecting the presence of *M. tuberculosis*, measures the accumulation of signal probe molecules. The signal amplification is accomplished by hybridizing tripartite DNA-RNA-DNA probes to target nucleic acids, such as *M. tuberculosis*-specific sequences. Upon the addition of RNAse H, the RNA portion of the chimeric probe is degraded, releasing the DNA portions, which accumulate linearly over time to indicate that the target sequence is present (Yule, Bio/Technol., 12:1335 [1994]). The need to use of RNA probes is a drawback, particularly for use in crude clinical samples, where RNase contamination is often rampant.

The above nucleic acid-based detection and differentiation methods offer a clear time savings over the more traditional, culture-based methods. While they are beginning to enter the clinical setting, their usefulness in the routine diagnosis of *M. tuberculosis* is still in question, in large part because of problems with associated with cross-contamination and low-sensitivity relative to culture-based methods. In addition, many of these procedures are limited to analysis of respiratory specimens (Yule, supra).

i) Determination of the Antibiotic Resistance Profile of *M. tuberculosis* a) Culture-based methods: Once a positive identification of *M. tuberculosis* has been made, it is necessary to characterize the extent and nature of the strain's resistance to antibiotics. The traditional method used to determine antibiotic resistance is the direct proportion agar dilution method, in which dilutions of culture are plated on media containing antibiotics and on control media without antibiotics. This method typically adds an additional 2–6 weeks to the time required for diagnosis and characterization of an unknown clinical sample (Jacobs, Jr., supra).

The Luciferase Reporter Mycobacteriophage (LRM) assay was first described in 1993 (Jacobs, Jr. et al. [1993], supra). In this assay, a mycobacteriophage containing a cloned copy of the luciferase gene is used to infect mycobacterial cultures. In the presence of luciferin and ATP, the expressed luciferase produces photons, easily distinguishable by eye or by a luminometer, allowing a precise determination of the extent of mycobacterial growth in the presence of antibiotics. Once sufficient culture has been obtained (usually 10–14 days post-inoculation), the assay can be completed in 2 days. This method suffers from the fact that the LRM are not specific for *M. tuberculosis*: they also infect *M. smegmatis* and *M. bovis* (e.g., BCG), thereby complicating the interpretation of positive results. Discrimination between the two species must be accomplished by growth on specialized media which does not support the growth of *M. tuberculosis* (e.g., NAP media). This confirmation requires another 2 to 4 days.

The above culture-based methods for determining antibiotic resistance will continue to play a role in assessing the effectiveness of putative new anti-mycobacterial agents and those drugs for which a genetic target has not yet been identified. However, recent success in elucidating the molecular basis for resistance to a number of anti-mycobacterial agents, including many of the front-line drugs, has made possible the use of much faster, more accurate and more informative DNA polymorphism-based assays.

b) DNA-based methods: Genetic loci involved in resistance to isoniazid, rifampin, streptomycin, fluoroquinolones, and ethionamide have been identified (Jacobs, Jr., supra; Heym et al., Lancet 344:293 [1994]; and Morris et al., J. Infect. Dis., 171:954 [1995]. A combination of isoniazid (inh) and rifampin (rif) along with pyrazinamide and ethambutol or streptomycin, is routinely used as the first line of attack against confirmed cases of *M. tuberculosis* (Banerjee et al., Science 263:227 [1994]). Consequently, resistance to one or more of these drugs can have disastrous implications for short course chemotherapy treatment. The increasing incidence of such resistant strains necessitates the development of rapid assays to detect them and thereby reduce the expense and community health hazards of pursuing ineffective, and possibly detrimental, treatments. The identification of some of the genetic loci involved in drug resistance has facilitated the adoption of mutation detection technologies for rapid screening of nucleotide changes that result in drug resistance. The availability of amplification procedures such as PCR and SDA, which have been successful in replicating large amounts of target DNA directly from clinical specimens, makes DNA-based approaches to antibiotic profiling far more rapid than conventional, culture-based methods.

The most widely employed techniques in the genetic identification of mutations leading to drug resistance are DNA sequencing, Restriction Fragment Length Polymorphism (RFLP), PCR-Single Stranded Conformational Polymorphism (PCR-SSCP), and PCR-dideoxyfingerprinting (PCR-ddF). All of these techniques have drawbacks as discussed above. None of them offers a rapid, reproducible means of precisely and uniquely identifying individual alleles.

In contrast, the structure probing methods of the present invention provide an approach that relies on interactions of oligonucleotide probes with the target nucleic acid on the primary, secondary and tertiary structure level. This method requires a fraction of the time, skill and expense of the techniques described above, and can be performed using instrumentation commonly found in the clinical lab (e.g., a microtiter plate reader).

The application of this method to the detection of MDR-TB is illustrated herein using segments of DNA amplified from katG gene. Other genes associated with MDR-TB, including but not limited to those involved in conferring resistance to isoniazid (inhA), streptomycin (rpsL and rrs), and fluoroquinoline (gyrA), are equally well suited to the structure probing assay of the present invention.

2. Detection and Identification of Hepatitis C Virus

Hepatitis C virus (HCV) infection is the predominant cause of post-transfusion non-A, non-B (NANB) hepatitis around the world. In addition, HCV is the major etiologic agent of hepatocellular carcinoma (HCC) and chronic liver disease world wide. HCV infection is transmitted primarily to blood transfusion recipients and intravenous drug users although maternal transmission to offspring and transmission to recipients of organ transplants have been reported.

The genome of the positive-stranded RNA hepatitis C virus comprises several regions including 5' and 3' noncoding regions (i.e., 5' and 3' untranslated regions) and a polyprotein coding region which encodes the core protein (C), two envelope glycoproteins (E1 and E2/NS1) and six nonstructural glycoproteins (NS2-NS5b). Molecular biological analysis of the small (9.4 kb) RNA genome has showed that some regions of the genome arc very highly conserved between isolates, while other regions are fairly rapidly changeable. The 5' noncoding region (NCR) is the most highly conserved region in the HCV. These analyses have allowed these viruses to be divided into six basic genotype groups, and then further classified into over a dozen sub-types (the nomenclature and division of HCV genotypes is evolving; See Altamirano et al., J. Infect. Dis., 171:1034 [1995] for a recent classification scheme). These viral groups are associated with different geographical areas, and accurate identification of the agent in outbreaks is important in monitoring the disease. While only Group 1 HCV has been observed in the United States, multiple HCV genotypes have been observed in both Europe and Japan.

The ability to determine the genotype of viral isolates also allows comparisons of the clinical outcomes from infection by the different types of HCV, and from infection by multiple types in a single individual. HCV type has also been associated with differential efficacy of treatment with interferon, with Group 1 infected individuals showing little response (Kanai et al., Lancet 339:1543 [1992] and Yoshioka et al., Hepatol., 16:293 [1992]). Pre-screening of infected individuals for the viral type will allow the clinician to make a more accurate diagnosis, and to avoid costly but fruitless drug treatment.

Existing methods for determining the genotype of HCV isolates include traditional serotyping, PCR amplification of segments of the HCV genome coupled with either DNA sequencing or hybridization to HCV-specific probes and RFLP analysis of PCR amplified HCV DNA. All of these methods suffer from the limitations discussed above (i.e., DNA sequencing is too labor-intensive and expensive to be practical in clinical laboratory settings; RFLP analysis suffers from low sensitivity).

Universal and genotype specific primers have been designed for the amplification of HCV sequences from RNA extracted from plasma or serum (Okamoto et al., J. Gen. Virol., 73:673 [1992]; Yoshioka et al., Hepatol., 16:293 [1992] and Altamirano et al., supra). These primers can be used to generate PCR products which serve as substrates in the structure probing assay of the present invention. As shown herein, the structure probing assay provides a rapid and accurate method of typing HCV isolates. The structure probing analysis of HCV substrates allows a distinction to be made between the major genotypes and subtypes of HCV thus providing improved methods for the genotyping of HCV isolates.

3. Detection and Identification of Bacterial Pathogens

Identification and typing of bacterial pathogens is critical in the clinical management of infectious diseases. Precise identity of a microbe is used not only to differentiate a disease state from a healthy state, but is also fundamental to determining whether and which antibiotics or other antimicrobial therapies are most suitable for treatment. Traditional methods of pathogen typing have used a variety of phenotypic features, including growth characteristics, color, cell or colony morphology, antibiotic susceptibility, staining, smell and reactivity with specific antibodies to identify bacteria. All of these methods require culture of the suspected pathogen, which suffers from a number of serious shortcomings, including high material and labor costs, danger of worker exposure, false positives due to mishandling and false negatives due to low numbers of viable cells or due to the fastidious culture requirements of many pathogens. In addition, culture methods require a relatively long time to achieve diagnosis, and because of the potentially life-threatening nature of such infections, antimicrobial therapy is often started before the results can be obtained. In many cases the pathogens are very similar to the organisms that make up the normal flora, and may be indistinguishable from the innocuous strains by the methods cited above. In these cases, determination of the presence of the pathogenic strain may require the higher resolution afforded by more recently developed molecular typing methods.

A number of methods of examining the genetic material from organisms of interest have been developed. One way of performing this type of analysis is by hybridization of species-specific nucleic acid probes to the DNA or RNA from the organism to be tested. This is done by immobilizing the denatured nucleic acid to be tested on a membrane support, and probing with labeled nucleic acids that will bind only in the presence of the DNA or RNA from the pathogen. In this way, pathogens can be identified. Organisms can be further differentiated by using the RFLP method described above, in which the genomic DNA is digested with one or more restriction enzymes before electrophoretic separation and transfer to a nitrocellulose or nylon membrane support. Probing with the species-specific nucleic acid probes will reveal a banding pattern that, if it shows variation between isolates, can be used as a reproducible way of discriminating between strains. However, these methods are susceptible to the drawbacks outlined above: assays based on sequence-specific hybridization to complex (i.e., whole genome) targets are time-consuming and may give false or misleading results if the stringency of the hybridization is not well controlled, and RFLP identification is dependent on the presence of suitable restriction sites in the DNA to be analyzed.

To address these concerns about hybridization and RFLP as diagnostic tools, several methods of molecular analysis based on polymerase chain reaction (PCR) amplification have gained popularity. In one well-accepted method, called PCR fingerprinting, the size of a fragment generated by PCR is used as an identifier. In this type of assay, the primers are targeted to regions containing variable numbers of tandem repeated sequences (referred to as VNTRs an eukaryotes). The number of repeats, and thus the length of the PCR amplicon, can be characteristic of a given pathogen, and co-amplification of several of these loci in a single reaction can create specific and reproducible fingerprints, allowing discrimination between closely related species.

In some cases where organisms are very closely related, however, the target of the amplification does not display a size difference, and the amplified segment must be further probed to achieve more precise identification. This may be done on a solid support, in a fashion analogous to the whole-genome hybridization described above, but this has the same problem with variable stringency as that assay. Alternatively, the interior of the PCR fragment may be used as a template for a sequence-specific ligation event. As outlined above for the LCR, in this method, single stranded probes to be ligated are positioned along the sequence of interest on either side of an identifying polymorphism, so that the success or failure of the ligation will indicate the presence or absence of a specific nucleotide sequence at that site. With either hybridization or ligation methods of PCR product analysis, knowledge of the precise sequence in the area of probe binding must be obtained in advance, and differences outside the probe binding area are not detected. These methods are poorly suited to the examination and typing of new isolates that have not been fully characterized.

In the methods of the present invention, primers that recognize conserved regions of bacterial ribosomal RNA genes allow amplification of segments of these genes that include sites of variation. The variations in ribosomal gene sequences have become an accepted method not only of differentiating between similar organisms on a DNA sequence level, but their consistent rate of change allows these sequences to be used to evaluate the evolutionary relatedness of organisms. That is to say, the more similar the nucleic acid is at the sequence level, the more closely related the organisms in discussion are considered to be (Woese, Microbiol. Rev., 51:221–271 [1987]). The present invention allows the amplification products derived from these sequences to be used to create highly individual structural fingerprints (e.g., profiles of the complex formation with an array of probes), allowing the detection of sequence polymorphisms without prior knowledge of the site, character or even the presence of the polymorphisms. With appropriate selection of primers, the PCR amplification can be made to be either all-inclusive (e.g., using the most highly conserved ribosomal sequences) to generate PCR products that, when analyzed using the methods of the present invention, allow comparison of distantly related organisms, or the primers can be chosen to be very specific for a given genus, to allow examination at the species and subspecies level. While the examination of ribosomal genes is extremely useful in these characterizations, the use of the structure probing method in bacterial typing is not limited to these genes. Other genes, including but not limited to those associated with specific growth characteristics, (e.g., carbon source preference, antibiotic resistance, resistance to methicillin or antigen production), or with particular cell morphologies (such as pilus formation) are equally well suited to the structure probing assay of the present invention.

B. Extraction of Nucleic Acids from Clinical Samples

To provide nucleic acid substrates for use in the detection and identification of microorganisms in clinical samples using the structure probing assay, nucleic acid is extracted from the sample. The nucleic acid may be extracted from a variety of clinical samples (fresh or frozen tissue, suspensions of cells [e.g., blood], cerebral spinal fluid, sputum, urine, etc.) using a variety of standard techniques or commercially available kits. For example, kits which allow the isolation of RNA or DNA from tissue samples are available from Qiagen, Inc. (Chatsworth, Calif.) and Stratagene (La Jolla, Calif.). For example, the QIAamp Blood kits permit the isolation of DNA from blood (fresh, frozen or dried) as well as bone marrow, body fluids or cell suspensions. QIAamp tissue kits permit the isolation of DNA from tissues such as muscles, organs and tumors.

It has been found that crude extracts from relatively homogenous specimens (such as blood, bacterial colonies, viral plaques, or cerebral spinal fluid) are better suited to severing as templates for the amplification of unique PCR products than are more composite specimens (such as urine, sputum or feces) (Shibata in PCR: *The Polymerase Chain Reaction*, Mullis et al., eds., Birkhauser, Boston [1994], pp. 47–54). Samples which contain relatively few copies of the material to be amplified (i.e., the target nucleic acid), such as cerebral spinal fluid, can be added directly to a PCR. Blood samples have posed a special problem in PCRs due to the inhibitory properties of red blood cells. The red blood cells must be removed prior to the use of blood in a PCR; there are both classical and commercially available methods for this purpose (e.g., QIAamp Blood kits, passage through a Chelex 100 column [BioRad], etc.). Extraction of nucleic acid from sputum, the specimen of choice for the direct detection of *M. tuberculosis*, requires prior decontamination to kill or inhibit the growth of other bacterial species. This decontamination is typically accomplished by treatment of the sample with N-acetyl L-cysteine and NaOH (Shiimick and Jones, supra). This decontamination process is necessary only when the sputum specimen is to be cultured prior to analysis.

EXPERIMENTAL

The following examples serve to illustrate certain preferred embodiments and aspects of the present invention and are not to be construed as limiting the scope thereof.

In the disclosure which follows, the following abbreviations apply: ° C. (degrees Centigrade); g (gravitational field); vol (volume); w/v (weight to volume); v/v (volume to volume); BSA (bovine serum albumin); CTAB (cetyltrimethylammonium bromide); HPLC (high pressure liquid chromatography); DNA (deoxyribonucleic acid); IVS (intervening sequence); p (plasmid); ml (microliters); ml (milliliters); mg (micrograms); pmoles (picomoles); mg (milligrams); MOPS (3-[N-Morpholino]propanesulfonic acid); M (molar); mM (milliMolar); mM (microMolar); nm (nanometers); nt (nucleotide); bp (base pair); kb (kilobase pair); kdal (kilodaltons); OD (optical density); EDTA (ethylene diamine tetra-acetic acid); FITC (fluorescein isothiocyanate); IPTG (isopropylthiogalactoside); X-Gal (5-bromo-4-chloro-3-indolyl-β-D-galactosidase); SDS (sodium dodecyl sulfate); NaPO$_4$ (sodium phosphate); Tris (tris(hydroxymethyl)-aminomethane); PMSF (phenylmethyl-sulfonylfluoride); TBE (Tris-Borate-EDTA, i.e., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); Tween (polyoxyethylene-sorbitan); Boehringer Mannheim (Boehringer Mannheim, Indianapolis, Ind.); Dynal (Dynal A. S., Oslo, Norway); Epicentre (Epicentre Technologies, Madison, Wis.); MJ Research (MJ Research, Inc., Watertown, Mass.); National Biosciences (National Biosciences, Plymouth, Minn.); New England Biolabs (New England Biolabs, Beverly, Mass.); Novagen (Novagen, Inc., Madison, Wis.); Perkin Elmer (Perkin Elmer, Norwalk, Conn.); Promega Corp. (Promega Corp., Madison, Wis.); Stratagene (Stratagene Cloning Systems, La Jolla, Calif.); Third Wave (Third Wave Technologies, Inc., Madison, Wis.); and USB (U.S. Biochemical, Cleveland, Ohio).

20×SSPE (sodium chloride, sodium phosphate, EDTA) contains per liter: 174 grams NaCl, 27.6 grams NaH$_2$PO$_4$.H$_2$O and 7.4 grams EDTA; the pH is adjusted to 7.4 with NaOH. PBS (phosphate-buffered saline) contains per liter: 8 grams NaCl, 0.2 grams KCl, 1.44 grams Na$_2$PO$_4$ and 0.24 grams KH$_2$PO$_4$; the pH is adjusted to 7.4 with HCl.

EXAMPLE 1

Figure 2:
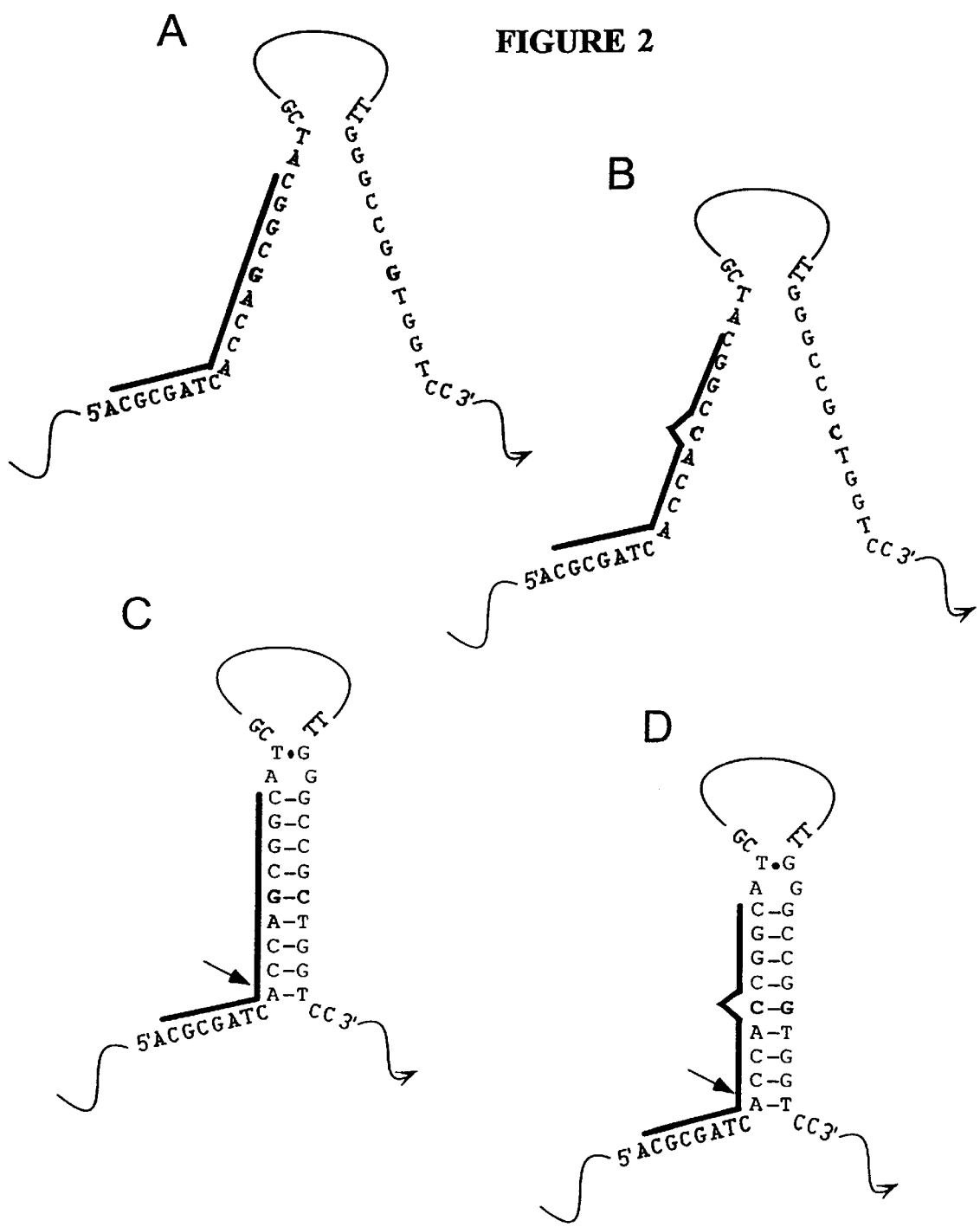
FIGS. 2A–2D provide a schematic of representation of a segment of the katG gene from *M. tuberculosis*. Depending on the sequence, the segment of the DNA can form the stem-loop structures depicted in 2C and 2D. The arrows in 2C and 2D show the sites that are cleaved when these structures are treated by the structure specific Cleavase® I nuclease. The black bar to the left of each structure indicates the region to which the katG probe would bind, with the pointed kink in the bar indicating a site of mismatch between the probe and the katG target.

The Presence of a Structure and a Probe Mismatch in Combination Provide more Sensitive Discrimination than does either Effect Alone In this Example, the effects on oligonucleotide binding of either the formation of an occlusive structure, the presence of a single-base mismatch, or the presence of both at once were examined. To separate the effects on the efficiency of binding of structure from the effects of mismatches, four katG DNA target variants were chosen (SEQ ID NOS:1, 2, 3 and 4). The structures of these four targets in the region of the probe hybridization sites are shown in FIG. 2 and the existence of the large stem-loop in structures 2C and 2D (SEQ ID NOS:3 and 4, respectively) was confirmed by digestion with the structure-specific Cleavase® I nuclease (Third Wave) and the cleavage sites are indicated by the arrows on structures 2C and 2D. The dark bar on the left of each structure in FIG. 2 indicates the region to which the capture probe is expected to bind. The pointed kink in the black bar in structures 2B and 2D indicates a site of mismatch between the capture probe and the katG target.

a) CFLP® Analysis of Mutations in the katG Gene of *M. tuberculosis* i) Generation of Plasmids Containing katG Gene Sequences

Genomic DNA isolated from wild-type *M. tuberculosis* or *M. tuberculosis* strains containing mutations in the katG gene associated with isoniazid resistance were obtained from Dr. J. Uhl (Mayo Clinic, Rochester, Minn.). These strains are termed wild-type and S315T (Cockerill, III et al., J. Infect. Dis., 171:240 [1995]). Strain S315T contains a G to C mutation in codon 315 of the wild-type katG gene.

A 620 bp region of the *M. tuberculosis* katG gene was amplified using the PCR from DNA derived from the above strains. The primers used to amplify the katG gene sequences were KatG904 (5'-AGCTCGTATGGCACCGGAAC-3')(SEQ ID NO:5) and KatG1523 (5'-TTGACCTCCCACCCGACTTG-3') (SEQ ID NO:6); these primers amplify a 620 bp region of katG gene. The PCRs were conducted in a final reaction volume of 100 μl and contained the KatG904 and KatG1523 Primers at 0.5 μM, 1.5 mM $MgCl_2$, 20 mM Tris-HCl, pH 8.3, 50 mM KCl, 0.05 % each Tween®-20 and Nonidet® P-40 non-ionic detergents, 60 µM of all 4 dNTPs. The reaction mixtures were heated at 95° C. for 3 min, then amplification was started with addition of 5 units of Taq DNA polymerase and continued for 35 cycles at 95° C. for 1 min, 60° C. for 1 min and 72° C. for 2 min.

To clone the PCR-amplified katG fragments, 1 µl of each PCR product was used for ligation into the linear pT7Blue T-vector (Novagen, Madison, Wis.). The ligation products were used to transform competent JM109 cells and clones containing pT7Blue T-vector with an insert were selected by white color on LB plates containing 40 µg/ml X-Gal, 40 µg/ml IPTG and 50 µg/ml ampicillin. For each of the PCR samples, four colonies were picked and grown overnight in 2 ml LB media containing 50 µg/ml carbenicillin. Plasmid DNA was isolated using an alkaline miniprep protocol (Sambrook et al., supra).

To analyze the cloned katG fragments, 1 µl of plasmid DNA from each clone was amplified by PCR using 100 µl reactions containing the KatG904 and KatG1523 primers at 0.5 µM, 1.5 mM $MgCl_2$, 20 mM Tris-HCl, pH 8.3, 50 mM KCl, 0.05% each Tween®-20 and Nonidet® P-40 non-ionic detergents, 60 µM of all 4 dNTPs and 5 units of Taq DNA polymerase. The PCRs were cycled 35 times at 95° C. for 1 min, 60° C. for 1 min and 72° C. for 2 min. PCR products were separated by electrophoresis on a 6% native polyacrylamide gel in 0.5×TBE buffer and clones that gave rise to a 620 bp fragment were selected for further analysis.

Fragments of DNA (391 bp), labeled on the 5' end of the sense strand with tetrachlorofluorescein (TET), were created from the cloned katG genes using primers 5'-TET-AGCTCGTATGGCACCGGAACC-3' (SEQ ID NO:7) and 5'-GGACCAGC GGCCCAAGGTAT-3' (SEQ ID NO:8). When the wild type katG DNA fragment of this size is denatured by heating and allowed to fold, nucleotides A37–C45 base pair with nucleotides G381–T389 (measured from the 5' end of the sense strand). The wild type sequence has a G at bp 41 (G41) which is complimentary to the C at bp 385 (C385) as shown in FIG. 2C; the S315T mutant sequence contains a C at bp 41 (C41) which is non-complimentary to C385 and disrupts the formation of the hairpin, as shown in FIG. 2B. Two additional non-wild type sequences were created by using an alternative primer at the 3' end (5'-GGACCACCGGCCCAAGGTATCT-3'; SEQ ID NO:9) which changed C385 to G385. This allowed creation of fragments with a G41 to G385 mismatch (FIG. 2A) and a C41 to G385 base pair (FIG. 2D).

The PCR reactions were performed as follows: PCR mixtures contained 5 ng of plasmid DNA template, 1×PCR buffer, 200 µM of each dNTP, 0.5 µM of each primer, 5 units of Taq Polymerase and water to final volume of 100 µl. The PCR cycling conditions were: 95° C. for 45", 65° C. for 1'30" and 72° C. for 2' for a total of 30 cycles, followed by a 4° C. soak. The 391 bp PCR products were purified using "High Pure PCR Product Purification Kit" (Boehringer Mannheim). This set of fragments (SEQ ID NOS:1–4) allowed a single probe to be used to assess the effects of mismatch, secondary structure or a combination of both on the formation of the complex between the probe and target.

ii) CFLP® Reactions

CFLP® reactions were performed on each 5'-TET labeled amplification product from the four KatG variants (2A–2D). Each CFLP® reaction contained approximately 20 fmole of the amplified product, 50 units of Cleavase® I nuclease in 10 µl of 1×CFLP® buffer (10 mM MOPS pH 7.5, 0.05% Tween® 20 and 0.05% Nonidet® P40 non-ionic detergents) with 0.2 mM $MnCl_2$. Reactions were assembled with all components except the enzyme and the $MnCl_2$, heated to 95° C. for 15 seconds, then cooled to the reaction temperature of 50° C. The cleavage reactions were started with the addition of the enzyme and the $MnCl_2$, and incubated for 5 minutes. The reactions were terminated by the addition of 4 µl of 95% formamide with 10 mM EDTA and 0.02% Methyl Violet. The products were heated at 95° C. for 30 sec, and aliquots were resolved by electrophoresis through 10% denaturing polyacrylamide gel (19:1 cross link) with 7 M urea in a buffer of 45 mM Tris-Borate, pH 8.3, 1.4 mM EDTA. The gel was visualized using the FMBIO-100 Image Analyzer (Hitachi). The resulting image is shown in the left panel of FIG. 3. Lanes A–D contain CFLP reaction products from reactions containing structures 2A–2D, respectively. Lanes C and D contain a product (37 nt; indicated by the arrowhead) not present in lanes A and B which indicates the presence of the large stem-loop in structures 2C and 2D shown in FIG. 2.

b) Structure Probing Analysis of *M. tuberculosis* katG Gene Targets

In these experiments, the capture probes are bound to the target DNAs in solution and then immobilized on a solid support. The 391 bp fragment of katG described above was created by PCR using a 5'-fluorescein labelled primer (SEQ ID NO:7). A hybridization mixture was assembled, containing 40 fmoles of heat-denatured, 391 bp katG PCR product having one of the four sequences depicted in FIG. 2 (SEQ ID NOS:1–4), labelled on the 5' end of the sense strand, 1 pmole of the biotinylated capture probe (SEQ ID NO:10), 10 µg/ml tRNA, 0.2% acetylated BSA, 4.5×SSPE and $H_2O$ to 100 µl.

Figure 3:
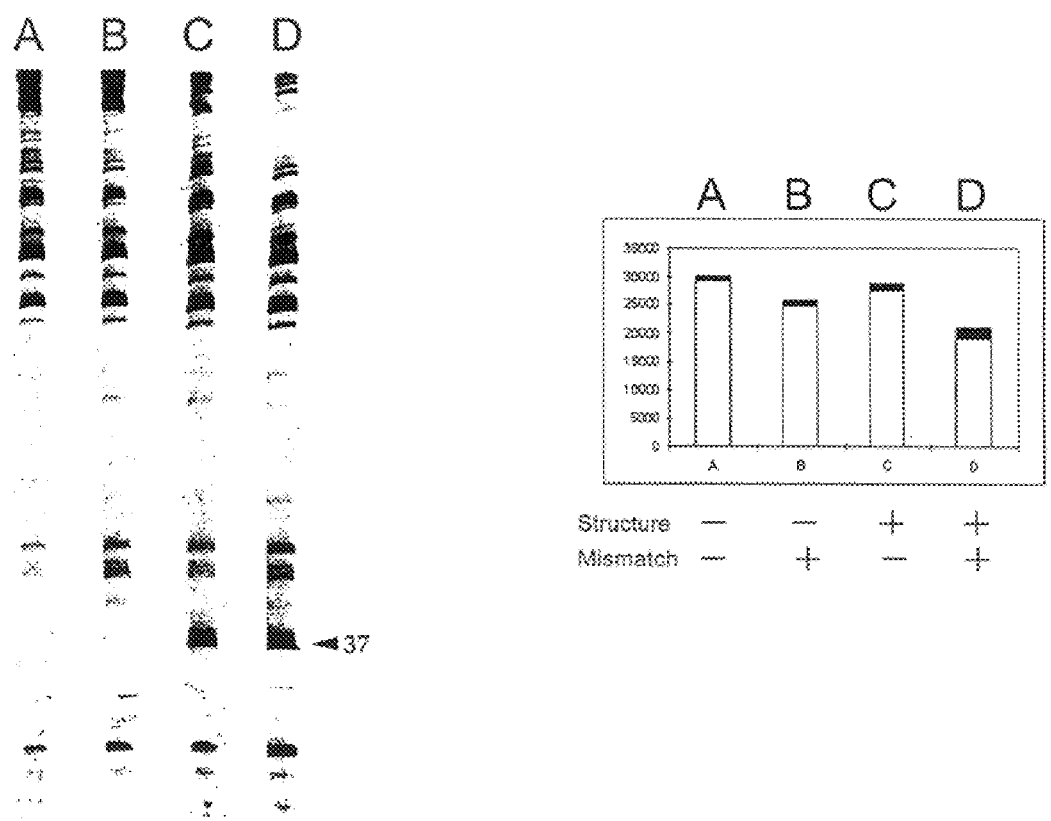
FIG. 3 shows at left a fluorescence imager scan of the cleavage patterns generated using the CFLP® method on the katG substrates. The letters above the lanes indicate that these DNA fragments contain to the corresponding structures diagrammed in FIG. 2. An arrow indicates the 37 nucleotide (nt) product of cleavage at the site indicated by the arrows in FIG. 2. The graph at the right depicts the fluorescence intensity measured when each of the molecules depicted in FIG. 2 was complexed to the katG capture probe and bound to a solid support in a structure probing assay.

Aliquots (100 µl) of the mixture were then transferred to wells in a streptavidin-coated 96-well plate (Boehringer Mannheim) and incubated at room temperature for 30 min. The plate was then washed three times with 1×PBS, with 0.01% Tween®-20 non-ionic detergent, then treated with a solution containing 0.2% I-Block (Tropix, Bedford, Mass.) and 0.05% Tween®-20 non-ionic detergent in PBS for 30 minutes to block. After blocking, the plate was washed three times with PBS with 0.1% Tween®-20 non-ionic detergent. A 1:5000 dilution of 0.75 u/µl anti-fluorescein antibody conjugated with alkaline-phosphatase in 0.2% I-block buffer was added to the plate in 100 µl/well volumes. After ½ hour, the plate was washed three times with TBS (25 mM Tris-Cl, 0.15 M NaCl, pH 7.2). One hundred microliters of Attophos™ fluorescent substrate (JBL, San Louis Obisbo, Calif.) was added to each well and the plate was incubated at room temperature for 1 hour before fluorescence readings were taken using a Perkin-Elmer Cytofluor-4000 set to excite at 450/50 nm and to and detect emission at 580/50 nm. Each assay was performed in triplicate and the standard deviation is represented by the black bar at the top of each column in the right panel of FIG. 3. The fluorescence intensity is indicated in arbitrary fluorescence units. In FIG. 3, "A–D" indicates the use of structures 2A–2D, respectively in the structure probing assay.

The results, shown in FIG. 3, indicate that not only the mismatch between target DNA and probe, but also differences in secondary structure, leads to a better discrimination between wild type and mutant DNA.

EXAMPLE 2

Figure 4:
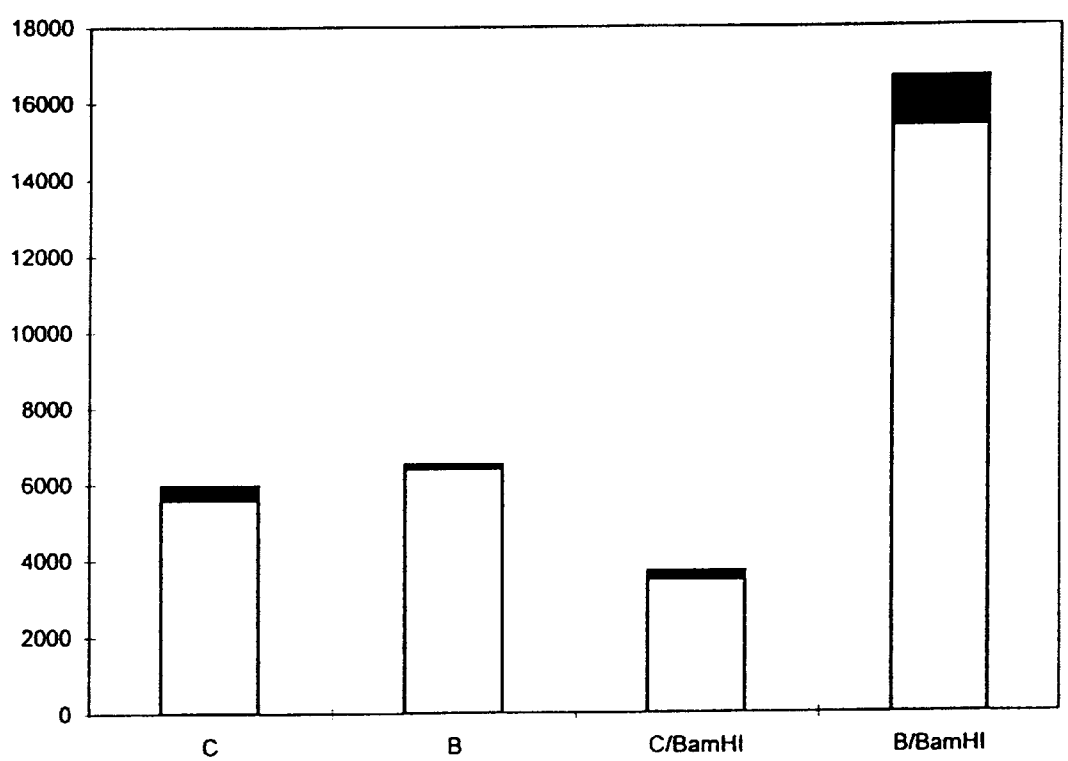
FIG. 4 show a graph that depicts the fluorescence intensity measured when two variants of the katG target DNA with different amounts of flanking sequence were bound to a microtiter plate using a single capture probe.

Changes in DNA Secondary Structure Leads to Different Binding Abilities between the Target DNA and the Capture Probe The context of a target sequence (i.e., the length and identity of the flanking nucleic acid), can influence the secondary structure, and therefore the hybridization accessibility of the target segment. To illustrate this effect, a target segment of DNA was exposed, either with or without pretreatment with a restriction enzyme, to a capture probe that is complementary to a site that is unaffected by the restriction cleavage. The restriction enzyme BamHI was used to digest the 391 bp 5'-fluorescein labeled fragments of katG DNA, either wild-type (FIG. 2C) or the S315T mutant (FIG. 2B), prepared as described in Example 1. The restriction enzyme shortens the 5' labelled fragment from 391 nt to 256 nt. The capture probe is complementary to sequence located within the first 50 nt of these katG DNA targets. Equal amounts of the DNA targets were used in all the reactions. The restriction digests included 2 pmoles of 5'-Fluorescein labeled DNA, 10 µl of 10×BamHI buffer, 160 units of BamHI enzyme and $H_2O$ to a final volume of 100 µl. The reactions were incubated at 37° C. for 2 hours. After digestion, the hybridization assay was performed as described above, using the capture probe (SEQ ID NO:10). The results are shown in FIG. 4. In FIG. 4, the amount of labeled target captured (as a target/probe complex) is shown for each target/probe complex examined (shown using arbitrary fluorescence units). In FIG. 4, the following abbreviations are used: C (structure 2C); B (structure 2B); C/BamHI (BamHI-digested structure 2C); B/BamHI (BamHI-digested structure 2B).

The 2C DNA target (SEQ ID NO:3) has a site perfectly complementary to the capture probe, while the 2B DNA target (SEQ ID NO:2) has a single base mismatch near the middle of the region of complementarity with the capture probe. Despite this mismatch, discrimination between these two 391 nt DNAs (i.e., not digested with BamHI) by hybridization to this probe is very weak. As shown in FIG. 4, the difference in the binding efficiency between wild type and mutant DNA after enzyme digestion is increased. Because the segment of the katG DNA to which the probe hybridizes is not cleaved by the enzyme, it can be concluded that it is the change in the folded structure of the target DNA that accounts for the change in the hybridization pattern. This shows that, while mismatches may enhance discrimination between nucleic acid variants, they are not necessary for discrimination between DNAs by hybridization. These results also demonstrate that variables other than the degree of complementarity (e.g., complete or partial) between the probe and target (e.g., the secondary and tertiary structure of the target) may provide a better means of discriminating between related sequences.

EXAMPLE 3

Hybridization Analysis Using Multiple Capture Probes for HCV Genotyping

Figure 5:
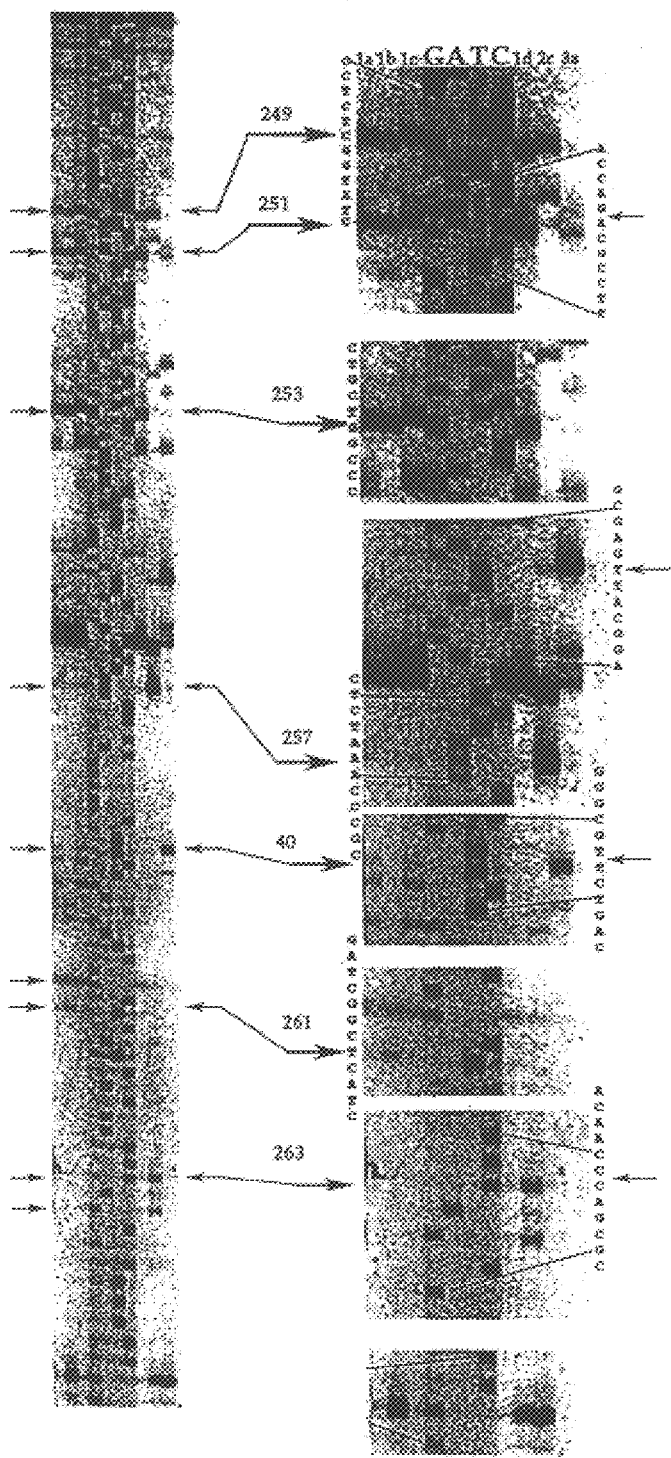
FIG. 5 shows an analysis of several types of HCV by both the CFLP® method and by DNA sequencing. The sequence lanes were resolved beside the lanes showing the products of CFLP® cleavage. This allowed precise identification of the sites cleaved, and therefore the regions of structure, in the analysis of each of the HCV genotypes. The probes selected to interact in these regions are indicated to the right (SEQ ID NOS:11–19).

Because both mismatches and structures are used in the method of the present invention for discrimination between similar nucleic acids by hybridization, the patterns created by the use of a structure specific nuclease, e.g., Cleavase® I nuclease can be used as a way of selecting regions likely to demonstrate different binding behaviors with different variants. Because the CFLP® method indicates the presence of structure in a DNA fragment of interest, and because the variations in the structures tend to be proximal to the actual sequence changes, choosing capture probes at or near the CFLP® cleavage sites increases the probability of choosing a sequence that changes in accessibility in the different variants. FIG. 5 shows a diagram depicting this means of probe selection as applied to the comparison of fragments from the Hepatitis C virus. In FIG. 5, the left panel shows an fluoroimager scan of sequencing gel in which products of CFLP® cleavage reactions are resolved next to a sequencing ladder generated using the same target DNA employed in the CFLP® cleavage reactions. The middle panel provides an enlargement of sections of the gel shown in the left panel. The right panel provides the sequence of nine HCV probes (SEQ ID NOS:11–19); these probe were synthesized such that they contained a 5'-biotin moiety.

Five subtypes of HCV; 1a, 1b, 2b, 2c, and 3a were analyzed using both the CFLP® cleavage method, and cycle sequencing. The CFLP® reactions were performed on each 5'-fluorescein labeled amplification product from each HCV isolate as follows. Each CFLP® reaction contained approximately 20 fmole of the amplified product, 25 units of Cleavase® I nuclease in 10 µl of 1×CFLP® buffer (10 mM MOPS pH 7.5, 0.05% Tween® 20 and 0.05% Nonidet® P40 non-ionic detergents) with 0.2 mM $MnCl_2$. Reactions were assembled with all components except the enzyme and the $MnCl_2$, heated to 95° C. for 15 seconds, then cooled to the reaction temperature of 55° C. The cleavage reactions were started with the addition of the enzyme and the $MnCl_2$, and incubated for 2 minutes. The reactions were terminated by the addition of 4 µl of 95% formamide with 10 mM EDTA and 0.02% Methyl Violet. The products were heated at 85° C. for 2 min, and aliquots were resolved by electrophoresis through 10% denaturing polyacrylamide gel (19:1 cross link) with 7 M urea in a buffer of 45 mM Tris-Borate, pH 8.3, 1.4 mM EDTA. The gel was visualized using the FMBIO-100 Image Analyzer (Hitachi).

The CFLP® patterns for these HCV subtypes are shown in FIG. 5. Different subtypes of HCV give different CFLP® patterns, which means that they also have different internal secondary structure. Probes were designed to detect structure differences between the 1a, 1b, 2c and 3a HCV subtypes. The capture probes are shown in the right panel of FIG. 5. The region to which each of these HCV capture probes can bind along the sequence of the HCV targets is shown in FIG. 6. In FIG. 6, the location of the probe binding regions are indicated using bold type, underlining and by placing the probe designation above the sequence. The consensus HCV sequence (SEQ ID NO:20), and the sequence of HCV subtypes 1a, 1b, 2c and 3a (SEQ ID NOS:20–23, respectively) are provided.

Figure 7:
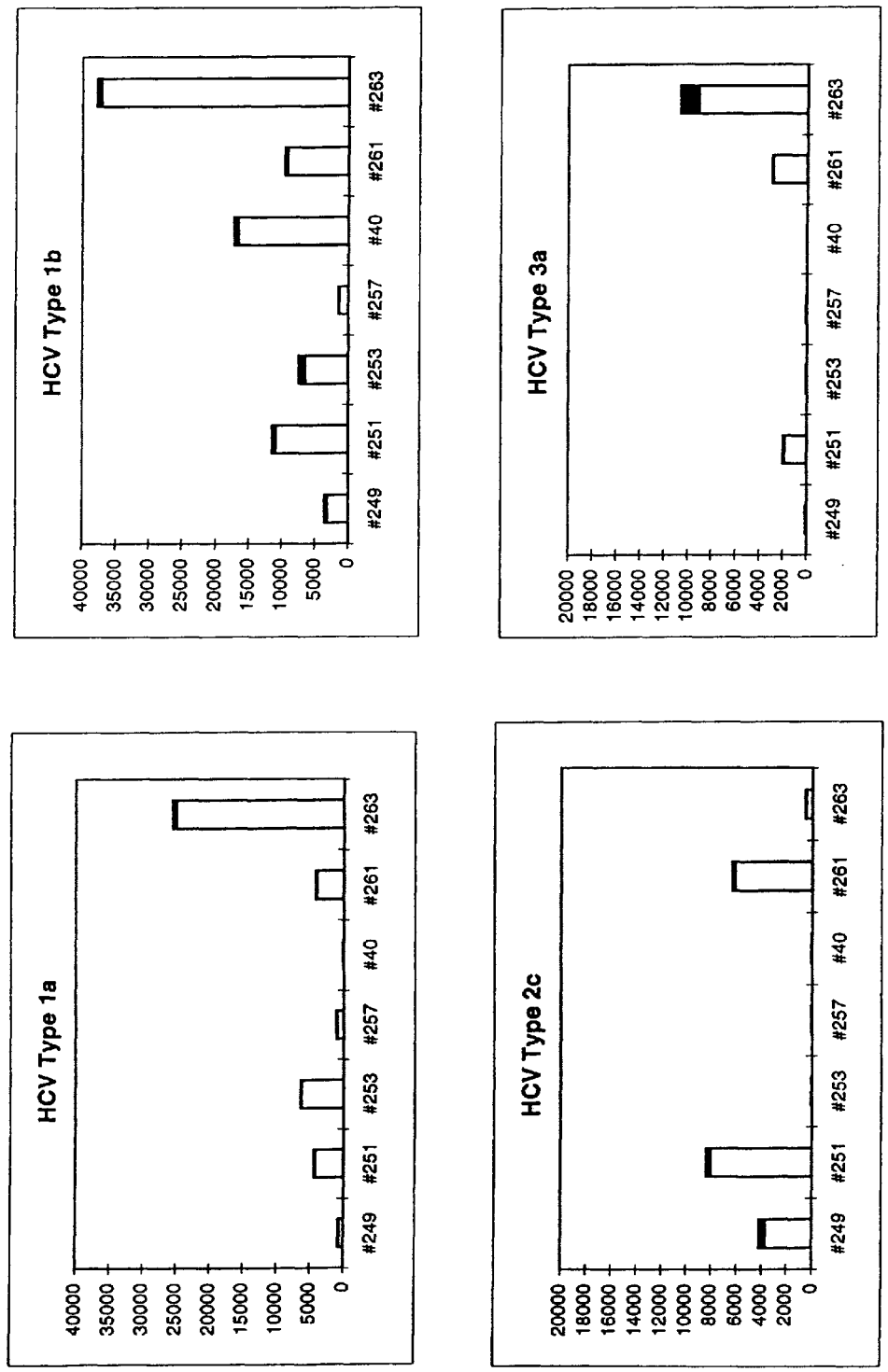
FIG. 7 shows four graphs depicting the fluorescence signal measured after the solid support capture of the indicated HCV types by the indicated probes.

The capture probes (SEQ ID NOS:11–19) were synthetically labeled with biotin at their 5' end and purified by gel-electrophoresis. The HCV target DNA was labeled with fluorescein at the 5' end of the antisense strand by PCR using a 5'-fluorescein labeled primer. The primers employed for the amplification of HCV target DNAs were: 5' primer: 5'-F1-CTCGCAAGCACCCTATCA (SEQ ID NO:24) and 3' primer: 5'-GCAGAAAGCGTCTAGCCATGG (SEQ ID NO:25). The PCR reactions included 5 ng of plasmid DNA template, 1×PCR buffer (Boehringer Mannheim), 200 µM of each dNTP, 0.5 µM of each primer (SEQ ID NOS:24 and 25), 5 units Taq DNA polymerase (Boehringer Mannheim) and water to a final volume of 100 µl. The PCR cycling conditions were: 95° C. for 45", 55° C. for 45", and 72° C. for 1', for 30 cycles followed by a 72° C. for 5' extension and a 4° C. soak. The resulting 244 bp PCR products (SEQ ID NOS:26–29 for types 1a, 1b, 2c and 3a, respectively) were purified using "High Pure PCR Product Purification Kit" (Boehringer Mannheim) and eluted in $dH_2O$ according to the manufacturer's instructions. The same amount of DNA, based on optical absorbance, was used for each sample in the capture assay. Structure probing analysis on streptavidin-coated 96-well micro-titer plates was performed as described above. Each assay was performed in triplicate and the standard deviation is shown as a black bar at the top of each column in FIG. 7. The results are shown in FIG. 7.

The column graphs of the measured fluorescence intensity for the complexes between each probe and a given target constitute a characteristic "signature" that is distinctive for each HCV subtype. The effects of structure can be illustrated by examining the signal strengths from targets binding to probe #40 (SEQ ID NO:16). While both the 1b and 3a targets are completely complementary to probe #40, the 3a target shows nearly undetectable signal, while the type 1b target signal is very strong. The binding of probe #251 (SEQ ID NO:12) to the HCV targets shows similar signal variation even though this probe is completely complementary to all four of the HCV subtype targets.

EXAMPLE 4

Effect of Temperature on Structure Probing with Oligonucleotides

Most traditional hybridization methods have a small window of temperature (i.e., about less than 10° C.) in which to produce the expected discrimination between targets. The structure probing analysis of the four HCV subtypes (describe above) under different hybridization temperatures was performed to examine the effect of temperature on both the secondary structure of DNA and the stability of the probe/target complex. Three different temperatures were used; room temperature (approx. 20 to 25° C.), 37° C. and 50° C.

The profile of the HCV subtypes 1a, 1b and 3a are shown in FIG. 7. The profiles of the HCV subtype 1b are shown in FIG. 8B. The profiles of the HCV subtype 3a are shown in FIG. 8C. The hybridization profiles of these three HCV subtypes over a 25° C. range of temperature (~25–50° C.) are shown in FIGS. 8A–8C (the numbers below each column indicates the capture probe employed; note the change in scale for each temperature tested). The profiles for these three HCV subtypes are essentially the same over the 25° C. range of temperature tested. However, the higher the temperature employed, the less stable the probe-DNA target binding becomes, so the overall fluorescence intensity was reduced. These results show that the discrimination capability of the structure probing method is very robust, maintaining consistency over a broad range of temperature.

EXAMPLE 5

Structure Probing Analysis of HCV Clinical Isolates

Structure probing analysis of HCV clinical isolates at a room temperature hybridization temperature was performed to examine the feasibility of developing a diagnostic test for HCV genotyping. Twelve HCV amplification products generated from clinical samples were obtained (Molecular Pathology Dept, Univ. of Wisconsin Clinics, Madison, Wis.) and employed in the structure probe assay. These targets were RT-PCR products of viral RNA from different patient samples amplified using the Amplicor HCV detection kit (Roche Molecular Systems, Alameda, Calif.). Further PCR reactions were performed on these clinical amplification products using the primer pair described in Example 4 (SEQ ID NOS:24 and 25) to create ds PCR products comprising 5' fluorescein labels on the anti-sense strands. The PCR conditions were as described in Example 4. The resulting HCV targets were employed in the structure probing assay which was carried out as described in Example 1.

The resulting profiles were sorted by type (based on the profiles determined for the HCV subtypes as described in Examples 3 and 4 and FIG. 7) and are shown in FIGS. 9A–9D (the types were independently determined by single pass DNA sequencing. The resulting partial sequences, sufficient to identify types are as follows: #67 (SEQ ID NO:30), #69 (SEQ ID NO:31), #72 (SEQ ID NO:32), #73 (SEQ ID NO:33), #74 (SEQ ID NO:34), #81 (SEQ ID NO:35), #85 (SEQ ID NO:36), #86 (SEQ ID NO:37) and #91 (SEQ ID NO:38).

Figure 9A:
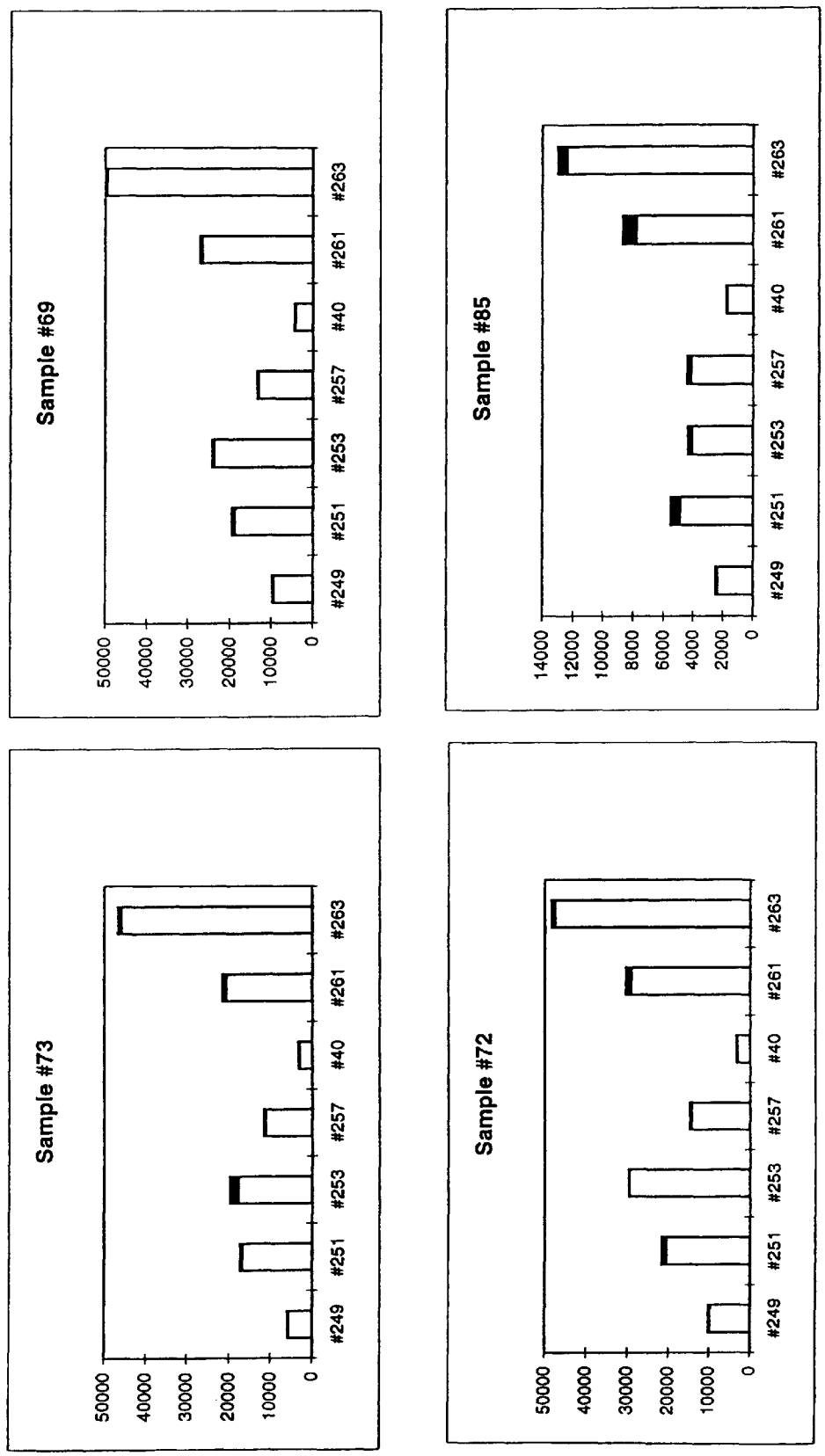
Figure 9B:
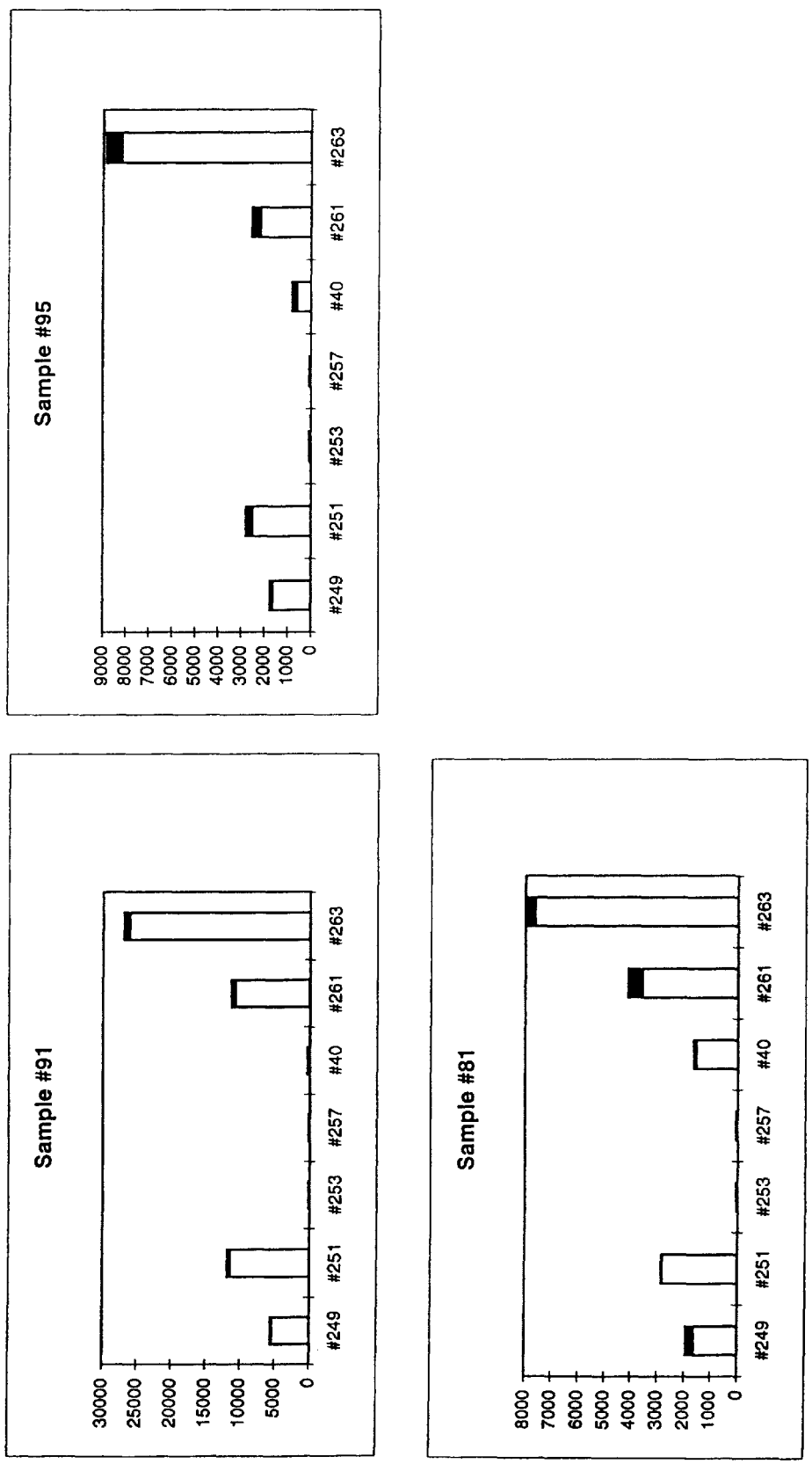
Figure 9C:
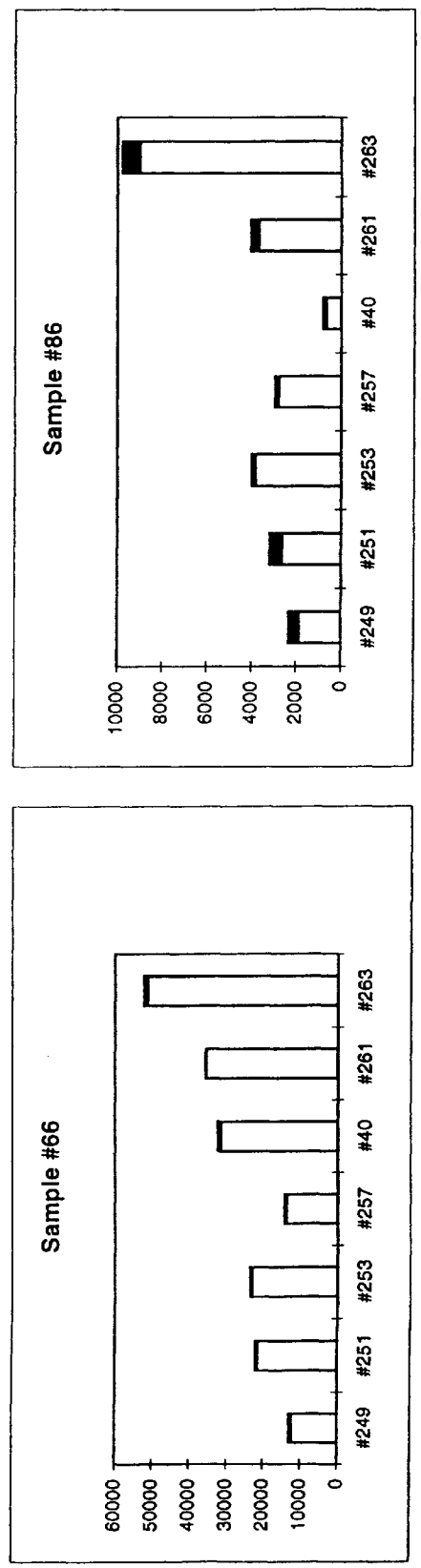

The profiles for four different amplicons of HCV type 1a are shown in FIG. 9A (#69, #72, #73 and #85) and all have a profile similar to the type 1a profile shown in FIG. 7. The profiles of three different amplicons of HCV type 3a are shown in FIG. 9B (#81, #91 and #95) and their profiles are all similar to each other and to the type 3a profile shown in FIG. 7. The profile of an amplicon of HCV type 2c (#67) and an amplicon of HCV type 2b (#74) are shown in FIG. 9D. The profiles for two amplicons of HCV 1b are shown in FIG. 9C (#66 and #86).

The profile for amplicon #86 was more similar to that of type 1a rather than type 1b. Based on CFLP® analysis, amplicon #86 was classified as type 1b. However, using the probe set shown in FIG. 9C, the hybridization profile obtained in the structure probing assay appeared more similar to that of type 1a. Sequence analysis showed that there is an extra mutation in this sample, which changed its hybridization response to probe #40, creating a profile more like that of type 1a. Based on this T to C mutation in amplicon #86, an additional capture probe having a sequence completely complimentary to amplicon #86 was tested (probe #53; SEQ ID NO:19). A structure probing assay using the amplicon #86 target and capture probe #53 generated a profile similar to a more typical type 1b profile. These results demonstrate that additional information concerning the structure of the amplicon #86 target was obtained using the structure probing assay.

These data demonstrate that an unknown (i.e., uncharacterized) set of HCV isolates can be identified by HCV type through the use of the structure probing assay, with comparison of the resulting profiles to those of previously characterized isolates (i.e., reference profiles).

It is clear from the above that the present invention provides methods for the analysis of the characteristic conformations of nucleic acids without the need for either electrophoretic separation of conformations or fragments or for elaborate and expensive methods of visualizing gels (e.g., darkroom supplies, blotting equipment or fluorescence imagers). The novel methods of the present invention allow the rapid identification of variants (e.g., mutations) within human genes as well as the detection and identification of pathogens in clinical samples.

Thus, the previous Examples that oligonucleotide binding is affected by the formation of an occlusive structure in the target DNA. In each of these cases, the oligonucleotides used to bind and capture the target nucleic acid were designed to be substantially complementary to a single region of the target. The following two Examples demonstrate the use of oligonucleotides that are designed to interact with multiple, non-contiguous regions of the target DNA. In some embodiments of the methods of the present invention, the oligonucleotides (i.e., bridging oligonucleotides) are designed to interact with regions that are brought into close proximity by the formation of folded structure in the target strand. By using short sections of complementarity on either side of the connecting segment, it is intended that the bridge oligonucleotides be dependent on the binding of both of the sections of complementarity, and that changes in, or the absence of, the intervening folded structure cause a significant change in the affinity between the bridge oligonucleotide and the target DNA.

EXAMPLE 6

Size of Complementary Regions Affects the Ability of Bridging Oligonucleotides to Discriminate Between Targets that Contain Identical Regions of Complementarity, but Different Folded Structures In this Example, the effect of length of complementarity on each side of the bridge oligonucleotides on the ability of the bridge oligonucleotide to distinguish between test molecule #80, 81 and 82 (SEQ ID NOS:39–41) was examined. As noted above, these oligonucleotides have identical regions of complementarity to which the bridge oligonucleotides of this Example may hybridize. The bridge oligonucleotides used in this test are shown in the lower half of FIG. 11A, arranged in the orientation in which they would hybridize to test molecule #80 (SEQ ID NO:39). Three bridging oligonucleotides, shown as #78, #4 and #79 (SEQ ID NOS:42, 43, 44), were used, and these had 6, 7 or 8 nucleotides of complementarity, respectively, to each side of the hairpin formed in target #80 (SEQ ID NO:39). The two regions of target complementarity were separated by a pair of thymidine nucleotides in each oligonucleotides to provide additional flexibility to the three-leg junction (Zhong et al., Biochem., 32:6898 [1993]; and Yang et al., Biochem., 35:7959 [1996]). All the biotinylated oligonucleotides were gel-purified after synthesis using the standard oligonucleotide purification methods.

In these hybridization analyses, the capture probes were bound to the target DNAs in solution and then immobilized on a solid support, as described in the previous Examples. For each of these tests (each of the three bridge oligonucleotides listed above was tested on each of the three test molecules), a hybridization mixture was assembled containing 20 fmols of a fluorescein-labeled test molecule as depicted in FIG. 10 (SEQ ID NOS:39–41), 1.5 pmole of one of the biotinylated capture probe 78, 4 or 79 (SEQ ID NOS:42–44), 10 μg/ml tRNA and 0.2% acetylated BSA, in 150 μL of 4.5×SSPE. The mixture was incubated at room temperature for 30 min.

Aliquots (100 μl) of the mixtures were then transferred to wells in a streptavidin-coated 96-well plate (Boehringer Mannheim) and incubated at room temperature for 20 min. The plate was then washed three times with TBS (25 mM Tris-Cl, 0.15 M NaCl, pH 7.2) with 0.01% Tween®-20 non-ionic detergent. Then, 100 μl of a 1:5000 dilution of 0.75 u/μl anti-fluorescein antibody conjugated with alkaline-phosphatase in 0.2% I-block buffer (Tropix, Bedford, Mass.) was added to each well. After 20 min at room temperature, the plate was washed three times with TBS with 0.01% Tween®-20. Then, 100 μl of Attophos™ fluorescent substrate (JBL, San Louis Obisbo, Calif.) were added to each well and the plate was incubated at 37° C. for 1 hour, before fluorescence readings were taken using a Perkin-Elmer Cytofluor-4000 set to excite at 450/50 mn and to and detect emission at 580/50 nm. Each assay was performed in duplicate and the standard deviation is represented by the black bar at the top of each column in the right panel of FIG. 12. In this Figure, the fluorescence intensity is indicated in arbitrary fluorescence units.

Figure 12:
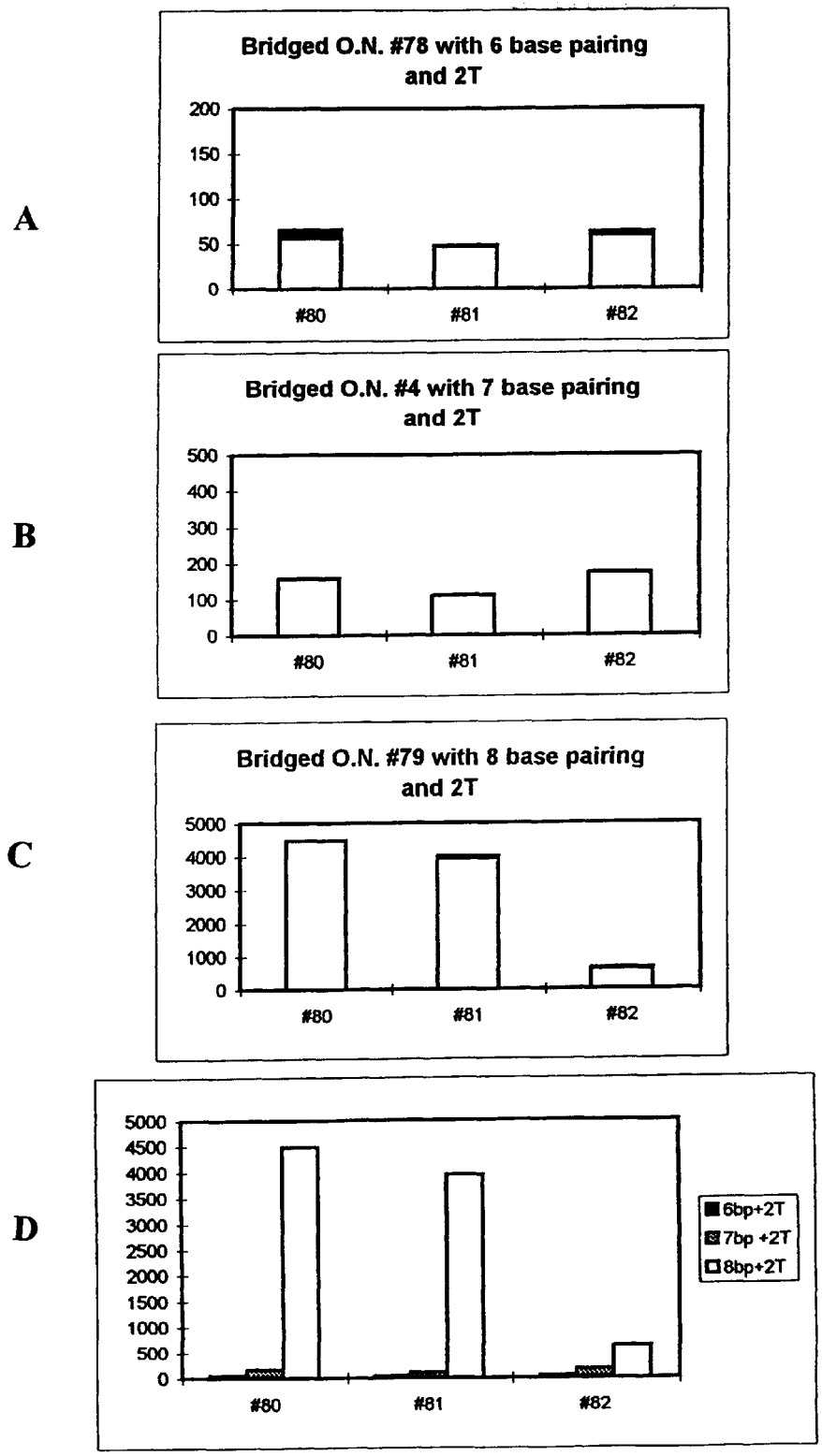
FIGS. 12A–12D show graphs depicting the fluorescence signal measured after the solid support capture of the three test molecules, #80 (SEQ ID NO:39), #81 (SEQ ID NO:40), and #82 (SEQ ID NO:41) by the indicated probes. The wider fourth panel (FIG. 12D), shows the fluorescence signal from each of the first three panels re-drawn together on a single scale of fluorescence intensity, for ease of comparison.

The results, shown in FIG. 12, indicate that the bridging oligonucleotide #79 (SEQ ID NO:44), having 8 bases pairing to each side of the hairpin in the DNA target, gives better binding activity to the target DNA than oligonucleotides that have 7 bases pairing (#4; SEQ ID NO:43), which is better than oligonucleotides that have only 6 bases pairing (#78; SEQ ID NO:42). Furthermore, the oligonucleotides with the shorter flanking sequences did not show any significant difference in binding to the different test molecules, indicating that the presence or absence of structure was immaterial to their binding under these test conditions. In contrast, the oligonucleotide with the 8 bp flanks had a 6 to 7-fold higher affinity for the folded molecules #80 (SEQ ID NO:39) and #81 (SEQ ID NO:40), when compared to the unstructured #82 (SEQ ID NO:41) molecule. This demonstrated that bridge oligonucleotides are suitable for the assessment of differences in folded structure of a target molecule, in contrast to previous reports (Francois et al., Nucl. Acid. Res. 22: 3943 [1994]).

While the 8-bp flanks are clearly the preferred size in this experimental system, the absolute number of basepairs required for any particular bridge oligonucleotide system may vary other factors affecting the stability of the interaction, as discussed above, such as with the G-C content of the hybridization site, the temperature and solution conditions under which the reaction is performed, and the nature of the structure to be bridged. Thus, it is contemplated that in some systems, bridge oligonucleotides comprise any appropriate length suitable for the assay system.

EXAMPLE 7

Bridging Oligonucleotides

In this Example, two schemes were investigated in order to determine how the bridging oligonucleotide might bind to the targeted hairpin structure, as illustrated in FIG. 11B. Although an understanding of the mechanism is not necessary in order to make and use the present invention, nor is it intended that the present invention be limited to any particular mechanism, one possibility is that one bridging oligonucleotide molecule binds to one DNA target molecule, as diagrammed in the top half of the Figure. A second possibility is that two or more of the bridging oligonucleotide molecules bind to one DNA target molecule, with the apparent increase in signal resulting from the presence of two biotin moieties on the complex facilitating binding or detection, rather than successfully spanning of a structure by a single bridge oligonucleotide.

To differentiate these two possibilities, two additional oligonucleotides were synthesized (oligonucleotide #114 and #115 [SEQ ID NOS:45 and 46, respectively]), as shown in FIG. 11B. Oligonncleotide #114 (SEQ ID NO:45) is almost identical to #79 (SEQ ID NO:44), except that two mutations have been introduced in such way that it cannot hybridize to the right side of the hairpin on the target DNA. Similarly, oligonucleotide #115 (SEQ ID NO:46) is a version of #79 (SEQ ID NO:44) having two base mutations so that it can't hybridize to the left side if the hairpin on the target DNA. If the ability of oligonucleotide #79 (SEQ ID NO:44) to bind to the folded molecules is truly dependent on a single oligonucleotide bridging the structure then neither of the 'pseudo' bridge oligonucleotides, #114 or #115 (SEQ ID NOS:45 and 46, respectively), should be able to perform in this way. However, if the increased binding is in fact due to the presence of two copies of #79 (SEQ ID NO:44), which would be arranged as depicted for #114 and #115 (SEQ ID NOS:45 and 46, respectively) in the bottom half of FIG. 11B, then #114 and #115 (SEQ ID NOS:45 and 46, respectively) used together should give the same result.

Figure 11A:

In addition to the test of the bridging function, the necessity of the spacing thymidines in the center of each bridge oligonucleotide was assessed. An oligonucleotide having the same complementary flanking sequences as oligonucleotide #79, but lacking the two T's in the middle, was created. This oligonucleotide (#116 [SEQ ID NO:47]), is depicted in the bottom half of FIG. 11A. In addition, to test the necessity of having a physical linkage between the binding halves of #79 (SEQ ID NO:44), to half molecules were created, each having complementarity to one of side of the test molecules, #117 (SEQ ID NO:48) to the right side and #118 (SEQ ID NO:49) to left side, as depicted in FIG. 11A, and each having one of the two spacer T residues. Finally, two 10-mer oligonucleotides were created, each with sufficient contiguous complementarity to bind without any bridging activity. One of these was complementary to the left flank (#FD91; SEQ ID NO:50), which is unstructured in all cases, while the other was complementary to the sequence involved in the structures of the folded test molecules (#2; SEQ ID NO:51). These are depicted in the top half of FIG. 11A.

The hybridization analyses were performed as described in Example 6, except that 15 fmoles of the fluorescein labeled test molecules were used, and the amount of bridge oligonucleotide was held to a total of 1.5 pmole when #114 and #115 (SEQ ID NOS:45 and 46, respectively) were used in combination. The results are shown in FIGS. 13A and 13B.

Taking the results in reverse order: the 10-mer control oligonucleotides showed the expected profiles in binding i.e., the oligonucleotide complementary to the unstructured region, #FD91 (SEQ ID NO:50), bound with nearly equal affinity to each of the test molecules, while the oligonucleotide complementary to the portion that forms structure in molecules #80 and #81 (SEQ ID NOS:39 and 40, respectively) bound well only to unstructured test molecule #82 (SEQ ID NO:41). This further illustrates that structure alone is an important determinant in the binding of the capture probes in embodiments of the methods of the present invention.

Figure 13A:
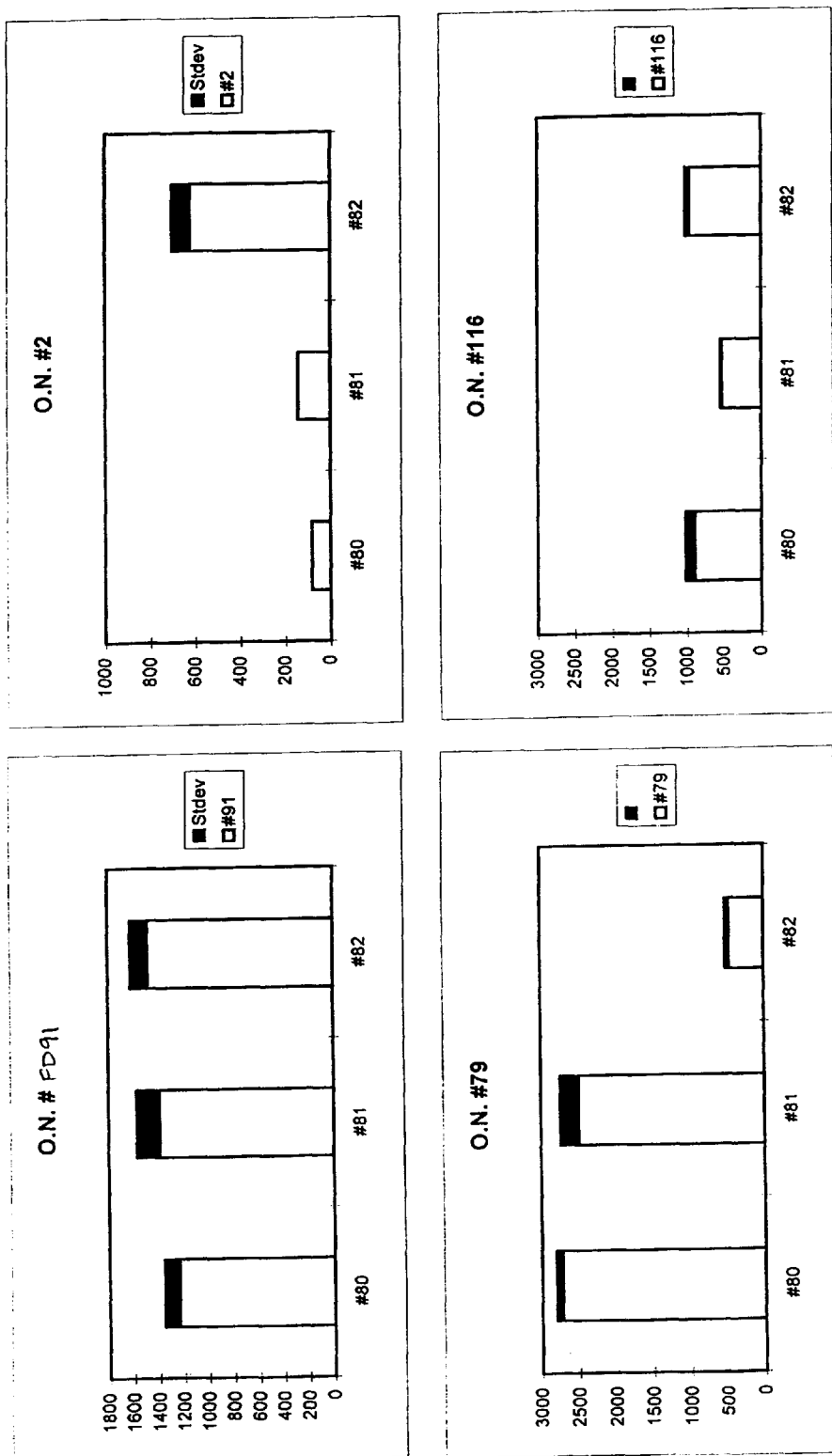
FIGS. 13A and 13B show graphs depicting the fluorescence signal measured after the solid support capture of the three test molecules, #80 (SEQ ID NO:39), #81 (SEQ ID NO:40), and #82 (SEQ ID NO:41) by the indicated probes. The names of the probes used in each capture test are indicated above each individual panel in these Figure panels.

When the oligonucleotide without any spacer residues, #116 (SEQ ID NO:47), was tested for its ability to bind the test molecules, it was found that this oligonucleotide could not distinguish between the folded and unfolded molecules (See, FIG. 13A). This demonstrated that hybridization across structures is greatly enhanced by the presence of some spacing material between the segments of complementarity.

Figure 13B:
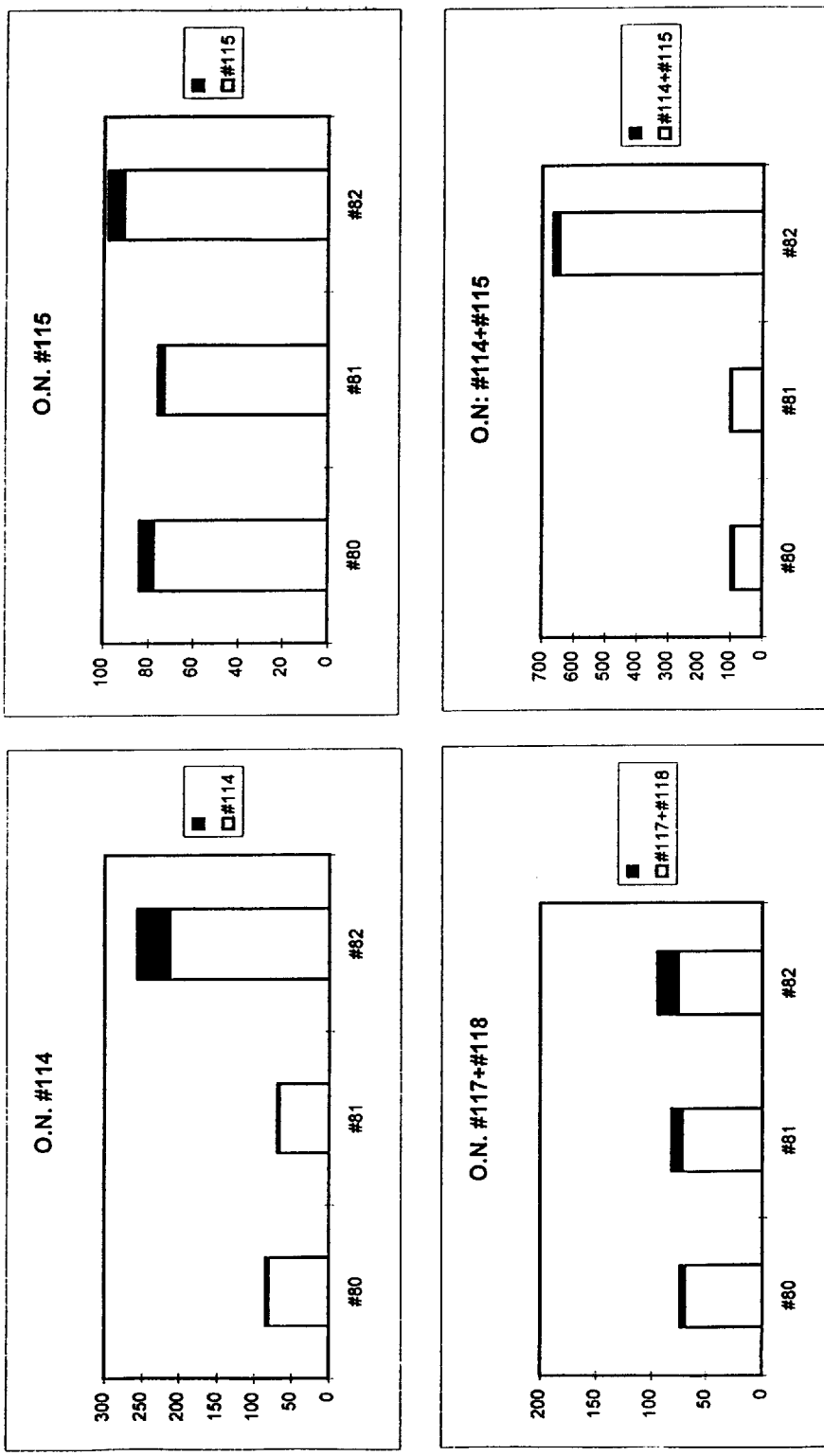

Finally, the results of testing the pseudo bridge oligonucleotides, separately and in combination, are shown in FIG. 13B. It can be seen by these data, that oligonucleotides #114 and #115 (SEQ ID NOS:45 and 46, respectively) are not capable, either alone or in combination, to duplicate the binding profile of the true bridge, #79 (SEQ ID NO:44). The enhanced binding to the unstructured test molecule #82 (SEQ ID NO:41) is possibly attributable to the accessibility of this molecule for binding both oligonucleotides. Note that the fluorescence signal seen with the combination of #s 114, 115 and molecule #82 (SEQ ID NOS: 45, 46, and 41, respectively), about 650 fluorescence units, is nearly identical to the signal seen when #79 (SEQ ID NO:44) is combined with #82 (SEQ ID NO:41). This supports the idea that two copies of #79 (SEQ ID NO:44) may be involved in creating the signal with #82 (SEQ ID NO:41).

It is clear from the above that the present invention provides methods for the analysis of the characteristic conformations of nucleic acids without the need for either electrophoretic separation of conformations or fragments or for elaborate and expensive methods of visualizing gels (e.g., darkroom supplies, blotting equipment or fluorescence imagers). The novel methods of the present invention allow the rapid identification of variants (e.g., mutations) within human genes as well as the detection and identification of pathogens in clinical samples.

It is also clear from the above that the present invention provides methods for the analysis of secondary structure within nucleic acids, without the need for either electrophoretic separation of conformations or fragments or for elaborate and expensive methods of visualizing gels (e.g., darkroom supplies, blotting equipment or fluorescence imagers). The novel methods of the present invention allow the rapid identification of variants (e.g., mutations) within genes obtained from various organisms, including humans.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A method for capturing bridging oligonucleotides, comprising:
   a) providing:
      i) a first folded target having a nucleic acid sequence comprising first and second portions, said first and second portions each comprising one or more double stranded regions and one or more single stranded regions;
      ii) a second folded target having a nucleic acid sequence comprising a first portion that is identical to said first portion of said first folded target and a second portion that differs from said second portion of said first folded target because of a variation in nucleic acid sequence relative to said first folded target, said first and second portions each comprising one or more double stranded regions and one or more single stranded regions;
      iii) first and second bridging oligonucleotides said first bridging oligonucleotide complementary to said first portion of said first and second folded targets and said second bridging oligonucleotide complementary to said second portion of said first and second folded targets; and
      iv) a solid support comprising first, second, third and fourth capture zones, each zone capable of capturing and immobilizing said first and second bridging oligonucleotides;
   b) contacting said first folded target with said first bridging oligonucleotide under conditions such that said first bridging oligonucleotide binds to said first folded target to form a probe/folded target complex in a first mixture;
   c) contacting said first folded target with said second bridging oligonucleotide under conditions such that said second bridging oligonucleotide binds to said first folded target to form a probe/folded target complex in a second mixture;
   d) contacting said second folded target with said first bridging oligonucleotide to form a third mixture;
   e) contacting said second folded target with said second bridging oligonucleotide to form fourth mixture; and
   f) adding said first, second, third and fourth mixtures to said first, second, third and fourth capture zones of said solid support, respectively, under conditions such that said first and second bridging oligonucleotides are captured and immobilized.

2. The method of claim 1, wherein said first bridging oligonucleotide in step d) does not substantially hybridize to said second folded target.

3. The method of claim 1, wherein the hybridization of said first bridging oligonucleotide in step d) to said second folded target is reduced relative to the hybridization of said first bridging oligonucleotide in step c) to said first folded target.

4. The method of claim 1, wherein said first and second targets comprise DNA.

5. The method of claim 1, wherein said first and second bridging oligonucleotides comprise DNA.

6. A method for forming a probe/folded target complex, comprising:
   a) providing:
      i) a first folded target having a nucleic acid sequence comprising first and second portions, wherein said first and second portions each comprise one or more double stranded regions and one or more single stranded regions;
      ii) a second folded target having a nucleic acid sequence comprising a first portion that is identical to said first portion of said first folded target, and a second portion that differs from said second portion of said first folded target because of a variation in nucleic acid sequence relative to said first folded target, said first and second portions each comprising one or more double stranded regions and one or more single stranded regions;
      iii) a solid support comprising first and second testing zones, each of said zones comprising immobilized first and second bridging oligonucleotides, said first bridging oligonucleotide complementary to said first portion of said first and second folded targets and second bridging oligonucleotide complementary to said second portion of said first and second folded targets; and b) contacting said first and second folded targets with said solid support under conditions such that said first and second bridging oligonucleotides hybridize to said first folded target to form a probe/folded target complex.

7. The method of claim 6, wherein said contacting of step b) comprises adding said first folded target to said first testing zone and adding said second folded target to said second testing zone.

8. The method of claim 6, wherein said first and second bridging oligonucleotides are immobilized in separate portions of said testing zones.

9. The method of claim 8, wherein said first bridging oligonucleotide in said second testing zone does not substantially hybridize to said second folded target.

10. The method of claim 8, wherein said first bridging oligonucleotide in said second testing zone hybridizes to said second folded target with a reduced efficiency compared to the hybridization of said first bridging oligonucleotide in first testing zone to said first folded target.

11. The method of claim 6, wherein said first and second folded targets comprise DNA.

12. The method of claim 6, wherein said first and second folded targets comprise RNA.

13. The method of claim 6, wherein said first and second bridging oligonucleotides comprise DNA.

14. A method of identifying a nucleotide sequence of a target nucleic acid based on its folded structure, comprising the steps of:

a) providing:
  i) two or more copies of a target nucleic acid suspected of having a particular nucleotide sequence, said sequence permitting formation of a folded structure comprising one or more single-stranded regions and further comprising two or more non-contiguous portions and one or more intervening regions,
  ii) a first oligonucleotide probe comprising a bridging oligonucleotide probe comprising at least two regions, each of said regions being complementary to a different one of at least two of said non-contiguous portions of said target nucleic acid, and
  iii) a second oligonucleotide probe selected from the group consisting of a non-bridging probe having a region of complementarity to said target nucleic acid, and a second bridging oligonucleotide comprising at least two regions, each of said regions being complementary to a different one of at least two of said non-contiguous portions of said target nucleic acid;

b) contacting at least one copy of said target nucleic acid with said first oligonucleotide probe to form a first probe/folded target complex;

c) contacting at least one copy of said target nucleic acid with said second oligonucleotide to form a second probe/folded target complex; and d) measuring amounts of each of said first and said second probe/folded target complexes wherein the measured amount of one of said probe/folded target complexes as compared to the other probe/folded target complex is indicative of the sequence of the target nucleic acid.

15. The method of claim 14, wherein said one or more intervening regions of said target nucleic acid comprises at least five nucleotides.

16. The method of claim 14, wherein said measuring amounts of each of said first and said second probe/folded target complexes comprises quantitating the amount of said probe/folded target complex formed.

17. The method of claim 14, wherein said first and said second probes in said probe/folded target complexes are hybridized to at least one single stranded region of said folded target.

18. The method of claim 14, wherein at least one of said oligonucleotide probes further comprises a moiety that permits the capture of said oligonucleotide probe by a solid support.

19. The method of claim 18, wherein measuring amounts of each of said first and said second probe/folded target complexes comprises exposing said probe/folded target complexes to one or more solid supports under conditions such that said first or said second oligonucleotide probe is captured by said one or more solid supports.

20. The method of claim 18, wherein said moiety comprises a biotin moiety and said sold support comprises a surface having a compound capable of binding to said biotin moiety, said compound selected from the group consisting of avidin and streptavidin.

21. The method of claim 14, wherein said target nucleic acid is labelled.

22. The method of claim 14, wherein said target nucleic acid comprises a sequence having a moiety that permits its capture by a solid support.

23. The method of claim 22, wherein said measuring amounts of each of said first and said second probe/folded target complexes comprises exposing said probe/folded target complex to a solid support under conditions such that said folded target is captured by said solid support.

24. The method of claim 22, wherein said moiety comprises a biotin moiety and said solid support comprises a surface having a compound capable of binding to said biotin moiety, said compound selected from the group consisting of avidin and streptavidin.

25. The method of claim 14, wherein said first and said second oligonucleotide probes are labelled.

26. The method of claim 14, wherein said first and said second oligonucleotide probes are attached to one or more solid supports.

27. The method of claim 14, wherein said target nucleic acid is attached to a solid support.

28. The method of claim 14, wherein said target nucleic acid comprises DNA.

29. The method of claim 14, wherein said target nucleic acid comprises RNA.

* * * * *

UNITED STATES PATENT AND TRADEMARK OFFICE
CERTIFICATE OF CORRECTION

| | |
|---|---|
| PATENT NO. | : 6,210,880 B1 |
| APPLICATION NO. | : 08/934097 |
| DATED | : April 3, 2001 |
| INVENTOR(S) | : James E. Dahlberg et al. |

It is certified that error appears in the above-identified patent and that said Letters Patent is hereby corrected as shown below:

Please insert before "Field Of Invention" the following paragraph: line 5

--This invention was made with United States Government support under grant number NIH R44 GM51704 awarded by the National Institutes of Health. The United States Government has certain rights in this invention.--

Signed and Sealed this

Seventeenth Day of July, 2007

JON W. DUDAS
*Director of the United States Patent and Trademark Office*